US011053477B2

(12) United States Patent
Wells et al.

(10) Patent No.: US 11,053,477 B2
(45) Date of Patent: *Jul. 6, 2021

(54) METHODS AND SYSTEMS FOR CONVERTING PRECURSOR CELLS INTO GASTRIC TISSUES THROUGH DIRECTED DIFFERENTIATION

(71) Applicant: Children's Hospital Medical Center, Cincinnati, OH (US)

(72) Inventors: James Macormack Wells, Cincinnati, OH (US); Kyle William McCracken, Cincinnati, OH (US)

(73) Assignee: Children's Hospital Medical Center, Cincinnati, OH (US)

( * ) Notice: Subject to any disclaimer, the term of this patent is extended or adjusted under 35 U.S.C. 154(b) by 105 days.

This patent is subject to a terminal disclaimer.

(21) Appl. No.: 16/188,597

(22) Filed: Nov. 13, 2018

(65) Prior Publication Data

US 2019/0153397 A1    May 23, 2019

Related U.S. Application Data

(63) Continuation of application No. 15/312,939, filed as application No. PCT/US2015/032626 on May 27, 2015, now Pat. No. 10,174,289.

(Continued)

(51) Int. Cl.
*C12N 5/071* (2010.01)

(52) U.S. Cl.
CPC ......... *C12N 5/0697* (2013.01); *C12N 5/0679* (2013.01); *C12N 2501/11* (2013.01); *C12N 2501/113* (2013.01); *C12N 2501/115* (2013.01); *C12N 2501/119* (2013.01); *C12N 2501/155* (2013.01); *C12N 2501/16* (2013.01);

(Continued)

(58) Field of Classification Search
None
See application file for complete search history.

(56) References Cited

U.S. PATENT DOCUMENTS

| 5,912,227 A | 6/1999 | Croom, Jr. et al. |
| 5,942,435 A | 8/1999 | Wheeler |

(Continued)

FOREIGN PATENT DOCUMENTS

| CN | 103154237 A | 6/2013 |
| CN | 103561751 A | 2/2014 |

(Continued)

OTHER PUBLICATIONS

Barlow, A.J., et al., "Critical numbers of neural crest cells are required in the pathways from the neural tube to the foregut to ensure complete enteric nervous system formation," Development, 2008, 135:1681-1691, 11 pgs.

(Continued)

*Primary Examiner* — David W Berke-Schlessel
(74) *Attorney, Agent, or Firm* — Knobbe, Martens, Olson & Bear, LLP

(57) ABSTRACT

Disclosed are methods of inducing formation of a gastric cells and/or a gastric tissue, such as in the form of a gastric organoid. The formation of gastric cells and/or tissue may be carried out by the activating and/or inhibiting of one or more signaling pathways within a precursor cell. Also disclosed are methods for using the disclosed gastric cells, gastric tissues, and/or gastric organoids derived from precursor cells.

18 Claims, 19 Drawing Sheets

Specification includes a Sequence Listing.

Related U.S. Application Data

(60) Provisional application No. 62/003,719, filed on May 28, 2014.

(52) U.S. Cl.
CPC .. *C12N 2501/385* (2013.01); *C12N 2501/415* (2013.01); *C12N 2501/727* (2013.01); *C12N 2506/02* (2013.01); *C12N 2506/45* (2013.01)

(56) References Cited

U.S. PATENT DOCUMENTS

| | | |
|---|---|---|
| 6,607,501 B2 | 8/2003 | Gorsuch |
| 7,160,719 B2 | 1/2007 | Nyberg |
| 7,291,626 B1 | 11/2007 | Beachy et al. |
| 7,326,572 B2 | 2/2008 | Fisk et al. |
| 7,510,876 B2 | 3/2009 | D'Amour et al. |
| 7,514,185 B2 | 4/2009 | Fukushima et al. |
| 7,541,185 B2 | 6/2009 | D'Amour et al. |
| 7,625,753 B2 | 12/2009 | Kelly et al. |
| 7,695,958 B2 | 4/2010 | Funatsu et al. |
| 7,704,738 B2 | 4/2010 | D'Amour et al. |
| 7,727,998 B2 | 6/2010 | Moriya et al. |
| 7,776,592 B2 | 8/2010 | Wandinger-Ness et al. |
| 7,927,869 B2 | 4/2011 | Rosero |
| 7,985,585 B2 | 7/2011 | D'Amour et al. |
| 7,993,916 B2 | 8/2011 | Agulnick et al. |
| 8,187,878 B2 | 5/2012 | Dalton et al. |
| 8,216,826 B2 | 7/2012 | Lee et al. |
| 8,216,836 B2 | 7/2012 | D'Amour et al. |
| 8,298,822 B2 | 10/2012 | Kruse et al. |
| 8,318,492 B2 | 11/2012 | Choo et al. |
| 8,501,476 B2 | 8/2013 | Morgan et al. |
| 8,586,357 B2 | 11/2013 | D'Amour et al. |
| 8,603,809 B2 | 12/2013 | Kruse |
| 8,609,406 B2 | 12/2013 | Subramanian et al. |
| 8,609,413 B2 | 12/2013 | Suter et al. |
| 8,623,645 B2 | 1/2014 | D'Amour et al. |
| 8,632,645 B2 | 1/2014 | Daitou et al. |
| 8,633,024 B2 | 1/2014 | D'Amour et al. |
| 8,642,339 B2 | 2/2014 | Sato et al. |
| 8,647,873 B2 | 2/2014 | D'Amour et al. |
| 8,658,151 B2 | 2/2014 | Kelly et al. |
| 8,685,386 B2 | 4/2014 | West et al. |
| 8,685,730 B2 | 4/2014 | Odorico et al. |
| 8,758,323 B2 | 6/2014 | Michaud et al. |
| 9,127,254 B2 | 9/2015 | Cohen et al. |
| 9,133,439 B2 | 9/2015 | Davis et al. |
| 9,181,301 B2 | 11/2015 | Carlson et al. |
| 9,200,258 B2 | 12/2015 | Mezghanni et al. |
| 9,206,393 B2 | 12/2015 | Kruse |
| 9,234,170 B2 | 1/2016 | Snoeck et al. |
| 9,334,479 B2 | 5/2016 | Herrera Sanchez et al. |
| 9,375,514 B2 | 6/2016 | Kruse et al. |
| 9,381,181 B2 | 7/2016 | Roberts et al. |
| 9,394,522 B2 | 7/2016 | Brolen et al. |
| 9,446,076 B2 | 9/2016 | Gaussin et al. |
| 9,447,380 B2 | 9/2016 | Subramanian et al. |
| 9,476,030 B2 | 10/2016 | Gadue et al. |
| 9,499,795 B2 | 11/2016 | D'Amour et al. |
| 9,605,243 B2 | 3/2017 | D'Amour et al. |
| 9,616,039 B2 | 4/2017 | Roberts et al. |
| 9,618,500 B2 | 4/2017 | Giselbrecht et al. |
| 9,650,609 B2 | 5/2017 | Nyberg |
| 9,675,646 B2 | 6/2017 | Bitar |
| 9,677,085 B2 | 6/2017 | Guye et al. |
| 9,719,067 B2 | 8/2017 | Snoeck et al. |
| 9,719,068 B2 | 8/2017 | Wells et al. |
| 9,732,116 B2 | 8/2017 | Steiner et al. |
| 9,752,124 B2 | 9/2017 | Sato et al. |
| 9,763,964 B2 | 9/2017 | Pellicciari et al. |
| 9,765,301 B2 | 9/2017 | Huch Ortega et al. |
| 9,771,562 B2 | 9/2017 | Shen et al. |
| 9,790,470 B2 | 10/2017 | Vallier et al. |
| 9,828,583 B2 | 11/2017 | Rauagopal et al. |
| 9,849,104 B2 | 12/2017 | Bisgaier et al. |
| 9,850,461 B2 | 12/2017 | Rizzi et al. |
| 9,856,458 B2 | 1/2018 | Rosowski et al. |
| 9,878,005 B2 | 1/2018 | Johns et al. |
| 9,914,920 B2 | 3/2018 | Goodwin et al. |
| 9,926,532 B2 | 3/2018 | Esteban et al. |
| 9,938,499 B2 | 4/2018 | Slukvin et al. |
| 10,000,740 B2 | 6/2018 | Vallier et al. |
| 10,023,922 B2 | 7/2018 | Stelzer et al. |
| 10,045,977 B2 | 8/2018 | Wu et al. |
| 10,047,341 B2 | 8/2018 | Yu et al. |
| 10,052,337 B2 | 8/2018 | Lancaster et al. |
| 10,087,416 B2 | 10/2018 | Chan et al. |
| 10,087,417 B2 | 10/2018 | Freed et al. |
| 10,100,279 B2 | 10/2018 | Nicholas et al. |
| 10,130,748 B2 | 11/2018 | Nyberg et al. |
| 10,172,889 B2 | 1/2019 | Sokal et al. |
| 10,174,289 B2 | 1/2019 | Wells et al. |
| 10,179,176 B2 | 1/2019 | Kay et al. |
| 10,220,386 B2 | 3/2019 | Williamson et al. |
| 10,222,370 B2 | 3/2019 | Keshavarzian et al. |
| 10,260,039 B2 | 4/2019 | Bhatia et al. |
| 10,265,153 B2 | 4/2019 | La Francesca et al. |
| 10,265,453 B2 | 4/2019 | Flieg et al. |
| 10,301,303 B2 | 5/2019 | Liu |
| 10,350,147 B2 | 7/2019 | Kyrkanides et al. |
| 10,369,254 B2 | 8/2019 | Yanagawa et al. |
| 10,407,664 B2 | 9/2019 | Knoblich et al. |
| 10,426,757 B2 | 10/2019 | Sabatini et al. |
| 10,449,221 B2 | 10/2019 | Kotton et al. |
| 10,472,612 B2 | 11/2019 | Ingber et al. |
| 10,479,977 B2 | 11/2019 | Wang et al. |
| 10,487,314 B2 | 11/2019 | Accili et al. |
| 10,532,111 B2 | 1/2020 | Kay et al. |
| 10,538,741 B2 | 1/2020 | Sokal et al. |
| 10,545,133 B2 | 1/2020 | Ewald et al. |
| 10,555,929 B2 | 2/2020 | Mantzoros |
| 2003/0129751 A1 | 7/2003 | Grikscheit et al. |
| 2005/0266554 A1 | 12/2005 | D'Amour et al. |
| 2006/0110369 A1 | 5/2006 | Funatsu et al. |
| 2006/0236415 A1 | 10/2006 | Silversides et al. |
| 2007/0238169 A1 | 10/2007 | Abilez et al. |
| 2007/0239083 A1 | 10/2007 | Voss |
| 2008/0193421 A1 | 8/2008 | Kruse et al. |
| 2009/0011502 A1 | 1/2009 | D'Amour et al. |
| 2009/0042287 A1 | 2/2009 | D'Amour et al. |
| 2009/0220959 A1 | 9/2009 | D'Amour et al. |
| 2009/0253202 A1 | 10/2009 | D'Amour et al. |
| 2009/0263357 A1 | 10/2009 | Sayre et al. |
| 2010/0016410 A1 | 1/2010 | Wagner et al. |
| 2010/0041150 A1 | 2/2010 | Kelly et al. |
| 2010/0048871 A1 | 2/2010 | Cho et al. |
| 2010/0075295 A1 | 3/2010 | Dryden et al. |
| 2010/0151568 A1 | 6/2010 | D'Amour et al. |
| 2011/0151564 A1 | 6/2011 | Menu et al. |
| 2011/0218512 A1 | 9/2011 | Tullis et al. |
| 2011/0294735 A1 | 12/2011 | Marsh et al. |
| 2012/0071451 A1 | 3/2012 | Spenard et al. |
| 2012/0135519 A1 | 5/2012 | Ameri et al. |
| 2012/0149630 A1 | 6/2012 | Zugates et al. |
| 2012/0196275 A1 | 8/2012 | Mezghanni et al. |
| 2012/0196312 A1 | 8/2012 | Sato et al. |
| 2012/0264209 A1 | 10/2012 | Odorico et al. |
| 2013/0031645 A1 | 1/2013 | Touboul et al. |
| 2013/0095567 A1 | 4/2013 | Brolen et al. |
| 2013/0115673 A1 | 5/2013 | West et al. |
| 2013/0137130 A1 | 5/2013 | Wells et al. |
| 2013/0189327 A1 | 7/2013 | Ortega et al. |
| 2013/0217005 A1 | 8/2013 | Snoeck et al. |
| 2013/0281374 A1 | 10/2013 | Levy et al. |
| 2013/0316442 A1 | 11/2013 | Meurville et al. |
| 2014/0038279 A1 | 2/2014 | Ingber et al. |
| 2014/0044713 A1 | 2/2014 | De Lau et al. |
| 2014/0141509 A1 | 5/2014 | Gadue et al. |
| 2014/0193905 A1 | 7/2014 | Kelly et al. |
| 2014/0212910 A1 | 7/2014 | Bhatia et al. |
| 2014/0234953 A1 | 8/2014 | Vacanti et al. |
| 2014/0243227 A1 | 8/2014 | Clevers et al. |
| 2014/0273210 A1 | 9/2014 | Baker et al. |

(56) References Cited

U.S. PATENT DOCUMENTS

| | | |
|---|---|---|
| 2014/0302491 A1 | 10/2014 | Nadauld et al. |
| 2014/0308695 A1 | 10/2014 | Bruce et al. |
| 2014/0336282 A1 | 11/2014 | Ewald et al. |
| 2015/0017140 A1 | 1/2015 | Bhatia et al. |
| 2015/0151297 A1 | 6/2015 | Williamson et al. |
| 2015/0153326 A1 | 6/2015 | Kogel et al. |
| 2015/0197802 A1 | 7/2015 | Zink et al. |
| 2015/0201588 A1 | 7/2015 | Kamb et al. |
| 2015/0238656 A1 | 8/2015 | Orlando et al. |
| 2015/0273071 A1 | 10/2015 | Green et al. |
| 2015/0290154 A1 | 10/2015 | Roberts et al. |
| 2015/0330970 A1 | 11/2015 | Knoblich et al. |
| 2015/0343018 A1 | 12/2015 | Sansonetti et al. |
| 2015/0359849 A1 | 12/2015 | Greenberg et al. |
| 2015/0361393 A1 | 12/2015 | Nicholas et al. |
| 2016/0002602 A1 | 1/2016 | Almeida-Porada et al. |
| 2016/0022873 A1 | 1/2016 | Besner et al. |
| 2016/0060707 A1 | 3/2016 | Goldenberg et al. |
| 2016/0068805 A1 | 3/2016 | Martin et al. |
| 2016/0101133 A1 | 4/2016 | Basu et al. |
| 2016/0102289 A1 | 4/2016 | Yu et al. |
| 2016/0121023 A1 | 5/2016 | Edelman et al. |
| 2016/0122722 A1 | 5/2016 | Ejiri et al. |
| 2016/0143949 A1 | 5/2016 | Ingber et al. |
| 2016/0177270 A1 | 6/2016 | Takebe et al. |
| 2016/0184387 A1 | 6/2016 | Charmot et al. |
| 2016/0206664 A1 | 7/2016 | Sokal et al. |
| 2016/0237400 A1 | 8/2016 | Xian |
| 2016/0237401 A1 | 8/2016 | Vallier et al. |
| 2016/0237409 A1 | 8/2016 | Little et al. |
| 2016/0245653 A1 | 8/2016 | Park et al. |
| 2016/0256672 A1 | 9/2016 | Arumugaswami et al. |
| 2016/0257937 A1 | 9/2016 | Wauthier et al. |
| 2016/0263098 A1 | 9/2016 | Mantzoros |
| 2016/0289635 A1 | 10/2016 | Sasai et al. |
| 2016/0296599 A1 | 10/2016 | Dinh et al. |
| 2016/0312181 A1 | 10/2016 | Freed et al. |
| 2016/0312190 A1 | 10/2016 | Ghaedi et al. |
| 2016/0312191 A1 | 10/2016 | Spence et al. |
| 2016/0319240 A1 | 11/2016 | Chan et al. |
| 2016/0340645 A1 | 11/2016 | D'Amour et al. |
| 2016/0340749 A1 | 11/2016 | Stelzer et al. |
| 2016/0354408 A1 | 12/2016 | Hariri et al. |
| 2016/0361466 A1 | 12/2016 | Yanagawa et al. |
| 2016/0376557 A1 | 12/2016 | Dubart Kupperschmitt et al. |
| 2017/0002330 A1 | 1/2017 | Vunjak-Novakovic et al. |
| 2017/0027994 A1 | 2/2017 | Kotton et al. |
| 2017/0035661 A1 | 2/2017 | Kyrkanides et al. |
| 2017/0035784 A1 | 2/2017 | Lancaster et al. |
| 2017/0037043 A1 | 2/2017 | Liu |
| 2017/0067014 A1 | 3/2017 | Takebe et al. |
| 2017/0101628 A1 | 4/2017 | Ingber et al. |
| 2017/0107469 A1 | 4/2017 | Costa et al. |
| 2017/0107483 A1 | 4/2017 | Pendergraft et al. |
| 2017/0107498 A1 | 4/2017 | Sareen et al. |
| 2017/0128625 A1 | 5/2017 | Bhatia et al. |
| 2017/0151049 A1 | 6/2017 | La Francesca et al. |
| 2017/0152486 A1 | 6/2017 | Shen et al. |
| 2017/0152528 A1 | 6/2017 | Zhang |
| 2017/0184569 A1 | 6/2017 | Keshavarzian et al. |
| 2017/0191030 A1 | 7/2017 | Huch Ortega et al. |
| 2017/0198261 A1 | 7/2017 | Sabaawy et al. |
| 2017/0204375 A1 | 7/2017 | Accili et al. |
| 2017/0205396 A1 | 7/2017 | Izpisua Belmonte et al. |
| 2017/0205398 A1 | 7/2017 | Bruce et al. |
| 2017/0239262 A1 | 8/2017 | Lefebvre |
| 2017/0240863 A1 | 8/2017 | Sokal et al. |
| 2017/0240866 A1 | 8/2017 | Wells et al. |
| 2017/0240964 A1 | 8/2017 | Leung et al. |
| 2017/0258772 A1 | 9/2017 | Sabatini et al. |
| 2017/0260501 A1 | 9/2017 | Semechkin et al. |
| 2017/0266145 A1 | 9/2017 | Nahmias et al. |
| 2017/0267970 A1 | 9/2017 | Gupta et al. |
| 2017/0267977 A1 | 9/2017 | Huang et al. |
| 2017/0275592 A1 | 9/2017 | Sachs et al. |
| 2017/0285002 A1 | 10/2017 | Taniguchi et al. |
| 2017/0292116 A1 | 10/2017 | Wells et al. |
| 2017/0296621 A1 | 10/2017 | Sansonetti et al. |
| 2017/0304294 A1 | 10/2017 | Wu et al. |
| 2017/0304369 A1 | 10/2017 | Ang et al. |
| 2017/0319548 A1 | 11/2017 | Lefebvre |
| 2017/0321188 A1 | 11/2017 | Viczian et al. |
| 2017/0321191 A1 | 11/2017 | Kojima |
| 2017/0335283 A1 | 11/2017 | Wang et al. |
| 2017/0342385 A1 | 11/2017 | Sachs et al. |
| 2017/0348433 A1 | 12/2017 | Kay et al. |
| 2017/0349659 A1 | 12/2017 | Garcia et al. |
| 2017/0349884 A1 | 12/2017 | Karp et al. |
| 2017/0360962 A1 | 12/2017 | Kay et al. |
| 2017/0362573 A1 | 12/2017 | Wells et al. |
| 2018/0021341 A1 | 1/2018 | Harriman et al. |
| 2018/0030409 A1 | 2/2018 | Lewis et al. |
| 2018/0042970 A1 | 2/2018 | Rossen et al. |
| 2018/0059119 A1 | 3/2018 | Takats et al. |
| 2018/0112187 A1 | 4/2018 | Smith et al. |
| 2018/0250410 A1 | 9/2018 | Borros Gomez et al. |
| 2019/0031992 A1 | 1/2019 | Kerns et al. |
| 2019/0078055 A1 | 3/2019 | Wells et al. |
| 2019/0153395 A1 | 5/2019 | Barrett et al. |
| 2019/0298775 A1 | 10/2019 | Takebe et al. |
| 2019/0314387 A1 | 10/2019 | Takebe et al. |
| 2019/0367882 A1 | 12/2019 | Wells et al. |
| 2020/0040309 A1 | 2/2020 | Takebe et al. |

FOREIGN PATENT DOCUMENTS

| | | |
|---|---|---|
| CN | 105985395 A | 10/2016 |
| EP | 2393917 A2 | 12/2011 |
| EP | 2393917 B1 | 4/2016 |
| EP | 3228306 A1 | 10/2017 |
| JP | 2003-521673 A | 7/2003 |
| JP | 2008-503203 A | 2/2008 |
| JP | 2008-505638 A | 2/2008 |
| JP | 2013-066414 A | 4/2013 |
| KR | 10-2006-0114355 A | 11/2006 |
| WO | WO 92/07615 | 5/1992 |
| WO | WO 98/21312 | 5/1998 |
| WO | WO 2003/082201 A2 | 10/2003 |
| WO | WO 2005/001072 A1 | 1/2005 |
| WO | WO 2005/081970 A2 | 9/2005 |
| WO | WO 2005/097974 A2 | 10/2005 |
| WO | WO 2005/113747 A2 | 12/2005 |
| WO | WO 2006/126236 A1 | 11/2006 |
| WO | WO 2008/075339 A2 | 6/2008 |
| WO | WO 2009/022907 A2 | 2/2009 |
| WO | WO-2009086596 A1 | 7/2009 |
| WO | WO 2009/146911 A2 | 12/2009 |
| WO | WO 2010/008905 A2 | 1/2010 |
| WO | WO 2010/090513 A2 | 8/2010 |
| WO | WO 2010/094694 A1 | 8/2010 |
| WO | WO 2010/127399 A1 | 11/2010 |
| WO | WO 2010/143747 A1 | 12/2010 |
| WO | WO-2011116930 A1 | 9/2011 |
| WO | WO 2011/139628 A1 | 11/2011 |
| WO | WO 2011/140441 A2 | 11/2011 |
| WO | WO 2012/014076 A2 | 2/2012 |
| WO | WO 2012/027474 A1 | 3/2012 |
| WO | WO 2012/089669 A1 | 7/2012 |
| WO | WO 2012/118799 A2 | 9/2012 |
| WO | WO 2012/154834 A1 | 11/2012 |
| WO | WO 2012/155110 A1 | 11/2012 |
| WO | WO 2012/166903 A1 | 12/2012 |
| WO | WO 2012/168930 A2 | 12/2012 |
| WO | WO 2012/178215 A1 | 12/2012 |
| WO | WO 2013/040087 A2 | 3/2013 |
| WO | WO 2013/067498 A1 | 5/2013 |
| WO | WO 2013/086486 A1 | 6/2013 |
| WO | WO 2013/086502 A1 | 6/2013 |
| WO | WO 2013/093812 A2 | 6/2013 |
| WO | WO 2013/096741 A2 | 6/2013 |
| WO | WO 2013/127921 A1 | 9/2013 |
| WO | WO 2013/155060 A1 | 10/2013 |
| WO | WO 2013/174794 A1 | 11/2013 |
| WO | WO 2013/192290 A1 | 12/2013 |

(56) References Cited

FOREIGN PATENT DOCUMENTS

| WO | WO 2014/013334 A2 | 1/2014 |
|---|---|---|
| WO | WO 2014/048637 A1 | 4/2014 |
| WO | WO 2014/053596 A1 | 4/2014 |
| WO | WO 2014/082096 A1 | 5/2014 |
| WO | WO 2014/090993 A1 | 6/2014 |
| WO | WO 2014/127170 A1 | 8/2014 |
| WO | WO 2014/151921 A1 | 9/2014 |
| WO | WO 2014/153230 A1 | 9/2014 |
| WO | WO 2014/153294 A1 | 9/2014 |
| WO | WO 2014/159356 A1 | 10/2014 |
| WO | WO 2014/173907 A1 | 10/2014 |
| WO | WO 2014/182885 A2 | 11/2014 |
| WO | WO 2014/197934 A1 | 12/2014 |
| WO | WO 2014/199622 A1 | 12/2014 |
| WO | WO 2015/021358 A2 | 2/2015 |
| WO | WO 2015/060790 A1 | 4/2015 |
| WO | WO 2015/075175 A1 | 5/2015 |
| WO | WO 2015/076388 A1 | 5/2015 |
| WO | WO 2015/108893 A1 | 7/2015 |
| WO | WO 2015/123183 A1 | 8/2015 |
| WO | WO 2015/129822 A1 | 9/2015 |
| WO | WO 2015/130919 A1 | 9/2015 |
| WO | WO 2015/135893 A1 | 9/2015 |
| WO | WO 2015/138032 A2 | 9/2015 |
| WO | WO 2015/152954 A1 | 10/2015 |
| WO | WO 2015/156929 A1 | 10/2015 |
| WO | WO 2015/157163 A1 | 10/2015 |
| WO | WO 2015/168022 A1 | 11/2015 |
| WO | WO 2015/0173425 A1 | 11/2015 |
| WO | WO 2015/183920 A2 | 12/2015 |
| WO | WO 2015/184273 A1 | 12/2015 |
| WO | WO 2015/184375 A2 | 12/2015 |
| WO | WO 2015/185714 A1 | 12/2015 |
| WO | WO 2015/196012 A1 | 12/2015 |
| WO | WO 2015/200901 A1 | 12/2015 |
| WO | WO 2016/011377 A1 | 1/2016 |
| WO | WO 2016/015158 A1 | 2/2016 |
| WO | WO 2016/030525 A1 | 3/2016 |
| WO | WO 2016/033163 A1 | 3/2016 |
| WO | WO 2016/057571 A1 | 4/2016 |
| WO | WO 2016/061464 A1 | 4/2016 |
| WO | WO-2016056999 A1 | 4/2016 |
| WO | WO 2016/073989 A2 | 5/2016 |
| WO | WO 2016/083612 A1 | 6/2016 |
| WO | WO 2016/083613 A2 | 6/2016 |
| WO | WO 2016/085765 A1 | 6/2016 |
| WO | WO 2016/094948 A1 | 6/2016 |
| WO | WO 2016/103002 A1 | 6/2016 |
| WO | WO 2016/103269 A1 | 6/2016 |
| WO | WO 2016/121512 A1 | 8/2016 |
| WO | WO 2016/114769 A1 | 9/2016 |
| WO | WO 2016/140716 A1 | 9/2016 |
| WO | WO 2016/141137 A1 | 9/2016 |
| WO | WO 2016/164413 A1 | 10/2016 |
| WO | WO 2016/168950 A1 | 10/2016 |
| WO | WO 2016/174604 A1 | 11/2016 |
| WO | WO 2016/176208 A1 | 11/2016 |
| WO | WO 2016/183143 A1 | 11/2016 |
| WO | WO 2016/193441 A2 | 12/2016 |
| WO | WO 2016/207621 A1 | 12/2016 |
| WO | WO 2016/210313 A1 | 12/2016 |
| WO | WO 2016/210416 A2 | 12/2016 |
| WO | WO 2017/009263 A1 | 1/2017 |
| WO | WO 2017/036533 A1 | 3/2017 |
| WO | WO 2017/037295 A1 | 3/2017 |
| WO | WO 2017/041041 A1 | 3/2017 |
| WO | WO 2017/048193 A1 | 3/2017 |
| WO | WO 2017/048322 A1 | 3/2017 |
| WO | WO 2017/049243 A1 | 3/2017 |
| WO | WO 2017/059171 A1 | 4/2017 |
| WO | WO 2017/060884 A1 | 4/2017 |
| WO | WO 2017/066507 A1 | 4/2017 |
| WO | WO 2017/066659 A1 | 4/2017 |
| WO | WO 2017/070007 A2 | 4/2017 |
| WO | WO 2017/070224 A1 | 4/2017 |
| WO | WO 2017/070471 A1 | 4/2017 |
| WO | WO 2017/070506 A1 | 4/2017 |
| WO | WO-2017070337 A1 | 4/2017 |
| WO | WO 2017/075389 A1 | 5/2017 |
| WO | WO 2017/077535 A1 | 5/2017 |
| WO | WO 2017/079632 A1 | 5/2017 |
| WO | WO 2017/083705 A1 | 5/2017 |
| WO | WO 2017/096192 A1 | 6/2017 |
| WO | WO 2017/096282 A1 | 6/2017 |
| WO | WO 2017/112901 A1 | 6/2017 |
| WO | WO 2017/115982 A1 | 7/2017 |
| WO | WO 2017/117333 A1 | 7/2017 |
| WO | WO 2017/117547 A1 | 7/2017 |
| WO | WO 2017/117571 A1 | 7/2017 |
| WO | WO 2017/120543 A1 | 7/2017 |
| WO | WO 2017/121754 A1 | 7/2017 |
| WO | WO 2017/123791 A1 | 7/2017 |
| WO | WO 2017/136462 A2 | 8/2017 |
| WO | WO 2017/136479 A1 | 8/2017 |
| WO | WO 2017/139455 A1 | 8/2017 |
| WO | WO 2017/139638 A1 | 8/2017 |
| WO | WO 2017/142069 A1 | 8/2017 |
| WO | WO 2017/143100 A1 | 8/2017 |
| WO | WO 2017/149025 A1 | 9/2017 |
| WO | WO 2017/153992 A1 | 9/2017 |
| WO | WO 2017/160234 A1 | 9/2017 |
| WO | WO 2017/160671 A1 | 9/2017 |
| WO | WO 2017/172638 A1 | 10/2017 |
| WO | WO 2017/174609 A1 | 10/2017 |
| WO | WO 2017/176810 A1 | 10/2017 |
| WO | WO 2017/184586 A1 | 10/2017 |
| WO | WO-2017174609 A1 | 10/2017 |
| WO | WO-2017175876 A1 | 10/2017 |
| WO | WO 2017/192997 A1 | 11/2017 |
| WO | WO 2017/205511 A1 | 11/2017 |
| WO | WO 2017/218287 A1 | 12/2017 |
| WO | WO 2017/220586 A1 | 12/2017 |
| WO | WO 2018/011558 A1 | 1/2018 |
| WO | WO 2018/019704 A1 | 2/2018 |
| WO | WO 2018/026947 A1 | 2/2018 |
| WO | WO 2018/027023 A1 | 2/2018 |
| WO | WO 2018/027112 A1 | 2/2018 |
| WO | WO 2018/035574 A1 | 3/2018 |
| WO | WO 2018/038042 A1 | 3/2018 |
| WO | WO 2018/044685 A1 | 3/2018 |
| WO | WO 2018/044885 A1 | 3/2018 |
| WO | WO 2018/044937 A2 | 3/2018 |
| WO | WO 2018/044940 A1 | 3/2018 |
| WO | WO 2018/085615 A1 | 5/2018 |
| WO | WO 2018/094522 A1 | 5/2018 |
| WO | WO 2018/106628 A1 | 6/2018 |
| WO | WO-2018115852 A1 | 6/2018 |
| WO | WO 2018/197544 A1 | 11/2018 |
| WO | WO 2019/074793 A1 | 4/2019 |

OTHER PUBLICATIONS

Burns, A.J., et al., "In ovo transplantation of enteric nervous system precursors from vagal to sacral neural crest results in extensive hindgut colonisation," Development, 2002, 129:2785-2796, 12 pgs.

Cincinnati Children's Hospital Medical Center, "Scientists grow human esophagus in lab: Tiny organoids enable personalized disease diagnosis, regenerative therapies," CCHMC Public Press Release, Sep. 20, 2018, 2 pgs.

Kawaguchi, J., et al., "Isolation and propagation of enteric neural crest progenitor cells from mouse embryonic stem cells and embryos," Development, 2010, 137:693-704, 12 pgs.

Keung, A.J., et al., "Presentation Counts: Microenvironmental Regulation of Stem Cells by Biophysical and Material Cues," Annu. Rev. Cell Dev. Biol., 2010, 26:533-556, 26 pgs.

Merker, S.R., et al., "Gastrointestinal organoids: How they gut it out," Developmental Biology, 2016, 420:239-250, 12 pgs.

Mosher, J.T., et al., "Intrinsic differences among spatially distinct neural crest stem cells in terms of migratory properties, fate-determination, and ability to colonize the enteric nervous system," Dev. Biol., Mar. 2007, 303(1):1-15, 29 pgs.

(56) References Cited

OTHER PUBLICATIONS

Mullin, E., "Tiny Human Esophagus Grown in the Lab—Here's Why: Miniature versions of the organ that guides food to the stomach could help scientists treat a variety of medical ailments," National Geographic, Sep. 20, 2018, downloaded from https://www.nationalgeographic.com/science/2018/09/news-human-esophagus-grown-lab-stem-cells-cancer-health.html, 5 pgs.
Sandoiu, A., "Scientists create human esophagus in stem cell first," Medical News Today, Sep. 21, 2018, downloaded from https://www.medicalnewstoday.com/articles/323118.php, 4 pgs.
U.S. Appl. No. 16/084,599, filed Sep. 13, 2018.
U.S. Appl. No. 62/332,194, filed May 5, 2016.
Ader. M., et al., "Modeling human development in 3D culture," Current Opinion in Cell Biology, 2014, 31:23-28, 6 pgs.
Adorini, L., et al., "Farnesoid X receptor targeting to treat nonalcoholic steatohepatitis," Drug Discovery Today, Sep. 2012, 17(17/18):988-997, 10 pgs.
Agopian, V.G., et al., "Intestinal Stem Cell Organoid Transplantation Generates Neomucosa in Dogs," Journal of Gastrointestinal Surgery, Jan. 23, 2009, 13(5):971-982, XP055241418, 12 pgs.
Alessi, D.R., et al., "LKB1-Dependent Signaling Pathways," Annu. Rev. Biochem., 2006, 75:137-63, 30 pgs.
Altman, G.H., et al., "Cell differentiation by mechanical stress," The FASEB Journal, 2001, 16(2):270-272, 13 pgs.
Ameri, J., et al., "FGF2 Specifies hESC-Derived Definitive Endoderm into Foregut/Midgut Cell Lineages in a Concentration-Dependent Manner," Stem Cells, ePUB Nov. 3, 2009, 28(1):45-56, 12 pgs.
Amieva, M.R., et al. "*Helicobacter pylori* enter and survive within multivesicular vacuoles of epithelial cells," Cell. Microbiol., 2002, 4(10):677-690, 15 pgs.
Anderson, G., et al., "Loss of enteric dopaminergic neurons and associated changes in colon motility in an MPTP mouse model of Parkinson's disease," Exp Neurol, Sep. 2007, 207:4-12, 16 pgs.
Andrews, P.W., et al., "Embryonic stem (ES) cells and embryonal carcinoma (EC) cells: opposite sides of the same coin," Biochem Soc Trans, 2005, 33(part 6):1526-1530, 5 pgs.
Ang, S-L, et al., "The formation and maintenance of the definitive endoderm lineage in the mouse: involvement of HNF3/forkhead proteins," Development, 1993, 119:1301-1315, 15 pgs.
Anlauf, M., et al., "Chemical coding of the human gastrointestinal nervous system: cholinergic VIPergic, and catecholaminergic phenotypes," The Journal of Comparative Neurology, 2003, 459:90-111, 22 pgs.
Arora, N., et al., "A process engineering approach to increase organoid yield," Development, 2017, 144:1128-1136, 9 pgs.
Asai, A., et al., "Paracrine signals regulate human liver organoid maturation from induced pluripotent stem cells," Development, 2017, 144:1056-1064, 9 pgs.
Aurora, M., et al., "hPSC-derived lung and intestinal organoids as models of human fetal tissue," Developmental Biology, 2016, 420:230-238, 9 pgs.
Avansino, J.R., et al., "Orthotopic transplantation of intestinal mucosal organiods in rodents," Surgery, Sep. 2006, 140(3):423-434, XP005610494, 12 pgs.
Baetge, G., et al., "Transient catecholaminergic (TC) cells in the vagus nerves and bowel of fetal mice: relationship to the development of enteric neurons," Developmental Biology, 1989, 132:189-211, 23 pgs.
Bajpai, R., et al., "CHD7 cooperates with PBAF to control multipotent neural crest formation," Nature, Feb. 18, 2010, 463:958-962, 7 pgs.
Bansal, D., et al., "An ex-vivo human intestinal model to study *Entamoeba histolytica* Pathogenesis," PLoS Neglected Tropical Diseases, Nov. 2009, 3(11):e551.
Baptista, P.M., et al., "The Use of Whole Organ Decellularization for the Generation of a Vascularized Liver Organoid," Hepatology, 2011, 53(2):604-617, 14 pgs.
Barker, N., et al., "Lgr5$^{+ve}$ Stem Cells Drive Self-Renewal in the Stomach and Build Long-Lived Gastric Units In Vitro," Cell Stem Cell, 2010, 6:25-36, 12 pgs.

Barker, N., et al., "Tissue-Resident Adult Stem Cell Populations of Rapidly Self-Renewing Organs," Cell Stem Cell, Dec. 2010, 7:656-670, 15 pgs.
Bartfeld, S., et al., "Stem cell-derived organoids and their application for medical research and patient treatment," J Mol Med, 2017, 95:729-738, 10 pgs.
Bastide, P., et al. "Sox9 regulates cell proliferation and is required for Paneth cell differentiation in the intestinal epithelium," JCB, 2007, 178(4), pp. 635-648, 14 pgs.
Baumann, K., "Colonic organoids for drug testing and colorectal disease modelling," Nature Reviews Molecular Cell Biology, Jul. 2017, 1 pg.
Beck, F., et al., "Expression of Cdx-2 in the mouse embryo and placenta: possible tole in patterning of the extra-embroyonic membranes," Dev Dyn, 1995, 204:219-227.
Bergner, A.J., et al., "Birthdating of myenteric neuron subtypes in the small intestine of the mouse," The Journal of Comparative Neurology, 2014, 522:514-527, 14 pgs.
Bitar, K.N., et al., "Intestinal Tissue Engineering: Current Concepts and Future Vision of Regenerative Medicine in the Gut," Neurogastroenterol Motil., Jan. 2012, 24(1):7-19, 20 pgs.
Blaugrund, E., et al., "Distinct subpopulations of enteric neuronal progenitors defined by time of development, sympathoadrenal lineage markers and Mash-1-dependence," Development 122, 1996, 309-320, 12 pgs.
Bohorquez, D.V., et al., "An Enteroendocrine Cell—Enteric Glia Connection Revealed by 3D Electron Microscopy," PLOS One, Feb. 2014, 9(2):e89881, 13 pgs.
Brevini, T.A.L., et al., "No shortcuts to pig embryonic stem cells," Theriogenology, 2010, 74:544-550, 7 pgs.
Bruens, L., et al., "Expanding the Tissue Toolbox: Deriving Colon Tissue from Human Pluripotent Stem Cells," Cell Stem Cell, Jul. 2017, 21(1):3-5, 3 pgs.
Brugmann, S.A., et al., "Building additional complexity to in vitro-derived intestinal tissues," Stem Cell Research & Therapy, 2013, 4(Suppl 1):S1, 5 pgs.
Burns, A.J., et al., "Neural stem cell therapies for enteric nervous system disorders," Nature Reviews/Gastroenterology & Hepatology, May 2014, 11:317-328, 12 pgs.
Cabezas, J., et al., "Nonalcoholic Fatty Liver Disease: A Pathological View," Liver Biopsy—Indications, Procedures, Results, Chapter 8, InTech, 2012, pp. 161-188, 29 pgs.
Campbell, F.C., et al., "Transplantation of cultured small bowel enterocytes," Gut, 1993, 34:1153-1155, 4 pgs.
Cao, L., et al., "Development of Intestinal Organoids as Tissue Surrogates: Cell Composition and the Epigenetic Control of Differentiation," Molecular Carcinogenesis, 2015, 54:189-202, 14 pgs.
Chen, C., et al., "Pdx1 inactivation restricted to the intestinal epithelium in mice alters duodenal gene expression in enterocytes and enteroendocrine cells," Am. J. Physiol. Gastrointest. Liver Pyshiol., 2009, 297:G1126-G1137, 12 pgs.
Chen, T-W., et al., "Ultrasensitive fluorescent proteins for imaging neuronal activity," Nature, Jul. 18, 2013, 499:295-300, 8 pgs.
Cheng, X., et al., "Self-renewing endodermal progenitor lines generated from human pluripotent stem cells," Cell Stem Cell, Apr. 6, 2012, 10:371-384, 14 pgs.
Churin, Y., et al., "*Helicobacter pylori* CagA protein targets the c-Met receptor and enhances the motogenic response," J. Cell Biol., 2003, 161:249-255, 7 pgs.
Cieslar-Pobuda, A., et al., The expression pattern of PFKFB3 enzyme distinguishes between induced-pluripotent stem cells and cancer stem cells, Oncotarget, 6(30):29753-29770, 18 pgs.
Clevers, H., "Modeling Development and Disease with Organoids," Cell, Jun. 2016, 165:1586-1597, 12 pgs.
Coghlan, M.P., et al., "Selective small molecule inhibitors of glycogen synthase kinase-3 modulate glycogen metabolism and gene transcription," Chem. Biol., 2000, 7(10):793-803, 11 pgs.
Correia, C., et al., "Combining Hypoxia and Bioreactor Hydrodynamics Boosts Induced Pluripotent Stem Cell Differentiation Towards Cardiomyocytes," Stem Cell Rev and Rep, 2014, 10:786-801, 16 pgs.

(56) References Cited

OTHER PUBLICATIONS

Costa, M., et al., "A method for genetic modification of human embryonic stem cells using electroporation," Nature Protocols, Apr. 5, 2007, 2:792-796, 5 pgs.

Couzin, J., "Small RNAs Make Big Splash," Science, 2002, 298:2296-2297, 2 pgs.

Covacci, A., et al., "Molecular characterization of the 128-kDa immunodominant antigen of *Helicobacter pylori* associated with cytotoxicity and duodenal ulcer," Proc Natl Acad Sci USA, Jun. 1993, 90:5791-5795, 5 pgs.

Curchoe, C.L., et al., "Early acquisition of neural crest competence during hESCs neuralization," PloS One, Nov. 2010, 5:1-17, 17 pgs.

D'Amour, K.A., et al., "Efficient differentiation of human embryonic stem cells to definitive endoderm," Nature Biotechnology, 2005, 23:1534-1541, 9 pgs.

D'Amour, K.A., et al., "Production of pancreatic hormone-expressing endocrine cells from human embryonic stem cells," Nat Biotechnol, 2006, 24:1392-1401, 10 pgs.

Dahl, A., et al., "Translational Regenerative Medicine—Hepatic Systems," Chapter 34, Clinical Aspects of Regenerative Medicine, eds. A. Atala, M.D. and J. Allickson, PhD, Elsevier, Inc, 2015, pp. 469-484, 16 pgs.

Date, S., et al., "Mini-Gut Organoids: Reconstitution of the Stem Cell Niche," Annual Review of Cell and Developmental Biology, Nov. 2015, 31:269-289.

Davenport, C., et al., "Anterior-Posterior Patterning of Definitive Endoderm Generated from Human Embryonic Stem Cells Depends on the Differential Signaling of Retinoic Acid, Wnt-, and BMP-Signaling," Stem Cells, 2016, 34:2635-2647, 13 pgs.

De Santa Barbara, P., et al., "Development and differentiation of the intestinal epithelium," Cell Mol Life Sci, 2003, 60(7):1322-1332, 12 pgs.

Dedhia, P.H., et al., "Organoid Models of Human Gastrointestinal Development and Disease," Gastroenterology, 2016, 150:1098-1112, 15 pgs.

Dekaney, C.M., et al., "Expansion of intestinal stem cells associated with long-term adaptation following ileocecal resection in mice," Am J Physiol Gastrointest Liver Physiol, Sep. 13, 2007, 293:G1013-G1022, 10 pgs.

Denham, M., et al., "Multipotent caudal neural progenitors derived from human pluripotent stem cells that give rise to lineages of the central and peripheral nervous system," Stem Cells, Mar. 5, 2015, 33:1759-1770, 12 pgs.

Dessimoz, J., et al., "FGF signaling is necessary for establishing gut tube domains along the anterior-posterior axis in vivo," Mech Dev, 2006, 123:42-55, 14 pgs.

Discher, D.E., et al., "Growth Factors, Matrices, and Forces Combine and Control Stem Cells," Science, Jun. 2009, 324:1673-1677, 5 pgs.

Eberhard, J., et al., "A cohort study of the prognostic and treatment predictive value of SATB2 expression in colorectal cancer," British Journal of Cancer, 2012, 106:931-938, 8 pgs.

Eicher, A.K., et al., "Translating Developmental Principles to Generate Human Gastric Organoids," Cellular and Molecular Gastroenterology and Hepatology, 2018, 5(3):353-363, 11 pgs.

Elbashir, S.M., et al., "Functional anatomy of siRNAs for mediating efficient RNAi in *Drosophila melanogaster* embryo lysate," EMBO J., 2001, 20(23):6877-6888, 12 pgs.

Evans, M.J., et al., "Establishment in culture of pluripotent cells from mouse embryos," Nature, 1981, 292:154-156, 3 pgs.

Ezashi, T., et al., "Low $O_2$ tensions and the prevention of differentiation of hES cells," PNAS, Mar. 2005, 102(13):4783-4788, 6 pgs.

Fatehullah, A., et al., "Organoids as an in vitro model of human development and disease," Nature Cell Biology, Mar. 2106, 18(3):246-254, 9 pgs.

Finkbeiner, S.R., et al., "A Gutsy Task: Generating Intestinal Tissue from Human Pluripotent Stem Cells," Dig Dis Sci, 2013, 58:1176-1184, 9 pgs.

Finkbeiner, S.R., et al., "Stem Cell-Derived Human Intestinal Organoids as an Infection Model for Rotaviruses," mBio, Jul./Aug. 2012, 3(4):e00159-12, 6 pgs.

Fordham, R.P., et al., "Transplantation of expanded fetal intestinal progenitors contributes to colon regeneration after injury," Cell Stem Cell, Dec. 5, 2013, 13:734-744, 11 pgs.

Fu, M., et al., "Embryonic development of the ganglion plexuses and the concentric layer structure of human gut: a topographical study," Anatomy and Embryology, Feb. 27, 2004, 208:33-41, 10 pgs.

Fu, M., et al., "HOXB5 expression is spatially and temporarily regulated in human embryonic gut during neural crest cell colonization and differentiation of enteric neuroblasts," Developmental Dynamics, 2003, 228:1-10, 10 pgs.

Furness, J.B., "The enteric nervous system and neurogastroenterology," Nature Reviews/Gastroenterology & Hepatology, May 2012, 9:286-294, 9 pgs.

Gessner, R.C., et al., "Functional ultrasound imaging for assessment of extracellular matrix scaffolds used for liver organoid formation," Biomaterials, 2013, 34:9341-9351, 11 pgs.

Gori, M., et al., "Investigating nonalcoholic Fatty Liver Disease in a Liver-on-a-Chip Microfluidic Device," PLOS One, Jul. 2016, 11(7):e0159729, 15 pgs.

Gouon-Evans, V., et al., "BMP-4 is required for hepatic specification of mouse embryonic stem cell-derived definitive endoderm," Nature Biotechnology, Nov. 2006, 24(11):1402-1411, 10 pgs.

Gracz, A.D., et al., "Brief report: CD24 and CD44 mark human intestinal epithelial cell populations with characteristics of active and facultative stem cells," Stem Cells, Apr. 4, 2013, 31:2024-2030, 7 pgs.

Gracz, A.D., et al., "Sox9 Expression Marks a Subset of CD24-expressing Small Intestinve Epithelial Stem Cells the Form Organoids in vitro," Am J Physiol Gastrointest Liver Physiol, 2010, 298:G590-600.

Gradwohl, G., et al., "neurogenin3 is required for the development of the four endocrine cell lineages of the pancreas," Proc Natl Acad Sci USA, 2000, 97:1607-1611, 5 pgs.

Green, M.D., et al., "Generation of anterior foregut endoderm from human embryonic and induced pluripotent stem cells," Nature Biotechnology, Mar. 2011, 29(3):267-272, 7 pgs.

Gregorieff, A., et al., "Wnt signaling in the intestinal epithelium: from endoderm to cancer," Genes & Dev., 2005, 19:877-890, 15 pgs.

Groneberg, D.A., et al., "Intestinal peptide transport: ex vivo uptake studies and localization of peptide carrier PEPT1," Am J Physiol Gastrointest Liver Physiol, Sep. 2001, 281:G697-G704, 8 pgs.

Grosse, A.S., et al., "Cell dynamics in fetal intestinal epithelium: implications for intestinal growth and morphogenesis," Development, 2011, 138:4423-4432, 10 pgs.

Guilak, F., et al., "Control of Stem Cell Fate by Physical Interactions with the Extracellular Matrix," Cell Stem Cell, Jul. 2009, 5:17-26, 10 pgs.

Han, M-E., et al., "Gastric stem cells and gastric cancer stem cells," Anatomy & Cell Biology, 2013, 46:8-18, 11 pgs.

Hannon, G.J., "RNA interference," Nature, 2002, 418:244-251, 8 pgs.

Hannon, N.R.F., et al., "Generation of Multipotent Foregut Stem Cells from Human Pluripotent Stem Cells," Stem Cell Reports, Oct. 2013, 1:293-306, 14 pgs.

Hao, M.M., et al., "Development of enteric neuron diversity," J. Cell. Mol. Med., 2009 13:1193-1210, 18 pgs.

Hardy, T., et al., "Nonalcoholic fatty liver disease: new treatments," Curr Opin Gastroenterol, May 2015, 31(3):175-183, 9 pgs.

Haveri, H., et al., "Transcription factors GATA-4 and GATA-6 in normal and neoplastic human gastrointestinal mucosa," BMC Gastroenterlology, 2008, 8:9.

Hockemeyer, D., et al., "Genetic engineering of human ES and iPS cells using TALE nucleases," Nat Biotechnol., 2012, 29:731-734, 8 pgs.

Howell, J.C., et al., "Generating intestinal tissue from stem cells: potential for research and therapy," Regen Med., 6(6):743-755, 22 pgs.

(56) References Cited

OTHER PUBLICATIONS

Huch, M., et al., "Lgr5+ liver stem cells, hepatic organoids and regenerative medicine," Regen. Med., 2013, 8(4):385-387, 3 pgs.

Huch, M., et al., "Modeling mouse and human development using organoid cultures," Development, 2015, 142:3113-3125, 13 pgs.

Huebsch, N., et al., "Automated Video-based analysis of contractility and calcium flux in human-induced pluripotent stem cell-derived cardiomyocytes cultured over different spatial scales," Tissue Engineering: Part C, 2015, 21:467-479, 15 pgs.

Hutvagner, G., et al., "A microRNA in a Multiple-Turnover RNAi Enzyme Complex," Science, Sep. 20, 2002, 297:2056-2060, 6 pgs.

Jenny, M., et al., "Neurogenin3 is differentially required for endocrine cell fate specification in the intestinal and gastric epithelium," EMBO J, 2002, 21(23):6338-6347, 10 pgs.

Johannesson, M., et al., "FGF4 and Retinoic Acid Direct Differentiation of hESCs into PDX1-Expressing Foregut Endoderm in a Time- and Concentration-Dependent Manner," PLoS One, Mar. 2009, 4(3):1-13, 13 pgs.

Johansson, K.A., et al., "Temporal Control of Neurogenin3 Activity in Pancreas Progenitors Reveals Competence Windows for the Generation of Different Endocrine Cell Types," Dev Cell, 2007, 12:457-465, 9 pgs.

Johnson, L.R., et al., "Stimulation of rat oxyntic gland mucosal growth by epidermal growth factor," Am. J. Physiol., 1980, 238:G45-49, 5 pgs.

Jung, P., et al., "Isolation and in vitro expansion of human colonic stem cells," Nature Medicine, Oct. 2011, 17:1225-1227, 3 pgs.

Juno, R.J., et al., "A serum factor after intestinal resection stimulates epidermal growth factor receptor signaling and proliferation in intestinal epithelial cells," Surgery, Aug. 2002, 132:377-383, 7 pgs.

Juno, R.J., et al., "A serum factor(s) after small bowel resection induces intestinal epithelial cell proliferation: effects of timing, site, and extent of resection," Journal of Pediatric Surgery, Jun. 2003, 38:868-874, 7 pgs.

Kabouridis, P.S., et al., "Microbiota controls the homeostasis of glial cells in the gut lamina propria," Neuron, Jan. 21, 2015, 85:289-295, 8 pgs.

Kaji, K., et al., "Virus-free induction of pluripotency and subsequent excision of reprogramming factors," Nature, Apr. 2009, 458:771-775, 6 pgs.

Katoh, M., "WNT Signaling in Stem Cell Biology and Regenerative Medicine," Current Drug Targets, 2008, 9(7):565-570, 6 pgs.

Kawaguchi, Y., et al., "The role of the transcriptional regulator Ptf1a in converting intestinal to pancreatic progenitors," Nat Genet, 2002, 32: 128-134, 7 pgs.

Kim, T-H., et al., "Stomach development, stem cells and disease," Development, 2016, 143:554-565, 12 pgs.

Klimanskaya, I., et al., "Human embryonic stem cells derived without feeder cells," Lancet, 2005, 365:1636-1641, 6 pgs.

Koike, M., et al., "Effects of mechanical strain on proliferation and differentiation of bone marrow stromal cell line ST2," J Bone Miner Metab, 2005, 23:219-225, 7 pgs.

Kolahchi, A.R., et al., "Microfluidic-Bases Multi-Organ Platforms for Drug Discovery," Micromachines, 2016, 7(162):1-33, 33 pgs.

Koo, B-K, et al., "Controlled gene expression in primary Lgr5 organoid cultures," Nature Methods, Jan. 1, 2012, 9(1):81-83, XP055225249, 5 pgs.

Kosinski, C., et al., "Indian hedgehog regulates intestinal stem cell fate through epithelial-mesenchymal interactions during development," Gastroenterology, Sep. 2010, 139:893-903, 17 pgs.

Kostrzewski, T., et al., "Three-dimensional perfused human in vitro model of non-alcoholic fatty liver disease," World J Gastroenterol, 2017, 23(2):204-215, 13 pgs.

Kovalenko, P.L., et al., "The correlation between the expression of differentiation markers in rat small intestinal mucosa and the transcript levels of schlafen 3," JAMA Surg., Sep. 4, 2013, 148:1013-1019, 7 pgs.

Kretzschmar, K., et al., "Organoids: Modeling Development and the Stem Cell Niche in a Dish," Developmental Cell, Sep. 2016, 38:590-600, 11 pgs.

Kroon, E., et al., "Pancreatic endoderm derived from human embryonic stem cells generates glucose-responsive insulin secreting cells in vivo," Nat Biotechnol, 2008, 26(4):443-52.

Kubo, A., et al., "Development of definitive endoderm from embryonic stem cells in culture," Development, 2004, 131:1651-1662, 12 pgs.

Kudoh, T., et al., "Distinct roles for Fgf, Wnt and retinoic acid in posteriorizing the neural ectoderm," Development, 2002, 129:4335-4346, 12 pgs.

Kumar, M., et al., "Signals from lateral plate mesoderm instruct endoderm toward a pancreatic fate," Dev Biol, 2003, 259:109-122, 14 pgs.

Kuratnik, A., et al., "Intestinal organoids as tissue surrogates for toxicological and pharmacological studies," Biochemical Pharmacology, 2013, 85:1721-1726, 6 pgs.

Lahar, N., et al., "Intestinal subepithelial myofibroblasts support in vitro and in vivo growth of human small intestinal epithelium," PLoS One, Nov. 2011, 6:e26898, 9 pgs.

Lambert, P.F., et al., "Using an immortalized cell line to study the HPV life cycle in organotypic 'raft' cultures," Methods in Molecular Medicine, 2005, 119:141-155.

Lancaster, M.A., et al., "Organogenesis in a dish: modeling development and disease using organoid technologies," Science, Jul. 18, 2014, 345:283 & 1247125-1-9, 11 pgs.

Lavial, F., et al., "Chicken embryonic stem cells as a non-mammalian embryonic stem cell model," Develop. Growth Diff., 2010, 52:101-114, 14 pgs.

Le Douarin, N.M., et al., "Neural crest cell plasticity and its limits," Development 131, 2004, 4637-4650, 14 pgs.

Lee, C.S., et al., "Neurogenin 3 is essential for the proper specification of gastric enteroendocrine cells and the maintenance of gastric epithelial cell identity," Genes Dev, 2002, 16:1488-1497, 11 pgs.

Lee, G., et al., "Isolation and directed differentiation of neural crest stem cells derived from human embryonic stem cells," Nature Biotechnology, Dec. 2007, 25:1468-1475, 9 pgs.

Levin, D.E., et al., "Human tissue-engineered small intestine forms from postnatal progenitor cells," Journal of Pediatric Surgery, 2013, 48:129-137, 9 pgs.

Li, Y., et al., "In Vitro organogenesis from pluripotent stem cells," Organogenesis, Jun. 2014, 10(2):159-163, 5 pgs.

Li, Z., et al., "SATB2 is a sensitive marker for lower gastrointestinal well-differentiated neuroendocrine tumors," Int J Clin Exp Pathol, 2015, 8(6):7072-7082, 11 pgs.

Lin, C., et al., "The application of engineered liver tissues for novel drug discovery," Expert Opinion on Drug Discovery, 2015, 10(5):519-540

Lindley, R.M., et al., "Human and Mouse Enteric Nervous System Neurosphere Transplants Regulate the Function of Aganglionic Embryonic Distal Colon," Gastroenterology, Jul. 2008, 135(1):205-216, XP022823118, 18 pgs.

Liu, J., et al., "A Small-Molecule Agonist of the Wnt Signaling Pathway," Angew Chem Int Ed Engl., 2005, 44(13):1987-1990, 4 pgs.

Logan, C.Y., et al., "The Wnt Signaling Pathway in Development and Disease," Annu. Rev. Cell Dev. Biol., 2004, 20:781-810, 32 pgs.

Longmire, T.A., et al., "Efficient Derivation of Purified Lung and Thyroid Progenitors from Embryonic Stem Cells," Stem Cell, 2012, 10:398-411, 14 pgs.

López-Díaz, L., et al., "Intestinal Neurogenin 3 directs differentiation of a bipotential secretory progenitor to endocrine cell rather than goblet cell fate," Dev Biol. 2007, 309:298-305, 8 pgs.

Lu, Y., et al., "A Novel 3D Liver Organoid System for Elucidation of Hepatic Glucose Metabolism," Biotechnol Bioeng., Feb. 2012, 109(2):595-604, 21 pgs.

Ludwig, T.E., et al., "Derivation of human embryonic stem cells in defined conditions," Nat Biotechnol, 2006, 24:185-187, 3 pgs.

Ludwig, T.E., et al., "Feeder-independent culture of human embryonic stem cells," Nat Methods, 2006, 3:637-646, 10 pgs.

Lui, V.C., et al., "Perturbation of hoxb5 signaling in vagal neural crests down-regulates ret leading to intestinal hypo ganglionosis in mice," Gastroenterology, 2008, 134:1104-1115, 12 pgs.

(56) References Cited

OTHER PUBLICATIONS

Luo, X., et al., "Generation of endoderm lineages from pluripotent stem cells," Regenerative Medicine, 2017, 12(1):77-89, 13 pgs.

Mahe, M.M., et al., "Establishment of gastrointestinal epithelial organoids," Current Protocols in Mouse Biology, 2013, 3(4):217-240, XP002750112, 31 pgs.

Majumdar, A.P.N., "Postnatal Undernutrition: Effect of Epidermal Growth Factor on Growth and Function of the Gastrointestinal Tract in Rats," J. Pediatr. Gastroenterol. Nutr., 1984, 3:618-625, 8 pgs.

Martin, G.R., "Teratocarcinomas and mammalian embryogenesis," Science, 1980, 209:768-776, 9pgs.

Martín, M., et al., "Dorsal pancreas agenesis in retinoic acid-deficient Raldh2 mutant mice," Dev Biol., 2005, 284:399-411, 13 pgs.

McCauley, H.A., et al., "Pluripotent stem cell-derived organoids: using principles of developmental biology to grow human tissues in a dish," Development, 2017, 144:958-962, 5 pgs.

McCracken, K.W., "Mechanisms of endoderm patterning and directed differentiation of human stem cells into foregut tissues," Dissertation, Graduate School of the University of Cincinnati, Jun. 19, 2014, 185 pgs.

McCracken, K.W., et al., "Mechanisms of embryonic stomach development," Seminars in Cell & Development Biology, 2017, 66:36-42, 7 pgs.

McCracken, K.W., et al., "Generating human intestinal tissue from pluripotent stem cells in vitro," Nature Protocols, 2011, 6(12):1920-1928, 19 pgs.

McCracken, K.W., et al., "Modelling human development and disease in pluripotent stem-cell-derived gastric organoids," Nature, Oct. 29, 2014, 516(7531):400-404, XP055210509, 30 pgs.

McCracken, K.W., et al., "Wnt/β-catenin promotes gastric fundus specification in mice and humans," Nature, Jan. 2017, 541(7636):182-187, 31 pgs.

McKeown, S.J., et al., "Hirschsprung disease: a developmental disorder of the enteric nervous system," Wiley Interdisciplinary Reviews Developmental Biology, Jan./Feb. 2013, 2:113-129, 17 pgs.

McLin, V.A. et al., "The Role of the Visceral Mesoderm in the Development of the Gastrointestinal Tract," Gastroenterology, 2009, 136:2074-2091, 18 pgs.

McLin, V.A., et al., "Repression of Wnt/β-catenin signaling in the anterior endoderm is essential for liver and pancreas development," Development, 2007, 134:2207-2217, 11 pgs.

McManus, M.T., et al., "Gene Silencing in Mammals by Small Interfering RNAs," Nat. Rev. Genet., Oct. 2002, 3:737-747, 13 pgs.

Meerbrey, K.L., et al., "The pINDUCER lentiviral toolkit for inducible RNA interference in vitro and in vivo," Proc Natl Acad Sci USA, 2011, 108:3665-3670, 6 pgs.

Mica, Y., et al., "Modeling neural crest induction, melanocyte specification and disease-related pigmentation defects in hESCs and patient-specific iPSCs," Cell Reports, Apr. 25, 2013, 3:1140-1152, 27 pgs.

Micallef, S.J., et al., "Endocrine cells develop within pancreatic bud-like structures derived from mouse ES cells differentiated in response to BMP4 and retinoic acid," Stem Cell Research, 2007, 1:25-36, 12 pgs.

Mills, J.C., et al., "Gastric Epithelial Stem Cells," Gastroenterology, 2011, 140:412-424, 13 pgs.

Miyabayashi, T., et al., "Wnt/β-catenin/CBP signaling maintains long-term mutinc embryonic stem cell pluripotency," Proc Natl Acad Sci USA, 2007, 104(13):5668-5673, 6 pgs.

Molotkov, A., et al., "Retinoic Acid Generated by Raldh2 in Mesoderm is Required for Mouse Dorsal Endodermal Pancreas Development," Dev Dyn, 2005, 232:950-957, 8 pgs.

Mou, H., et al., "Generation of Multipotent Lung and Airway Progenitors from Mouse ESCs and Patient-Specific Cystic Fibrosis iPSCs," Stem Cell, 2012, 10:385-397, 13 pgs.

Mudaliar, S., et al., "Efficacy and Safety of the Farnesoid X Receptor Agonist Obeticholic Acid in Patients with Type 2 Diabetes and Nonalcoholic Fatty Liver Disease," Gastroenterology, 2013, 145:574-582, 10 pgs.

Munera, J.O., et al., "Differentiation of Human Pluripotent Stem Cells into Colonic Organoids via Transient Activation of BMP Signaling," Cell Stem Cell, Jul. 2017, 21(1):51-64.e6, 21 pgs.

Munera, J.O., et al., "Generation of Gastrointestinal Organoids from Human Pluripotent Stem Cells, Organ Regeneration,"In: Tsuji, T., (eds), Organ Regeneration. Methods in Molecular Biology, vo. 1597, Humana Press, New York, NY, 2017, 11 pgs.

Muñoz, M., et al., "Conventional pluripotency markers are unspecific for bovine embryonic-derived cell-lines," Theriogenology, 2008, 69:1159-1164, 6 pgs.

Nandivada, P., et al., "Treatment of Parenteral Nutrition-Associated Liver Disease: The Role of Lipid Emulsions," Advances in Nutrition, Reviews from ASN EB 2013 Symposia, pp. 711-717, 7 pgs.

Neiiendam, J.L., et al., "An NCAM-derived FGF-receptor agonist, the FGL-peptide, induces neurite outgrowth and neuronal survival in primary rat neurons," J. Neurochem., 2004, 91(4):920-935, 17 pgs.

Neuschwander-Tetri, B.A., et al., "Farnesoid X nuclear receptor ligand obeticholic acid for non-cirrhotic, non-alcoholic steatohepatitis (FLINT): a multicentre, randomised, placebo-controlled trial," Lancet, 2015, 385:956-965, 10 pgs.

Noguchi, T-a.K., et al., "Generation of stomach tissue from mouse embryonic stem cells," Nature Cell Biology, 2015, 17(8):984-993, XP055225165, 20 pgs.

Obermayr, F., et al., "Development and developmental disorders of the enteric nervous system," Nature Reviews/Gastroenterology & Hepatology, Jan. 2013, 10:43-57, 15 pgs.

Ogaki, S., et al., "Wnt and Notch Signals Guide Embryonic Stem Cell Differentiation into the Intestinal Lineages," Stem Cells, 2013, 31:1086-1096, 11 pgs.

Okita, K., et al., "An Efficient Nonviral Method to Generate Integration-Free Human-Induced Pluripotent Stem Cells from Cord Blood and Peripheral Blood Cells," Stem Cells, 2013, 31:458-466, 9 pgs.

Okita, K., et al., "Generation of Mouse Induced Pluripotent Stem Cells Without Viral Vectors," Science, 2008, 322(5903):949-953, 6 pgs.

Olbe, L., et al., "A Mechanism by Which *Helicobacter pylori* Infection of the antrum Contributes to the Development of Duodenal Ulcer," Gastroenterology, 2001, 110:1386-1394, 9 pgs.

Ootani, A. et al., "Sustained in vitro intestinal epithelial culture within a Wnt-dependent stem cell niche," Nat Med, 2009, 15:701-706, 14 pgs.

Paddison, P.J., et al., "RNA interference: the new somatic cell genetics?", Cancer Cell, 2002, 2:17-23, 7 pgs.

Pai, R., et al., "Deoxycholic Acid Activates β-Catenin Signaling Pathway and Increases Colon Cell Cancer Growth and Invasiveness," Mol Biol Cell., 2004, 15(5):2156-2163, 8 pgs.

Paris, D.B.B.P., et al., "Equine embryos and embryonic stem cells: Defining reliable markers of pluripotency," Theriogenology, 2010, 74:516-524, 9 pgs.

Park, H.R., et al., "Lipotoxicity of Palmaitic Acid on Neural Progenitor Cells and Hippocampal Neurogenesis," Toxicol Res, 2011, 27(2):103-110, 8 pgs.

Park, J.S., et al., "Differential Effects of Equiaxial and Uniaxial Strain on Mesenchymal Stem Cells," Biotechnology and Bioengineering, Nov. 2004, 88(3):359-368, 10 pgs.

Park, J.S., et al., "The effect of matrix stiffness on the differentiation of mesenhymal stem cells in response to TGF-β," Biomaterials, 2011, 32:3921-3930, 10 pgs.

Park, K.I., et al., "Acute injury directs the migration, proliferation, and differentiation of solid organ stem cells: Evidence for the effect of hypoxia-ischemia in the CNS on clonal "reporter" neural stem cells," Experimental Neurology, 2006, 199:159-178, 23 pgs.

Parkin, D.M., "The global health burden of infection-associated cancers in the year 2002," Int. J. Cancer, 2006, 118:3030-3044, 15 pgs.

(56) References Cited

OTHER PUBLICATIONS

Pastula, A., et al., "Three-Dimensional Gastrointestinal Organoid Culture in Combination with Nerves or Fibroblasts: A Method to Characterize the Gastrointestinal Stem Cell Niche," Stem Cells International, 2016, 16 pgs.
Peek, R.M., Jr., "*Helicobacter pylori* infection and disease: from humans to animal models," Dis Model Mech, 2008, 1:50-55, 6 pgs.
Peek, R.M., Jr., et al., "*Helicobacter pylori* cagA+ Strains and Dissociation of Gastric Epithelial Cell Proliferation From Apoptosis," J. Natl. Cancer Inst., 1997, 89:863-868, 7 pgs.
Pennisi, C.P., Ph.D., et al., "Uniaxial Cyclic Strain Drives Assembly and Differentiation of Skeletal Myocytes," Tissue Engineering: Part A, 2011, 17(19-20):2543-2550, 8 pgs.
Petitte, J.N., et al., "Avian pluripotent stem cells," Mech. of Develop., 2004, 121:1159-1168, 10 pgs.
Pompaiah, M., et al., "Gastric Organoids: An Emerging Model System to Study *Helicobacter pylori* Pathogenesis," Molecular Pathogenesis and Signal Transduction by *Helicobacter pylori*, Current Topics in Microbiology and Immunology, N. Tegtmeyer, et al., (eds.), 2017, pp. 149-168.
Pulikkot, S., "Establishment of a 3D Culture Model of Gastric Stem Cells Supporting Their Differentiation into Mucous Cells Using Microfibrous Polycaprolactone Scaffold," Dissertation, United Arab Emirates University, College of Medicine and Health Sciences, May 2015, 187 pgs. (4 parts: Part 1—58 pgs; Part 2—69 pgs; Part 3—31 pgs; Part 4—29 pgs.).
Qi, M-C., et al., "Mechanical strain induces osteogenic differentiation: Cbfa1 and Ets-1 expression in stretched rat mesenchymal stem cells," Int J Oral Maxillofac Surg, 2008, 37:453-458, 6 pgs.
Ramachandran, S.D., et al., "In Vitro Generation of Functional Liver Organoid-Like Structures Using Adult Human Cells," Plos One, Oct. 2015, 14 pgs.
Rankin, S.A., et al., "Timing is everything: Reiterative Wnt, BMP and RA signaling regulate developmental competence during endoderm organogenesis," Developmental Biology, Feb. 1, 2018, 434(1):121-132, 12 pgs.
Ray, K., "Engineering human intestinal organoids with a functional ENS," Nature Reviews Gastroenterology & Hepatology, Nov. 2016, 1 pg.
Reilly, G.C., et al., "Intrinsic extracellular matrix properties regulate stem cell differentiation," Journal of Biomechanics, 2010, 43:55-62, 8 pgs.
Rennert, K., et al., "A microfluidically perfused three dimensional human liver model," Biomaterials, 2015, 71:119-131, 13 pgs.
Richards, M., et al., "The Transcriptome Profile of Human Embryonic Stem Cells as Defined by SAGE," Stem Cells, 2004, 22:51-64, 14 pgs.
Rohrschneider, M.R., et al., "Polarity and cell fate specification in the control of *C. elegans* gastrulation," Dev. Dyn., 2009, 238(4):789-796, 15 pgs.
Saenz, J.B., et al., "Stomach growth in a dish: A protocol has been developed to grow structures that resemble the main part of the stomach in vitro from human embryonic stem cells—an advance that provides insights into stomach development," Nature, Jan. 2017, 541:160-161, 2 pgs.
Saffrey, M.J., "Cellular changes in the enteric nervous system during ageing," Developmental Biology, 2013, 382:344-355, 12 pgs.
Saha, S., et al., "Inhibition of Human Embryonic Stem Cell Differentiation by Medical Strain," Journal of Cellular Physiology, 2006, 206:126-137, 12 pgs.
Saito, M., et al., "Reconstruction of liver organoid using a bioreactor," World J Gastroenterol, Mar. 2006, 12(12):1881-1888, 8 pgs.
Sampaziotis, F., et al., "Potential of Human Induced Pluripotent Stem Cells in Studies of Liver Disease," Hepatology, Jul. 2015, 62(1):303-311, 9 pgs.
Sancho, E., et al., "Signaling Pathways in Intestinal Development and Cancer," Annu. Rev. Cell Dev. Biol., 2004, 20:695-723, 31 pgs.
Sasai, Y., "Next-Generation Regenerative Medicine: Organogenesis from Stem Cells in 3D Culture," Cell Stem Cell, May 2013, 12:520-530, 11 pgs.
Sasselli, V., et al., "The enteric nervous system," Developmental Biology, Jan. 2012, 366:64-73, 10 pgs.
Sato, T., et al., "Long-term expansion of epithelial organoids from human colon, adenoma, adenocarcinoma, and Barrett's epithelium," Gastroenterology, Nov. 2011, 141:1762-1772, 11 pgs.
Sato, T., et al., "Single Lgr5 stem cells build crypt-villus structures in vitro without a mesenchymal niche," Nature, 2009, 459:262-265, 5 pgs.
Schlieve, C.R., et al., "Created of Warm Blood and Nerves: Restoring an Enteric Nervous System in Organoids," Cell Stem Cell, Jan. 2017, 20:5-7, 3 pgs.
Schmelter, M., et al., "Embryonic stem cells utilize reactive oxygen species as transducers of mechanical strain-induced cardiovascular differentiation," The FASEB Journal, Jun. 2006, 20(8):1182-1184, 16 pgs.
Schonhoff, S.E., et al., "Neurogenin 3-expressing progenitor cells in the gastrointestinal tract differentiate into both endocrine and non-endocrine cell types," Dev Biol, 2004, 270:443-454, 12 pgs.
Schumacher, M.A., et al., "Gastric Sonic Hedgehog Acts as a Macrophage Chemoattractant During the Immune Response to *Helicobacter pylori*," Gastroenterology, 2012, 142:1150-1159, 16 pgs.
Schuppan, D., et al., "Non-alcoholic steatohepatitis: Pathogenesis and novel therapeutic approaches," Journal of Gastroenterology and Hepatology, 2013, 28(Suppl 1):68-76, 9 pgs.
Shah, S.B., et al., "Cellular self-assembly and biomaterials-based organoid models of development and diseases," Acta Biomaterialia, 2017, 53:29-45, 17 pgs.
Shan, J., et al., "Identification of a Specific Inhibitor of the Dishevelled PDZ Domain," Biochemistry, 2005, 44(47):15495-15503, 9 pgs.
Shimizu, N., et al., "Cyclic strain induces mouse embryonic stem cell differentiation into vascular smooth muscle cells by activating PDGF receptor β," J Appl Physiol, 2008, 104:766-772, 7 pgs.
Simon-Assmann, P., et al., "In vitro models of intestinal epithelial cell differentiation," Cell Biol. Toxicol., 2007, 23:241-256, 16 pgs.
Sinagoga, K.L., et al., "Generating human intestinal tissues from pluripotent stem cells to study development and disease," The EMBO Journal, 2015, 34(9):1149-1163, 15 pgs.
Singh, S., et al., "Comparative Effectiveness of Pharmacological Interventions for Nonalcoholic Steatohepatitis: A Systematic Review and Network Meta-analysis," Hepatology, Nov. 2015, 62(5):1417-1432, 16 pgs.
Si-Tayeb, K., et al., "Highly Efficient Generation of Human Hepatocyte-Like Cells from Induced Pluripotent Stem Cells," Hepatology, 2010, 51:297-305, 9 pgs.
Skardal, A., et al., "Organoid-on-a-chip and body-on-a-chip systems for drug screening and disease modeling," Drug Discovery Today, Sep. 2016, 21(9):1399-1411, 13 pgs.
Snoeck, H-W., "Generation of Anterior Foregut Derivatives from Pluripotent Stem Cells," Stem Cells Handbook, S. Sell (ed.), 2013, pp. 161-175.
Snykers, S., et al., "In Vitro Differentiation of Embryonic and Adult Stem Cells into Hepatocytes: State of the Art," Stem Cells, 2009, 27:577-605, 29 pgs.
Sonntag, F., et al., "Design and prototyping of a chip-based multi-micro-organoid culture system for substance testing, predictive to human (substance) exposure," Journal of Biotechnology, 2010, 148:70-75, 6 pgs.
Soto-Gutierrez, A., et al., "Engineering of an Hepatic Organoid to Develop Liver Assist Devices," Cell Transplant., 2010, 19(6):815-822, 12 pgs.
Spear, P.C., et al., "Interkinetic nuclear migration: A mysterious process in search of a function," Develop. Growth Differ., 2012, 54:306-316, 12 pgs.
Speer, M.D., A.L., et al., "Murine Tissue-Engineered Stomach Demonstrates Epithelial Differentiation," Journal of Surgical Research, Mar. 22, 2011, 171(1):6-14, XP028317226, 9 pgs.

(56) References Cited

OTHER PUBLICATIONS

Spence, J.R., et al., "Translational Embryology: Using Embryonic Principles to Generate Pancreatic Endocrine Cells from Embryonic Stem Cells," Developmental Dynamics, 2007, 236:3218-3227, 10 pgs.
Spence, J.R., et al., "Directed differentiation of human pluripotent stem cells into intestinal tissue in vitro," Nature, 2011, 470:105-109, 13 pgs.
Stadtfeld, M., et al., "Induced pluripotent stem cells generated without viral integration," Science, 2008, 322(5903):945-949, 12 pgs.
Stark, R., et al., "Development of an endoluminal intestinal lengthening capsule," Journal of Pediatric Surgery, 2012, 47:136-141, 6 pgs.
Sugawara, T., et al., "Organoids recapitulate organs?," Stem Cell Investig, 2018, vol. 5, Iss. 3, 4 pgs.
Sui, L., et al., "Signaling pathways during maintenance and definitive endoderm differentiation of embryonic stem cells," Int J Dev Bio, 2013, 57:1-12, 12 pgs.
Sun, Y., et al., "Genome engineering of stem cell organoids for disease modeling," Protein Cell, 2017, 8(5):315-327, 13 pgs.
Taipale, J., et al., "The Hedgehog and Wnt signalling pathways in cancer," Nature, 2001, 411:349-354, 8 pgs.
Tait, I.S., et al., "Colonic mucosal replacement by syngeneic small intestinal stem cell transplantation," The American Journal of Surgery, Jan. 1994, 167:67-72, 6 pgs.
Tait, I.S., et al., "Generation of neomucosa in vivo by transplantation of dissociated rat postnatal small intestinal epithelium," Differentiation, 1994 56:91-100, 10 pgs.
Takahashi, K. et al., "Induction of Pluripotent Stem Cells from Adult Human Fibroblasts by Defined Factors," Cell, 2007, 131:861-872, 12 pgs.
Takahashi, K., et al., "Induction of Pluripotent Stem Cells from Mouse Embryonic and Adult Fibroblast Cultures by Defined Factors," Cell, 2006, 126:663-676, 14 pgs.
Takaki, M., et al., "In Vitro Formation of Enteric Neural Network Structure in a Gut-Like Organ Differentiated from Mouse Embryonic Stem Cells," Stem Cells, Jun. 9, 2006, 24(6):1414-1422, XP55241404, 9 pgs.
Tamminen, K., et al., "Intestinal Commitment and Maturation of Human Pluripotent Stem Cells Is Independent fo Exogenous FGF4 and R-spondin1," PLOS One, Jul. 2015, 10(7):e0134551, 19 pgs.
Tang, W., et al., "Faithful expression of multiple proteins via 2A-peptide self-processing: a versatile and reliable method for manipulating brain circuits," The Journal of Neuroscience, Jul. 8, 2009, 29:8621-8629, 9 pgs.
Teo, A.K.K., et al., "Activin and BMP4 Synergistically Promote Formation of Definitive Endoderm in Human Embryonic Stem Cells," Stem Cells, 2012, 30:631-642, 12 pgs.
Thomson, J.A., et al., "Embryonic Stem Cell Lines Derived from Human Blastocysts," Science, 1998, 282(5391):1145-1147, 4 pgs.
Tiso, N., et al., "BMP signalling regulates anteroposterior endoderm patterning in zebrafish," Mech Dev, 2002, 118:29-37, 9 pgs.
Toivonen, S., et al., "Activin A and Wnt-dependent specification of human definitive endoderm cells," Experimental Cell Research, 2013, 319:2535-2544, 10 pgs.
Tsakmaki, A., et al., "3D intestinal organoids in metabolic research: virtual reality in a dish," Current Opinion in Pharmacology, 2017, 37:51-58, 8 pgs.
Tuschl, T., et al., "Targeted mRNA degradation by double-stranded RNA in vitro," Genes Dev., 1999, 13:3191-3197, 8 pgs.
Van Breemen, R.B., et al., "Caco-2 cell permeability assays to measure drug absorption," Expert Opin. Drug Metab. Toxicol., Aug. 2005, 1(2):175-185, 11 pgs.
Verzi, M.P., et al., "Role of the Homeodomain Transcription Factor Bapx1 in Mouse Distal Stomach Development," Gastroenterology, 2009, 136: 1701-1710, 10 pgs.

Wallace, A.S., et al., "Development of the enteric nervous system, smooth muscle and interstitial cells of Cajal in the human gastrointestinal tract," Cell and Tissue Research, Jan. 26, 2005, 319:367-382, 16 pgs.
Wang, A., et al., "Generating cells of the gastrointestinal system: current approaches and applications for the differentiation of human pluripotent stem cells," J Mol Med, 2012, 90:763-771, 9 pgs.
Wang, F., et al., "Isolation and characterization of intestinal stem cells based on surface marker combinations and colony-formation assay," Gastroenterology, 2013, 145:383-395.e1-e21, 34 pgs.
Wang, J., et al., "Mutant Neurogenin-3 in Congenital Malabsorptive Diarrhea," New England Journal of Medicine, 2006, 355:270-280, 11 pgs.
Wang, Z., et al., "Retinoic acid regulates morphogenesis and patterning of posterior foregut derivatives," Dev Biol, 2006, 297:433-445.
Ward, D.F., Jr., et al., "Mechanical Strain Enhances Extracellular Matrix-Induced Gene Focusing and Promotes Osteogenic Differentiation of Human Mesenchymal Stem Cells Through an Extracellular-Related Kinase-Dependent Pathway," Stem Cells and Development, 2007, 16:467-479, 14 pgs.
Warlich, E., et al., "Lentiviral vector design and imaging approaches to visualize the early stages of cellular reprogramming," Mol. Ther., Apr. 2011, 19:782-789, 9 pgs.
Watson, C.L., et al., "An in vivo model of human small intestine using pluripotent stem cells," Nature Medicine, Oct. 19, 2014, 20(11):1310-1314, XP055241417, 7 pgs.
Wells, J.M., et al., "Early mouse endoderm is patterned by soluble factors from adjacent germ layers," Development, 2000, 127:1563-1572, 10 pgs.
Wells, J.M. et al., "How to Make an intestine," Development, Feb. 15, 2014, 141(4):752-760, XP055241409, 9 pgs.
Wen, S. et al., "*Helicobacter pylori* virulence factors in gastric carcinogenesis," Cancer Lett., 2009, 282:1-8, 8 pgs.
Willet, S.G., et al., "Stomach Organ and Cell Lineage Differentiation: From Embryogenesis to Adult Homeostasis," Cellular and Molecular Gastroenterology and Hepatology, 2016, 2(5):546-559, 14 pgs.
Williamson, R.C.N., et al., "Humoral stimulation of cell proliferation in small bowel after transection and resection in rats," Gastroenterology, 1978, 75:249-254, 6 pgs.
Woltjen, K., et al., "piggyBac transposition reprograms fibroblasts to induced pluripotent stem cells," Nature, 2009, 458:766-770, 8 pgs.
Workman, M.J., "Generating 3D human intestinal organoids with an enteric nervous system," Thesis, Graduate School of the University of Cincinnati, Oct. 2014, 61 pgs.
Workman, M.J., et al., "Engineered human pluripotent-stem-cell-derived intestinal tissues with a functional enteric nervous system," Nat Med, Jan. 2017, 23(1):49-59, 29 pgs.
Xia, H.H-X., et al. "Antral-Type Mucosa in the Gastric Incisura, Body, and Fundus (Antralization): A Link Between *Helicobacter pylori* Infection and Intestinal Metaplasia?", Am. J. Gastroenterol., 2000, 95:114-121, 8 ps.
Xinaris, C., et al., "Organoid Models and Applications in Biomedical Research," Nephron, 2015, 130:191-199, 9 pgs.
Yamada, S., et al. "Differentiation of immature enterocytes into enteroendocrine cells by Pdx1 overexpression," Am. J. Physiol. Gastrointest. Liver Pyshiol., 2001, 281:G229-G236, 8 pgs.
Yin, C., et al., "Hepatic stellate cells in liver development, regeneration, and cancer," The Journal of Clinical Investigation, May 2013, 123(5):1902-1910, 9 pgs.
Young, H.M., et al., "Expression of Ret-, $p75^{NTR}$-, Phox2a-, Phox2b-, and tyrosine hydroxylase-immunoreactivity by undifferentiated neural crest-derived cells and different classes of enteric neurons in the embryonic mouse gut," Developmental Dynamics, 1999, 216:137-152, 16 pgs.
Young, H.M., et al., "GDNF is a chemoattractant for enteric neural cells," Developmental biology, Dec. 19, 2000, 229:503-516, 14 pgs.
Yuan, Y., et al., "Peptic ulcer disease today," Nat Clin Pract Gastroenterol Hepatol, 2006, 3:80-89 10 pgs.

(56) References Cited

OTHER PUBLICATIONS

Yui, S., et al., "Functional engraftment of colon epithelium expanded in vitro from a single adult Lgr5(+) stem cell," Nature Medicine, Apr. 2012, 18:618-623, 8 pgs.
Zachos, N.C., et al., "Human Enteroids/Colonoids and Intestinal Organoids Functionally Recapitulate Normal Intestinal Physiology and Pathophysiology," The Journal of Biological Chemistry, Feb. 2016, 291(8):3759-3766, 8 pgs.
Zhang, D., et a., "Neural crest regionalisation for enteric nervous system formation: implications for Hirschsprung's disease and stem cell therapy," Developmental Biology, Jan. 18, 2010, 339:280-294, 15 pgs.
Zhang, Q, et al., "Small-molecule synergist of the Wnt/β-catenin signaling pathway," Proc Natl Acad Sci USA, 2007, 104(18):7444-7448, 6 pgs.
Zhang, W., et al., "Elastomeric Free-Form Blood Vessels for Interconnecting Organs on Chip Systems," Lab Chip, Apr. 2016, 16(9):1579-1586, 19 pgs.
Zhang, Y.S., et al., "Multisensor-integrated organs-on-chips platforms for automated and continual in situ monitoring of organoid behaviors," PNAS Early Edition, 2017, 10 pgs.
Zhang, Y.S., et al., "Seeking the tight context for evaluating nanomedicine: from tissue models in petri dishes to microfluidic organs-on-a-chip," Nanomedicine (Lond.), 2015, 10(5):685-688, 4 pgs.
Zhou, H., et al., "Generation of Induced Pluripotent Stem Cells Using Recombinant Proteins," Cell Stem Cell, 2009, 4(5):381-384, 4 pgs.
Zhou, J., et al., "The Potential for Gut Organoid Derived Interstitial Cells of Cajal in Replacement Therapy," International Journal of Molecular Sciences, Sep. 2017, 18:1-17, 17 pgs.
Zhou, Q., et al., "In vivo reprogramming of adult pancreatic exocrine cells to β-cells," Nature, 2008, 455: 627-632, 6 pgs.
Zorn, A.M., et al., "Vertebrate endoderm development and organ formation," Annu Rev Cell Dev Biol, 2009, 25:221-251, 36 pgs.
European Exam Report dated Sep. 28, 2017 for Application No. EP 15728704.6, 4 pgs.
European Exam Report dated Jul. 4, 2018 for Application No. EP 15728704.6, 3 pgs.
European Exam Report dated May 18, 2018 for Application No. EP 15791404.5, 3 pgs.
International Search Report dated Feb. 9, 2012 for Application No. PCT/US2011/035518, 7 pgs.
International Preliminary Report on Patentability and Written Opinion dated Nov. 6, 2012 for Application No. PCT/US2011/035518, 5 pgs.
International Search Report and Written Opinion dated Dec. 15, 2015 for Application No. PCT/US2015/032626, 19 pgs.
International Search Report and Written Opinion dated Jan. 25, 2016 for Application No. PCT/US2015/055956, 16 pgs.
International Preliminary Report on Patentability dated Apr. 18, 2017 for Application No. PCT/US2015/055956, 8 pgs.
International Search Report and Written Opinion dated Aug. 14, 2017 for Application No. PCT/US2017/031309, 17 pgs.
International Search Report and Written Opinion dated Jan. 18, 2018 for Application No. PCT/US2017/059865, 12 pgs.
International Search Report and Written Opinion dated Jan. 19, 2018 for Application No. PCT/US2017/059845, 13 pgs.
International Search Report and Written Opinion dated Jan. 29, 2018 for Application No. PCT/US2017/059860, 13 pgs.
International Search Report and Written Opinion dated Feb. 21, 2018 for Application No. PCT/US2017/064600, 15 pgs.
International Search Report and Written Opinion dated Jun. 14, 2018 for Application No. PCT/US2018/018585, 14 pgs.
International Searching Authority Invitation to Pay Additional Fees and, Where Applicable, Protest Fee, dated Jun. 27, 2018 for Application No. PCT/US/2018/029083, 3 pgs.
Singaporean Written Opinion dated Oct. 19, 2017 for Application No. SG11201609953X, 8 pgs.
Singaporean Second Written Opinion dated Sep. 4, 2018 for Application No. SG11201609953X, 6 pgs.
U.S. Appl. No. 61/332,178, filed May 6, 2010.
U.S. Appl. No. 62/003,719, filed May 28, 2014.
U.S. Appl. No. 62/065,131, filed Oct. 17, 2014.
Ajmera, V., et al., "Novel Plasma Biomarkers Associated with Liver Disease Severity in Adults with Nonalcoholic Fatty Liver Disease," Hepatology, 2017, 65(1):65-77, 21 pgs.
Aleo, M.D., et al., "Human Drug-Induced Liver Injury Severity is Highly Associated with Dual Inhibition of Liver Mitochondrial Function and Bile Salt Export Pump," Hepatology, 2014, 60:1015-1022, 8 pgs.
Allard, J., et al., "Immunohistochemical toolkit for tracking and quantifying xenotransplanted human stem cells," Regenerative Medicine, 2014, 9(4):437-452, 11 pgs.
Arroyo, J.D., et al., "Argonaute2 complexes carry a population of circulating microRNAs independent of vesicles in human plasma," PNAS, 2011, 108(12):5003-5008, 6 pgs.
Bahar Halpern, K., et al. "Single-cell spatial reconstruction reveals global division of labour in the mammalian liver," Nature, 2017, 542:352-356, 18 pgs.
Bar-Ephraim, Y.E., et al., "Modelling cancer immunomodulation using epithelial organoid cultures," bioRxiv, 2018, accessed from Http://dx.doi.org/10.1101/377655v1.full, 13 pgs.
Barth, C.A., et al., "Transcellular transport of fluorescein in hepatocyte monolayers: Evidence for functional polarity of cells in culture," Proc Natl Acad Sci USA, 1982, 79:4985-4987, 3 pgs.
Begriche, K., et al., "Drug-induced toxicity on mitochondria and lipid metabolism: Mechanistic diversity and deleterious consequences for the liver," J Hepatol, 2011, 54:773-794, 22 pgs.
Bell, L.N., et al., "Epidemiology of Idiosyncratic Drug-Induced Liver Injury," Semin Liver Dis, 2009, 29(4):337-347, 11 pgs.
Bergeles, C., et al., "From Passive Tool Holders to Microsurgeons: Safer, Smaller, Smarter Surgical Robots," IEEE Trans Biomed Eng, 2014, 61(5):1565-1576, 12 pgs.
Bernardi, P., "The permeability transition pore. Control points of a cyclosporin A-sensitive mitochondrial channel involved in cell death," Biochim Biophys Acta, 1996, 1275:5-9, 5 pgs.
Bharadwaj, S., et al., "Current status of intestinal and multivisceral transplantation," Gastroentrerol Rep (Oxf)., 2017, 5(1):20-28, 9 pgs.
Bhutani, N., et al., Reprogramming towards pluripoteney requires AID-dependent DNA demethylation, Nature, 2010, 463(7284):1042-1047, 17 pgs.
Bohan, T.P., et al., "Effect of L-carnitine treatment for valproate-induced hepatotoxicity," Neurology, 2001, 56:1405-1409, 5 pgs.
Boroviak, T., et al., "Single cell transcriptome analysis of human, marmoset and mouse embryos reveals common and divergent features of preimplantation development," Development, 2018, 145(21):dev167833, 35 pgs.
Bort, R., et al., "Diclofenac Toxicity to Hepatocytes: A Role for Drug Metabolism in Cell Toxicity," J Pharmacol Exp Ther, 1998, 288(1):65-72, 8 pgs.
Boullata, J.I., et al. "A.S.P.E.N. Clinical Guidelines: Parenteral Nutrition Ordering, Order Review, Compounding, Labeling, and Dispensing," J Parenter Enteral Nutr, 2014, 38(3):334-377, 44 pgs.
Bragdon, B., et al., "Bone Morphogenetic Proteins: A critical review," Cellular Signalling, 2011, 23:609-620, 12 pgs.
Bravo, P., et al., "Efficient In Vitro Vectorial Transport of a Fluorescent Conjugated Bile Acid Analogue by Polarized Hepatic Hybrid WIF-B and WIF-B9 Cells," Hepatology, 1998, 27:576-583, 8 pgs.
Broda, T.R., et al., "Generation of human antral and fundic gastric organoids from pluripotent stem cells," Nature Protocols, Nov. 2018, 14(1):28-50, 23 pgs., XP036660403.
Browning, J.D., et al., "Molecular mediators of hepatic steatosis and liver injury," J Clin Invest, 2004, 114(2):147-152, 6 pgs.
Burke, P., et al., "Towards a single-chip, implantable RFID system: is a single-cell radio possible?" Biomed Microdevices, 2010, 12:589-596, 8 pgs.
Burn, S.F., et al., "Left-right asymmetry in gut development: What happens next?" BioEssays, 2009, 31:1026-1037, 12 pgs.
Caneparo, L., et al., "Intercellular Bridges in Vertebrate Gastrulation," PloS ONE, 2011, 6(5):e20230, 6 pgs.

(56) References Cited

OTHER PUBLICATIONS

Capeling, M.M., et al., "Nonadhesive Alginate Hydrogels Support Growth of Pluripotent Stem Cell-Derived Intestinal Organoids," Stem Cell Reports, Feb. 2019, 12(2):381-394, 14 pgs.

Chai, P.R., et al., "Utilizing an Ingestible Biosensor to Assess Real-Time Medication Adherence," J Med Toxicol, 2015, 11:439-444, 6 pgs.

Chai, P.R., et al., "Ingestible Biosensors for Real-Time Medical Adherence Monitoring: MyTMed," Proc Annu Hawaii Int Conf Syst Sci, Jan. 2016, 2016:3416-3423, 12 pgs.

Chang, J.H., et al., "Evaluating the In Vitro Inhibition of UGT1A1, OATP1B1, OATP1B3, MRP2, and BSEP in Predicting Drug-Induced Hyperbilirubinemia," Mol Pharm, 2013, 10:3067-3075, 9 pgs.

Chatterjee, S., et al., "Hepatocyte-based in vitro model for assessment of drug-induced cholestasis," Toxicol Appl Pharmacol, 2014, 274:124-136, 13 pgs.

Chen, B., et al., "Dynamic Imaging of Genomic Loci in Living Human Cells by an Optimized CRISPR/Cas System," Cell, 2013, 155(7):1479-1491, 23 pgs.

Chen, L.Y., et al., "Mass fabrication and delivery of 3D multilayer μTags into living cells," Sci Rep, 2013, 3:2295, 6 pgs.

Chen, Y., et al., "Retinoic acid signaling is essential for pancreas development and promotes endocrine at the expense of exocrine cell differentiation in *Xenopus*," Dev Biol, 2004, 271:144-160, 17 pgs.

Christoffersson, J., et al., "Developing organ-on-a-chip concepts using bio-mechatronic design methodology," Biofabrication, 2017, 9:025023, 14 pgs.

Chughlay, M.F., et al., "N-acetylcysteine for non-paracetamol drug-induced liver injury: a systematic review," Br J Clin Pharmacol, 2016, 81:1021-1029, 9 pgs.

Clarke, L.L., "A guide to Ussing chamber studies of mouse intestine," Am J Physiol Gastrointest Liver Physiol, 2009, 296:G1151-G1166, 16 pgs.

Collier, A.J., et al., "Comprehensive Cell Surface Protein Profiling Identifies Specific Markers of Human Naïve and Primed Pluripotent States," Cell Stem Cell, 2017, 20:874-890, 25 pgs.

Cortez, et al., "Transplantation of human intestinal organoids into the mouse mesentery: A more physiological and anatomic engraftment site," Surgery, 2018, 164:643-650, 8 pgs.

Crespo, M., et al., "Colonic organoids derived from human induced pluripotent stem cells for modeling colorectal cancer and drug testing," Nature Medicine, 2017, 23(7):878-884, 11 pgs.

Crocenzi, F.A., et al., "$Ca^{2+}$-Dependent Protein Kinase C Isoforms Are Critical to Estradiol 17β-D-Glucuronide-Induced Cholestasis in the Rat," Hepatology, 2008, 48:1885-1895, 12 pgs.

Cutrin, J.C., et al., "Reperfusion Damage to the Bile Canaliculi in Transplanted Human Liver," Hepatology, 1996, 24:1053-1057, 5 pgs.

Das, R., "RFID Forecasts, Players and Opportunities 2017-2027," IDTechEx, 2017, downloaded from https://www.idtechex.com/en/research-report/rfid-forecasts-players-and-opportunities-2017-2027/546, 8 pgs. Summary only.

Dash, A., et al., "Pharmacotoxicology of clinically-relevant concentrations of obeticholic acid in an organotypic human hepatocyte system," Toxicology In Vitro, 2017, 39:93-103, 11 pgs.

Davidson, M.D., et al., "Long-term exposure to abnormal glucose levels alters drug metabolism pathways and insulin sensitivity in primary human hepatocytes," Sci Rep, 2016, 6:28178, 11 pgs.

Dekkers, J.F., et al., "A functional CFTR assay using primary cystic fibrosis intestinal organoids," Nat Med, 2013, 19(7):939-945, 9 pgs.

Demehri, F.R., et al., "Development of an endoluminal intestinal attachment for clinically applicable distraction enterogenesis device," Journal of Pediatric Surgery, 2016, 51:101-106, 6 pgs.

Demehri, F.R., et al., "Development of an endoluminal intestinal lengthening device using a geometric intestinal attachment approach," Surgery, 2015, 158(3):802-811, 10 pgs.

Dumortier, G., et al., "Tolérance hépatique des antipsychotiques atypiques, [Hepatic tolerance of atypical antipsychotic drugs]," L'Encéphale, 2002, 28(1):542-551, 10 pgs.

Dvir-Ginzberg, M., et al., "Liver Tissue Engineering Within Alginate Scaffolds: Effects of Cell-Seeding Density on Hepatocyte Viability, Morphology, and Function," Tissue Eng, 2003, 9(4):757-766, 10 pgs.

Edling, Y., et al., "Increased sensitivity for troglitazone-induced cytotoxicity using a human in vitro co-culture model," Toxicol In Vitro, 2009, 23:1387-1395, 9 pgs.

Ekser, B., et al., "Comparable outcomes in intestinal retransplantation: Single-center cohort study," The Journal of Clinical and Translational Research, 2018, 32(7):e13290, 10 pgs.

El Kasmi, K.C., et al., "Phytosterols Promote Liver Injury and Kupffer Cell Activation in Parenteral Nutrition-Associated Liver Disease," Sci Transl Med, 2013, 5(206):206ra137, 10 pgs.

El Taghdouini, A., et al., "In vitro reversion of activated primary human hepatic stellate cells," Fibrogenesis & Tissue Repair, 2015, 8:14, 15 pgs.

The Encode Project Consortium, "An integrated encyclopedia of DNA elements in the human genome," Nature, 2012, 489:57-74, 18 pgs.

Engmann, J., et al., "Fluid mechanics of eating, swallowing and digestion—overview and perspectives," Food & Function, 2013, 4:443-447, 5 pgs.

Fahrmayr, C., et al., "Phase I and II metabolism and MRP2-mediated export of bosentan in a MDCKII-OATP1B1-CYP3A4-UGT1A1-MRP2 quadruple-transfected cell line," Br J Pharmacol, 2013, 169:21-33, 13 pgs.

Falasca, L., et al., "The effect of retinoic acid on the re-establishment of differentiated hepatocyte phenotype in primary culture," Cell Tissue Res, 1998, 293:337-347, 11 pgs.

Finkenzeller, K., *RFID Handbook: Fundamentals and Applications in Contactless Smart Cards, Radio Frequency Identification and Near-Field Communication, Third Edition*. John Wiley & Sons, Ltd., Chichester, West Sussex, 2010, 8 pgs. (Table of Contents Only).

Fisher, A., et al., "Entacapone-Induced Hepatotoxicity and Hepatic Dysfunction," Mov Disord, 2002, 17:1362-1365, 4 pgs.

Fromenty, B., "Drug-induced liver injury in obesity," J Hepatol, 2013, 58:824-826, 3 pgs.

Gafni, O., et al., "Derivation of novel human ground state naïve pluripotent stem cells," Nature, 2013, 504:282-286, 20 pgs.

Geerts, A., et al., "Formation of Normal Desmin Intermediate Filaments in Mouse Hepatic Stellate Cells Requires Vimentin," Hepatology, 2001, 33:177-188, 12 pgs.

Gerdes, H-H., et al., "Tunneling nanotubes, an emerging intercellular communication route in development," 2013, 130:381-387, 7 pgs.

Giles, D.A., et al., "Thermoneutral housing exacerbates nonalcoholic fatty liver disease in mice and allows for sex-independent disease modeling," Nature Medicine, 2017, 23(7):829-838, 13 pgs.

Glorioso, J.M., et al., "Pivotal Preclinical Trial of the Spheroid Reservoir Bioartificial Liver," J Hepatol, 2015, 63(2):388-398, 27 pgs.

Gomez-Pinilla, P.J., et al., "Ano1 is a selective marker of interstitial cells of Cajal in the human and mouse gastrointestinal tract," Am J Physiol Gastrointest Liver Physiol, 2009, 296:G1370-G1381, 12 pgs.

Grapin-Botton, A., "Three-dimensional pancreas organogenesis models," Diabetes Obes Metab, 2016, 18(Suppl 1):33-40, 8 pgs.

Gregersen, H., et al., "The Zero-Stress State of the Gastrointestinal Tract: Biomechanical and Functional Implications," Digestive Diseases and Sciences, 2000, 45(12):2271-2281, 11 pgs.

Guo, G., et al., "Epigenetic resetting of human pluripotency," Development, 2017, 144:2748-2763, 17 pgs.

Gurdon, J.B., "Adult Frogs Delived from the Nuclei of Single Somatic Cells," Dev Biol, 1962, 4:256-273, 18 pgs.

Gurken, A., "Advances in small bowel transplantation," Turk J Surg., 2017, 33(3):135-141, 7 pgs.

Haimovich, G., et al., "Intercellular mRNA trafficking via membrane nanotube-like extensions in mammalian cells," 2017, PNAS, pp. E9873-E9882, 10 pgs.

Han, B., et al., "Microbiological safety of a novel bio-artificial liver support system based on porcine hepatocytes: a experimental study," European Journal of Medical Research, 2012, 17:13, 8 pgs.

(56) References Cited

OTHER PUBLICATIONS

Hassan, W., et al., "Reduced Oxidative Stress Contributes to the Lipid Lowering Effects of Isoquercitrin in Free Fatty Acids Induced Hepatocytes," Oxid Med Cell Longev, 2014, 313602, 18 pgs.

Heidari, R., et al., "Factors affecting drug-induced liver injury: antithyroid drugs as instances," Clin Mol Hepatol, 2014, 20:237-248, 12 pgs.

Hernandez, F., et al., "Refining Indications for Intestinal Retransplantation," International Small Bowel Symposium 2013; Abstract 12.241 (online: https://www.tts.org/component/%20tts/?view=presentation&id=13241) Accessed Jun. 12, 2017, 3 pgs.

Hooton, D., et al., "The Secretion and Action of Brush Border Enzymes in the Mammalian Small Intestine," Rev Physiol Biochem Pharmacol, 2015, 168:59-118, 60 pgs.

Hou, P., et al., "Pluripotent Stem Cells Induced from Mouse Somatic Cells by Small-Molecule Compounds," Science, 2013, 341:651-654, 4 pgs.

Hsu, F., et al., "The UCSC Known Genes," Bioinformatics, 2006, 22(9):1036-1046, 11 pgs.

Hu, H., et al., "Long-Term Expansion of Functional Mouse and Human Hepatocytes as 3D Organoids," Cell, 2018, 175:1591-1606, 36 pgs.

Hu, X., et al., "Micrometer-Scale Magnetic-Resonance-Coupled Radio-Frequency Identification and Transceivers for Wireless Sensors in Cells," Physical Review Applied, 2017, 8:014031, 13 pgs.

Huch, M., et al., "Long-Term Culture of Genome-Stable Bipotent Stem Cells from Adult Human Liver," Cell, 2015, 160:299-312, 14 pgs.

Hynds, R.E., et al., "The relevance of human stem cell-derived organoid models for epithelial translational medicine," Stem Cells, 2013, 31(3):417-422, 11 pgs.

Ijpenberg, A., et al., "Wt1 and retinoic acid signaling are essential for stellate cell development and liver morphogenesis," Dev Biol, 2007, 312:157-170, 14 pgs.

Inoue, H., et al., "iPS cells: a game changer for future medicine," EMBO J, 2014, 33(5):409-417, 9 pgs.

Ito, K., et al., "Temporal Transition of Mechanical Characteristics of HUVEC/MSC Spheroids Using a Microfluidic Chip with Force Sensor Probes," Micromachines, 2016, 7:221, 14 pgs.

Jalan-Sakrikar, N., et al., "Hedgehog Signaling Overcomes an EZH2-Dependent Epigenetic Barrier to Promote Cholangiocyte Expansion," PLoS One, 2016, 11(12):e0168266, 19 pgs.

Kanuri, G., et al., "In Vitro and in Vivo Models of Non-Alcoholic Fatty Liver Disease (NAFLD)," Int J Mol Sci, 2013, 14:11963-11980, 18 pgs.

Karlikow, M., et al., "*Drosophila* cells use nanotube-like structures to transfer dsRNA and RNAi machinery between cells," Scientific Reports, 2016, 6:27085, 9 pgs.

Keitel, V., et al., "De Novo Bile Salt Transporter Antibodies as a Possible Cause of Recurrent Graft Failure After Liver Transplantation: A Novel Mechanism of Cholestasis," Hepatology, 2009, 50:510-517, 8 pgs.

Kelly, G.M., et al., "Retinoic Acid and the Development of the Endoderm," J Dev Biol, 2015, 3:25-56, 32 pgs.

Khan, F.A., et al., "Overview of intestinal and multivisceral transplantation," UpToDate, Sep. 2018 [online: https://www.uptodate.com/contents/overview-of-intestinal-and-multivisceral-transplantation/print], 32 pgs.

Kilens, S., et al., "Parallel derivation of isogenic human primed and naïve induced pluripotent stem cells," Nat Commun, 2018, 9:360, 13 pgs.

Kilpinen, H., et al., "Common genetic variation drives molecular heterogeneity in human iPSCs," Nature, 2017, 546(7658):370-375, 51 pgs.

Kim, D., et al., "HISAT: a fast spliced aligner with low memory requirements," Nature Methods, 2015, 12(4):357-360, 6 pgs.

Kock, K., et al., "A Perspective on Efflux Transport Proteins in the Liver," Clin Pharmacol Ther, 2012, 92(5):599-612, 29 pgs.

Koehler, E.M., et al., "Presence of Diabetes Mellitus and Steatosis Is Associated With Liver Stiffness In a General Population: The Rotterdam Study," Hepatology, 2016, 63:138-147, 10 pgs.

Kolodny, G.M., "Evidence for Transfer of Macromolecular RNA Between Mammalian Cells in Culture," Exp Cell Res, 1971, 65:313-324, 12 pgs.

Kordes, C., et al., "Hepatic stellate cells contribute to progenitor cells and liver regeneration," J Clin Invest, 2014, 124(12):5503-5515, 13 pgs.

Krähenbühl, S., et al., "Toxicity of Bile Acids on the Electron Transport Chain of Isolated Rat Liver Mitochondria," Hepatology, 1994, 19:471-479, 9 pgs.

Kubal, C.A., et al., "Challenges with Intestine and Multivisceral Re-Transplantation: Importance of Timing of Re-Transplantation and Optimal Immunosuppression," Ann Transplant, 2018, 23:98-104, 7 pgs.

Kullak-Ublick, G.A., et al., "Drug induced liver injury: recent advantages in diagnosis and risk assessment," Gut, 2017, 66:1154-1164, 11 pgs.

Kumar, J.A., et al., "Controversies in the Mechanism of Total Parenteral Nutrition Induced Pathology," Children, 2015, 2:358-370, 13 pgs.

Kurpios, N.A., et al., "The direction of gut looping is established by changes in the extracellular matrix and in cell:cell adhesion," PNAS, 2008, 105(25):8499-8506, 8 pgs.

Lê, S., et al., "FactoMineR: An R Package for Multivariate Analysis," Journal of Statistical Software, 2008, 25(1):1-18, 18 pgs.

Le Vee, M., et al., "Polarized expression of drug transporters in differentiated human hepatoma HepaRG cells," Toxicol In Vitro, 2013, 27:1979-1986, 8 pgs.

Lechner, C., et al., "Development of a fluorescence-based assay for drug interactions with human Multidrug Resistance Related Protein (MRP2; ABCC2) in MDCKII-MRP2 membrane vesicles," Eur J Pharm Biopharm, 2010, 75:284-290, 7 pgs.

Lee, W.M., et al., "Intravenous N-Acetylcysteine Improves Transplant-Free Survival In Early Stage Non-Acetaminophen Acute Liver Failure," Gastroenterology, 2009, 137(3):856-864, 18 pgs.

Leslie, E.M., et al., "Differential Inhibition of Rat and Human $Na^+$-Dependent Taurocholate Cotransporting Polypeptide (NTCP/SLC10A1) by Bosentan: A Mechanism for Species Differences in Hepatotoxicity," J Pharmacol Exp Ther, 2007, 321(3):1170-1178, 9 pgs.

Leung, A.A., et al., "Tolerance testing of passive radio frequency identification tags for solvent, temperature, and pressure conditions encountered in an anatomic pathology or biorepository setting," J Pathol Inform, 2010, 1:21, 6 pgs.

Li, N., et al., "A Systematic Assessment of Mitochondrial Function Identified Novel Signatures for Drug-Induced Mitochondrial Disruption in Cells," Toxicol Sci, 2014, 142(1):261-273, 13 pgs.

Lin, Y., et al., "Differentiation, Evaluation, and Application of Human Induced Pluripotent Stem Cell-Derived Endothelial Cells," Arterioscler Thromb Vasc Biol, 2017, 37:2014-2025, 12 pgs.

Liu, L., et al., "A Review of Locomotion Systems for Capsule Endoscopy," IEEE Rev Biomed Eng, 2015, 8:138-151, 14 pgs.

Loike, J.D., et al., "Opinion: Develop Organoids, Not Chimeras, for Transplantation," The Scientist Magazine, Aug. 2019, (Online: https://www.the-scientist.com/news-opinion/opinion--develop-organoids--not-chimeras--for-transplantation-66339), 3 pgs.

Love, M.I., et al., "Moderated estimation of fold change and dispersion for RNA-seq data With DESeq2," Genome Biol, 2014, 15:550, 21 pgs.

Low, L.A., et al., "Organs-on-chips: Progress, challenges, and future directions," Experimental Biology and Medicine, 2017, 242:1573-1578, 6 pgs.

Luntz, J., et al., "Mechanical Extension Implants for Short-Bowel Syndrome," Smart Structures and Materials 2006: Smart Structures and Integrated Systems, Proc of SPIE, 2006, 6173:617309-1-617309-11, 11 pgs.

MacParland, S.A., et al., "Single cell RNA sequencing of human liver reveals distinct intrahepatic macrophage populations," Nat Commun, 2018, 9:4383, 21 pgs.

Mahe, M.M., et al., "In Vivo Model of Small Intestine," Methods Mol Biol, 2017, 1597:229-245, 17 pgs.

(56) References Cited

OTHER PUBLICATIONS

Makin, A.J., et al., "A 7-Year Experience of Severe Acetaminophen-Induced Hepatotoxicity (1987-1993)," Gastroenterology, 1995, 109:1907-1916, 10 pgs.

Malinen, M.M., et al., "Differentiation of liver progenitor cell line to functional organotypic cultures in 3D nanofibrillar cellulose and hyaluronan-gelatin hydrogels," Biomaterials, 2014, 35:5110-5121, 12 pgs.

Mammoto, A., et al., "Mechanosensitive mechanisms in transcriptional regulation," Journal of Cell Science, 2012, 125:3061-3073, 13 pgs.

Marcum, Z.A., et al., "Medication Adherence to Multi-Drug Regimens," Clin Geriatr Med, 2012, 28(2):287-300, 15 pgs.

Marini, F., et al., "pcaExplorer: an R/Bioconductor package for interacting with RNA-seq principal components," BMC Bioinformatics, 2019, 20:331, 8 pgs.

Marini, F., "pcaExplorer: Interactive Visualization of RNA-seq Data Using a Principal Components Approach," bioconductor.org, R package version 2.3.0, 2017, 7 pgs.

Markova, S.M., et al., "Association of CYP2C9*2 With Bosentan-Induced Liver Injury," Clin Pharmacol Ther., Dec. 2013, 94(6):678-86, 9 pgs.

Marsh, M.N., et al., "A study of the small intestinal mucosa using the scanning electron microscope," Gut, 1969, 10:940-949, 10 pgs.

McCracken, K.W., et al., "Erratum: Wnt/β-catenin promotes gastric fundus specification in mice and humans," Nature, 2017, 543:136, 1 pg.

McKenzie, T.J., et al., "Artificial and Bioartificial Liver Support," Seminars in Liver Disease, 2008, 28(2):210-217, 8 pgs.

Mercaldi, C.J., et al., "Methods to Identify and Compare Parenteral Nutrition Administered From Hospital-Compounded and Premixed Multichamber Bags in a Retrospective Hospital Claims Database," J Parenter Enteral Nutr, 2012, 36(3):330-336, 7 pgs.

Michaut, A., et al., "A cellular model to study drug-induced liver injury in nonalcoholic fatty liver disease: application to acetaminophen," Toxicol Appl Pharmacol, 2016, 292:40-55, 35 pgs.

Miki, T., et al., "Hepatic Differentiation of Human Embryonic Stem Cells Is Promoted by Three-Dimensional Dynamic Perfusion Culture Conditions," Tissue Eng: Part C Methods, 2011, 17(5):557-568, 12 pgs.

Mörk, L.M., et a., "Comparison of Culture Media for Bile Acid Transport Studies in Primary Human Hepatocytes," J Clin Exp Hepatol, 2012, 2:315-322, 8 pgs.

Nakamura, T., et al., "Advancing Intestinal Organoid Technology Toward Regenerative Medicine," Cell Mol Gastroenterol Hepatol, 2018, 5:51-60, 10 pgs.

Navarro, V.J., et al., "Drug-Related Hepatotoxicity," N Engl J Med, 2006, 354:731-739, 9 pgs.

Negishi, T., et al., "Retinoic Acid Signaling Positively Regulates Liver Specification by Inducing wnt2bb Gene Expression in Medaka," Hepatology, 2010, 51:1037-1045, 9 pgs.

Nelson, B.J., et al., "Microrobots for Minimally Invasive Medicine," Annual Review of Biomedical Engineering, 2010, 12(12):55-85, 33 pgs.

Nelson, C.M., "On Buckling Morphogenesis," J Biomech Eng, 2016, 138:021005-1-021005-6, 6 pgs.

Ni, X., et al., "Functional human induced hepatocytes (hiHeps) with bile acid synthesis and transport capacities: A novel in vitro cholestatic model," Sci Rep, 2016, 6:38694, 16 pgs.

Nishida, T., et al., "Rat liver canalicular membrane vesicles contain an ATP-dependent bile acid transport system," Proc Natl Acad Sci USA, 1991, 88:6590-6594, 5 pgs.

Oorts, M., et al., "Drug-induced cholestasis risk assessment in sandwich-cultured human hepatocytes," Toxicol In Vitro, 2016, 34:179-186, 8 pgs.

Orso, G., et al., "Pediatric parenteral nutrition-associated liver disease and cholestasis: Novel advances in pathomechanisms-based prevention and treatment," Dig Liver Dis, 2016, 48:215-222, 8 pgs.

Ouchi, R., et al., "Modeling Steatohepatitis in Humans with Pluripotent Stem Cell-Derived Organoids," Cell Metabolism, Aug. 2019, 30:1-11, 17 pgs.

Pardal, M.L., et al., "Towards the Internet of Things: An Introduction to RFID technology," RFID Technology-Concepts, Applications, Challenges, Proceedings of the 4th International Workshop, IWRT 2010, In conjunction with ICEIS 2010, Funchal, Madeira, Portugal, Jun. 2010, pp. 69-78, 10 pgs.

Pastor, W.A., et al., "TFAP2C regulates transcription in human naïve pluripotency by opening enhancers," Nature Cell Biology, 2018, 20:553-564, 18 pgs.

Pereira, C.F., et al., "Heterokaryon-Based Reprogramming of Human B Lymphocytes for Pluripotency Requires Oct4 but Not Sox2," PLoS Genet, 2008, 4(9):e1000170, 14 pgs.

Pessayre, D., et al., "Central role of mitochondria in drug-induced liver injury," Drug Metab Rev, 2012, 44(1):34-87, 54 pgs.

Pessayre, D., et al., "Mitochondrial involvement in drug-induced liver injury," in *Adverse Drug Reaction*, J. Uetrecht (ed.), Handb Exp Pharmacol 196, Springer-Verlag, Berlin, Germany, 2010, pp. 311-365, 55 pgs.

Poling, H.M., et al., "Mechanically induced development and maturation of human intestinal organoids in vivo," Nat Biomed Eng, 2018, 2(6):429-442, 31 pgs.

Polson, J., et al., "AASLD Position Paper: The Management of Acute Liver Failure," Hepatology, 2005, 41(5):1179-1197, 19 pgs.

Purton, L.E., et al., "All-trans retinoic acid enhances the long-term repopulating activity of cultured hematopoietic stem cells," Blood, 2000, 95:470-477, 8 pgs.

Rachek, L.I., et al., "Troglitazone, but not rosiglitazone, damages mitochondrial DNA and induces mitochondrial dysfunction and cell death in human hepatocytes," Toxicol Appl Pharmacol, 2009, 240(3):348-354, 17 pgs.

Ramirez-Weber, F-A., et al., "Cytonemes: Cellular Processes that Project to the Principal Signaling Center in *Drosophila* Imaginal Discs," Cell, 1999, 97:599-607, 9 pgs.

Rane, A., et al., "Drug Metabolism in the Human Fetus and Newborn Infant," Pediatr Clin North Am, 1972, 19(1):37-49, 11 pgs.

Rao, R.R., et al., "Gene Expression Profiling of Embryonic Stem Cells Leads to Greater Understanding of Pluripotency and Early Developmental Events," Biol Reprod, 2004, 71:1772-1778, 7 pgs.

Rector, R.S., et al., "Mitochondrial dysfunction precedes insulin resistance and hepatic steatosis and contributes to the natural history of non-alcoholic fatty liver disease in an obese rodent model," J Hepatol, 2010, 52(5):727-736, 20 pgs.

Reuben, A., et al. "Drug-Induced Acute Liver Failure: Results of a U.S. Multicenter, Prospective Study," Hepatology, 2010, 52:2065-2076, 12 pgs.

Riedinger, H-J, et al., "Reversible shutdown of replicon initiation by transient hypoxia in Ehrlich ascites cells: Dependence of initiation on short-lived protein," Eur J. Biochem, 1992, 210:389-398, 10 pgs.

Roberts, A., et al., "Identification of novel transcripts in annotated genomes using RNA-Seq," Bioinformatics, 2011, 27(17):2325-2329, 5 pgs.

Roberts, A., et al., "Improving RNA-Seq expression estimates by correcting for fragment bias," Genome Biol, 2011, 12:R22, 14 pgs.

Ronn, R.E., et al., "Retinoic Acid Regulates Hematopoietic Development from Human Pluripotent Stem Cells," Stem Cell Reports, 2015, 4:269-281, 13 pgs.

Rouch, J.D., et al., "Scalability of an endoluminal spring for distraction enterogenesis," Journal of Pediatric Surgery, 2016, 51:1988-1992, 5 pgs.

Roy, S., et al., "Cytoneme-Mediated Contact-Dependent Transport of the *Drosophila* Decapentaplegic Signaling Protein," Science, 2014, 343:1244624-1, 11 pgs.

Russo, M.W., et al., "Liver Transplantation for Acute Liver Failure From Drug Induced Liver Injury in the United States," Liver Transpl, 2004, 10:1018-1023, 6 pgs.

Sachs, N., et al., "A Living Biobank of Breast Cancer Organoids Captures Disease Heterogeneity," Cell, 2018, 172:373-386, 25 pgs.

Saini, A., "Cystic Fibrosis Patients Benefit from Mini Guts," Cell Stem Cell, 2016, 19:425-427, 3 pgs.

(56) References Cited

OTHER PUBLICATIONS

Salas-Vidal, E., et al., "Imaging filopodia dynamics in the mouse blastocyst," Developmental Biology, 2004, 265:75-89, 15 pgs.
Sartori-Rupp, A., et al., "Correlative cryo-electron microscopy reveals the structure of TNTs in neuronal cells," Nature Communications, 2019, 10:342, 16 pgs.
Sasai, Y., "Cytosystems dynamics in self-organization of tissue architecture," Nature, 2013, 493:318-326, 9 pgs.
Sato, T., et al., "Snapshot: Growing Organoids from Stem Cells," Cell, 2015, 161:1700-1700e1, 2 Pgs.
Serviddio, G., et al., "Ursodeoxycholic Acid Protects Against Secondary Biliary Cirrhosis in Rats by Preventing Mitochondrial Oxidative Stress," Hepatology, 2004, 39:711-720, 10 pgs.
Shahbazi, M.N., et al., "Self-organization of the human embryo in the absence of maternal tissues," Nature Cell Biology, 2016, 18(6):700-708, 20 pgs.
Shekherdimian, S., et al., "The feasibility of using an endoluminal device for intestinal lengthening," Journal of Pediatric Surgery, 2010, 45:1575-1580, 6 pgs.
Shi, X-L., et al., "Effects of Membrane Molecular Weight Cutoff on Performance of a Novel Bioartificial Liver," Artificial Organs, 2011, 35(3):E40-E46, 7 pgs.
Shi, X-L., et al., "Evaluation of a novel hybrid bioartificial liver based on a multi-layer flat-plate bioreactor," World J Gastroenterol, 2012, 18(28):3752-3760, 9 pgs.
Shyer, A.E., et al., "Villification: How the Gut Gets its Villi," Science, 2013, 342:212-218, 7 pgs.
Sim, Y-J., et al., "2i Maintains a Naïve Ground State in ESCs through Two Distinct Epigenetic Mechanisms," Stem Cell Reports, 2017, 8:1312-1328, 17 pgs.
Sitti, M., et al., "Biomedical Applications of Untethered Mobile Milli/Microrobots," Proc IEEE Inst Electr Electron Eng, 2015, 103(2):205-224, 20 pgs.
Slaymaker, I.M., et al., "Rationally engineered Cas9 nucleases with improved specificity," Science, 2016, 351(6268):84-88, 10 pgs.
Sloan, C.A., et al., "ENCODE data at the ENCODE portal," Nucleic Acids Res, 2016, 44:D726-D732, 7 pgs.
Sneddon, I.N., "The Relation Between Load and Penetration in the Axisymmetric Boussinesq Problem for a Punch of Arbitrary Profile," Int. J. Engng. Sci., 1965, 3:47-57, 11 pgs.
Soffers, J.H.M., et al., "The growth pattern of the human intestine and its mesentery," BMC Dev Biol, 2015, 15:31, 16 pgs.
Song, W., et al., "Engraftment of human induced pluripotent stem cell-derived hepatocytes in immunocompetent mice via 3D co-aggregation and encapsulation," Sci Rep, 2015, 5:16884, 13 pgs.
Song, Z., et al., "Efficient generation of hepatocyte-like cells from human induced pluripotent stem cells," Cell Res, 2009, 19:1233-1242, 10 pgs.
Spence, J.R., et al., "Vertebrate Intestinal Endoderm Development," Developmental Dynamics, 2011, 240:501-520, 20 pgs.
Stafford, D., et al., "A conserved role for retinoid signaling in vertebrate pancreas development," Dev Genes Evol, 2004, 214:432-441, 10 pgs.
Stender, S., et al., "Adiposity Amplifies the Genetic Risk of Fatty Liver Disease Conferred by Multiple Loci," Nat Genet, 2017, 49(6):842-847, 18 pgs.
Stevens, J.L., et al., "The future of drug safety testing: expanding the view and narrowing the focus," Drug Discov Today, 2009, 14(3/4):162-167, 6 pgs.
Stuart, T., et al., "Comprehensive Integration of Single-Cell Data," Cell, 2019, 177:1888-1902, 37 pgs.
Sugimoto, S., et al., "Reconstruction of the Human Colon Epithelium In Vivo," Cell Stem Cell, 2018, 22:171-176, 16 pgs.
Suzuki, A., et al., "Clonal identification and characterization of self-renewing pluripotent stem cells in the developing liver," The Journal of Cell Biology, 2002, 156(1):173-184, 12 pgs.
Tada, M., et al., "Embryonic germ cells induce epigenetic reprogramming of somatic nucleus in hybrid cells," EMBO J, 1997, 16(21):6510-6520, 11 pgs.

Takahashi, S., et al., "Epigenetic differences between naïve and primed pluripotent stem cells," Cellular and Molecular Life Sciences, 2018, 75:1191-1203, 13 pgs.
Takashima, Y., et al., "Resetting Transcription Factor Control Circuitry toward Ground-State Pluripotency in Human," Cell, 2014, 158(6):1254-1269, 32 pgs.
Takebe, T., et al., "Human iPSC-Derived Miniature Organs: A Tool for Drug Studies," Clin Pharmacol Ther, 2014, 96(3):310-313, 4 pgs.
Takebe, T., et al., "Massive and Reproducible Production of Liver Buds Entirely from Human Pluripotent Stem Cells," Cell Reports, 2017, 21:2661-2670, 11 pgs.
Takebe, T., et al., "Vascularized and Complex Organ Buds from Diverse Tissues via Mesenchymal Cell-Driven Condensation," Cell Stem Cell, 2015, 16:556-565, 10 pgs.
Takebe, T., et al., "Vascularized and functional human liver from an iPSC-derived organ bud transplant," Nature, 2013, 499:481-484, 5 pgs.
Tamm, C., et al., "A Comparative Study of Protocols for Mouse Embryonic Stem Cell Culturing," PLoS ONE, 2013, 8(12):e81156, 10 pgs.
Tamminen, K., et al., "Intestinal Commitment and Maturation of Human Pluripotent Stem Cells Is Independent of Exogenous FGF4 and R-spondin1," PLOS One, Jul. 2015, 10(7):e0134551, 19 pgs.
Terry, B.S., et al., "Preliminary Mechanical Characterization of the Small Bowel for In Vivo Robotic Mobility," J. Biomech Eng, 2011, 133:091010-1-09101-7, 7 pgs.
The WNT homepage, "Small molecules in Wnt signalling," Nusse Lab, Jan. 2019, 2 pgs.
Theunissen, T.W., et al., "Systematic Identification of Culture Conditions for Induction and Maintenance of Naïve Human Pluripotency," Cell Stem Cell, 2014, 15:471-487, 47 pgs.
Tian, X., et al., "Modulation of Multidrug Resistance-Associated Protein 2 (Mrp2) and Mrp3 Expression and Function with Small Interfering RNA in Sandwich-Cultured Rat Hepatocytes," Mol Pharmacol, 2004, 66(4):1004-1010, 7 pgs.
Tran, K., et al. "Evaluation of regional and whole gut motility using the wireless motility capsule: relevance in clinical practice," Therap Adv Gastroenterol, 2012, 5(4):249-260, 12 pgs.
Trapnell, C., et al., "Transcript assembly and quantification by RNA-Seq reveals unannotated transcripts and isoform switching during cell differentiation," Nat Biotechnol, 2010, 28(5):511-515, 8 pgs.
Troy, D.B. (ed.), Remington: The Science and Practice of Pharmacy, 21$^{st}$ Ed., 2006, Lippincott, Williams & Wilkens, Baltimore, MD, 6 pgs., Table of Contents Only.
Tsedensodnom, O., et al., "ROS: Redux and Paradox in Fatty Liver Disease," Hepatology, 2013, 58(4):1210-1212, 3 pgs.
Tsukada, N., et al., "The Structure and Organization of the Bile Canalicular Cytoskeleton With Special Reference to Actin and Actin-Binding Proteins," Hepatology, 1995, 21(4):1106-1113, 8 pgs.
Tyml, K., et al., "Lipopolysaccharide reduces intercellular coupling in vitro and arteriolar conducted response in vivo," AJP-Heart Circ Physiol, 2001, 281:H1397-H1406, 10 pgs.
The United States Pharmacopeia: The National Fomulary (USP 24 NF 19), United States Pharmacopeial Convention, Inc., Rockville, MD, 1999, 4 pgs., Table of Contents Only.
Valadi, H., et al., "Exosome-mediated transfer of mRNAs and microRNAs is a novel mechanism of genetic exchange between cells," Nat Cell Biol, 2007, 9(6):654-659, 17 pgs.
Van De Garde, M.D., et al., "Liver Monocytes and Kupffer Cells Remain Transcriptionally Distinct during Chronic Viral Infection," PLoS One, 2016, 11(11):e0166094, 16 pgs.
Venick, R.S., et al., "Unique Technical and Patient Characteristics of Retransplantation: A Detailed Single Center Analysis of Intestinal Transplantation," International Small Bowel Symposium 2013; Abstract 5.203 (online: https://www.tts.org/component/%20tts/?view=presentation&id=13190), Accessed Jun. 12, 2017, 4 pgs.
Verma, S., et al., "Diagnosis, management and prevention of drug-induced liver injury," Gut, 2009, 58:1555-1564, 10 pgs.

(56) References Cited

OTHER PUBLICATIONS

Vosough, M., et al., "Generation of Functional Hepatocyte-Like Cells from Human Pluripotent Stem Cells in a Scalable Suspension Culture," Stem Cells Dev, 2013, 22(20):2693-2705, 13 pgs.

Wakayama, T., et al, "Full-term development of mice from enucleated oocytes injected with cumulus cell nuclei," Nature, 1998, 394:369-374, 6 pgs.

Wang, S., (Ed.), "The role of homologous genes in the development of appendages," in Basis of Developmental Biology, Press of East China University of Science and Technology, 2014, pp. 184-185, 4 pgs.

Wang, Y., et al., "Hepatic stellate cells, liver innate immunity, and hepatitis C virus," J Gastroenterol Hepatol, 2013, 28(Suppl 1):112-115, 8 pgs.

Want, R., "An Introduction to RFID Technology," IEEE Pervas Comput, 2006, 5:25-33, 9 pgs.

Ware, C.B., "Concise Review: Lessons from Naive Human Pluripotent Cells," Stem Cells, 2017, 35:35-41, 7 pgs.

Warren, C.R., et al., "Induced Pluripotent Stem Cell Differentiation Enables Functional Validation of GWAS Variants in Metabolic Disease," Cell Stem Cell, 2017, 20:547-557, 18 pgs.

Warren, C.R., et al., "The NextGen Genetic Association Studies Consortium: A Foray into In Vitro Population Genetics," Cell Stem Cell, 2017, 20:431-433, 3 pgs.

Wernig, M., et al., "In vitro reprogramming of fibroblasts into a pluripotent ES-cell-like state," Nature, 2007, 448:318-324, 8 pgs.

Wieck, M.M., et al., "Prolonged Absence of Mechanoluminal Stimulation in Human Intestine Alters the Transcriptome and Intestinal Stem Cell Niche," Cell Mol Gastroenterol Hepatol, 2017, 3(3):367-388e1, 23 pgs.

Wiley, L.A., et al., "cGMP production of patient-specific iPSCs and photoreceptors precursor cells to treat retinal degenerative blindness," Scientific Reports, 2016, 6:30742, 16 pgs.

Wilmut, I., et al., "Viable offspring derived from fetal and adult mammalian cells," Nature, 1997, 385:810-813, 4 pgs.

Xu, R., et al., "Association Between Patatin-Like Phospholipase Domain Containing 3 Gene (PNPLA3) Polymorphisms and Nonalcoholic Fatty Liver Disease: A HuGE Review and Meta-Analysis," Sci Rep, 2015, 5:9284, 11 pgs.

Xu, R., et al. (Eds.), "Retinoic acid receptor" in Basis and Clinic of Receptor, Shanghai Science and Technology Press, 1992, pp. 129-131, 2 pgs.

Yanagimachi, M.D., et al., "Robust and Highly-Efficient Differentiation of Functional Monocytic Cells from Human Pluripotent Stem Cells under Serum- and Feeder Cell-Free Conditions," PLoS One, 2013, 8(4):e59243, 9 pgs.

Yang, K., et al., "Systems Pharmacology Modeling Predicts Delayed Presentation and Species Differences in Bile Acid-Mediated Troglitazone Hepatotoxicity," Clin Pharmacol Ther, 2014, 96(5):589-598, 21 pgs.

Yoneda, M., et al., "Noninvasive assessment of liver fibrosis by measurement of stiffness in patients with nonalcoholic fatty liver disease (NAFLD)," Dig Liver Dis, 2008, 40:371-378, 8 pgs.

Yu, H., et al., "The Contributions of Human Mini-Intestines to the Study of Intestinal Physiology and Pathophysiology," Annu Rev Physiol, 2017, 79:291-312, 22 pgs.

Zain, S.M., et al., "A common variant in the glucokinase regulatory gene rs780094 and risk of nonalcoholic fatty liver disease: A meta-analysis," J Gastroenterol Hepatol, 2015, 30:21-27, 7 pgs.

Zambrano, E., et al., "Total parenteral Nutrition Induced Liver Pathology: An Autopsy Series of 24 Newborn Cases," Pediatr Dev Pathol, 2004, 7:425-432, 8 pgs.

Zborowski, J., et al., "Induction of swelling of liver mitochondria by fatty acids of various chain length," Biochim Biophys Acta, 1963, 70:596-598, 3 pgs.

Zhang, R-R., et al., "Human iPSC-Derived Posterior Gut Progenitors Are Expandable and Capable of Forming Gut and Liver Organoids," Stem Cell Reports, 2018, 10(3):780-793, 14 pgs.

Zhao, Y., et al., "A XEN-like State Bridges Somatic Cells to Pluripotency during Chemical Reprogramming," Cell, 2015, 163:1678-1691, 15 pgs.

Zhong, J., et al., "Continuous-wave laser-assisted injection of single magnetic nanobeads into living cells," Sensors and Actuators B: Chemical, 2016, 230:298-305, 8 pgs.

Chinese Office Action, the Second Office Action, and Supplementary Search Report, dated Dec. 19, 2019 for Application No. CN 201580034910.4, 11 pgs.

European Search Report and Written Opinion dated Oct. 31, 2019 for Application No. EP 17793451.0, 11 pgs.

International Search Report and Written Opinion dated Jul. 9, 2018 for Application No. PCT/US2018/027585, 12 pgs.

International Search Report and Written Opinion dated May 7, 2019 for Application No. PCT/US2018/067057, 15 pgs.

International Search Report and Written Opinion dated Oct. 29, 2019 for Application No. PCT/US2019/041985, 13 pgs.

International Search Report and Written Opinion dated Dec. 5, 2019 for Application No. PCT/US2019/050846, 10 pgs.

International Search Report and Written Opinion dated Dec. 13, 2019 for Application No. PCT/US2019/053408, 10 pgs.

U.S. Appl. No. 16/346,190, filed Apr. 30, 2019, by Takebe et al., entitled: "Liver Organoid Disease Models and Methods of Making and Using Same."

U.S. Appl. No. 16/599,620, filed Oct. 11, 2019, by Wells et al., entitled: "Methods and Systems for Converting Precursor Cells Into Intestinal Tissues Through Directed Differentiation."

U.S. Appl. No. 16/603,611, filed Oct. 8, 2019, by Mahe et al., entitled: "Methods of Making Improved Human Intestinal Organoid Compositions via Application of Strain and Human Intestinal Organoid Compositions Thereof."

U.S. Appl. No. 16/611,998, filed Nov. 8, 2019, by Takebe et al., entitled: "Liver Organoid Compositions and Methods of Making and Using Same."

Ahnfelt-Ronne, J., et al., "An improved method for three-dimensional reconstruction of protein expression patterns in intact mouse and chicken embryos and organs," J. Histochem. Cytochem., 2007, 55:925-930, 6 pgs.

Aronson, B.E., et al., "GATA4 represses an ileal program of gene expression in the proximal small intestine by inhibiting the acetylation of histone H3, lysine 27," Biochim, Biophys. Acta, 2014, 1839(11):1273-1282, 31 pgs.

Bartfeld, S., et al., "In Vitro Expansion of Human Gastric Epithelial Stem Cells and Their Responses to Bacterial Infection," Gastroenterology, Jan. 2015, 148(1):126-136, 22 pgs.

Battle, M.A., et al., "GATA4 is essential for jejunal function in mice," Gastroenterology, 2008, 135:1676-1686, 17 pgs.

Bernstein, B.E., et al., "The NIH Roadmap Epigenomics Mapping Consortium," Nat. Biotechnol. 2010; 28(10):1045-1048, 9 pgs.

Beuling, E., et al., "Co-Localization of Gata4 and Hnf1α in the Gastrointestinal Tract is Restricted to the Distal Stomach and Proximal Small Intestine," Gastroenterology, AGA Abstracts, Abstract T1933, 2007a, 132:A586, 1 pg.

Beuling, E., et al., "Conditional Gata4 deletion in mice induces bile acid absorption in the proximal small intestine," Gut, 2010, 59(7):888-895, 19 pgs.

Beuling, E., et al., "Fog Cofactors Partially Mediate Gata4 Function in the Adult Mouse Small Intestine," Gastroenterology, AGA Abstracts, Abstract W1467, 2007b, 132:A692-A693, 2 pgs.

Beuling, E., et al., "GATA4 mediates gene repression in the mature mouse small intestine through interactions with Friend of GATA (FOG) cofactors," Dev Biol, 2008a, 322(1):179-189, 23 pgs.

Beuling, E., et al., "The Absence of GATA4 in the Distal Small Intestine Defines the Ileal Phenotype," Gastroenterology, ABA Abstract, Abstract 602, 2008b, 134:A83-A84, 2 pgs.

Bonilla-Claudio, M., et al., "Bmp signaling regulates a dose-dependent transcriptional program to control facial skeletal development," Development, 2012, 139:709-719, 11 pgs.

Bosse, T., et al., "Gata4 and Hnf1α are partially required for the expression of specific intestinal genes during development," Am J Physiol Gastrointest Liver Physiol, 2007, 292:G1302-G1314, 13 pgs.

Bouchi, R., et al., "FOXO1 Inhibition Yields Functional Insulin-Producing Cells In Human Gut Organoid Cultures," Nat Commun, 2014, 5:4242, 24 pgs.

(56) References Cited

OTHER PUBLICATIONS

Burnicka-Turek, O., et al., "INSL5-Deficient Mice Display an Alteration in Glucose Homeostasis and an Impaired Fertility," Endocrinology, Oct. 2012, 153(10):4655-4665, 11 pgs.

Choi, E., et al., "Cell lineage distribution atlas of the human stomach reveals heterogeneous gland populations in the gastric antrum," Gut, 2014, 63(11):1711-1720, 20 pgs.

Choi, E., et al., "Expression of Activated Ras in Gastric Chief Cells of Mice Leads to the Full Spectrum of Metaplastic Lineage Transitions," Gastroenterology, Apr. 2016, 150(4):918-930, 23 pgs.

De Santa Barbara, P., et al., "Bone Morphogenetic Protein Signaling Pathway Plays Multiple Roles During Gastrointestinal Tract Development," Developmental Dynamics, 2005, 234:312-322, 11 pgs.

Dobreva, G., et al., "SATB2 Is a Multifunctional Determinant of Craniofacial Patterning and Osteoblast Differentiation," Cell, 2006, 125:971-986, 16 pgs.

Driver, I., et al., "Specification of regional intestinal stem cell identity during *Drosophila* metamorphosis," Development, 2014, 141:1848-1856, 9 pgs.

Duluc, I., et al., "Fetal Endoderm Primarily Holds the Temporal and Positional Information Required for Mammalian Intestinal Development," The Journal of Cell Biology, 1994, 126(1):211-221, 11 pgs.

Fagerberg, L., et al., "Analysis of the Human Tissue-specific Expression by Genome-wide Integration of Transcriptomics and Antibody-based Proteomics," Mol Cell Proteomics, 2014, 13:397-406, 10 pgs.

Finkbeiner, S.R., et al., "Transcriptome-Wide Analysis Reveals Hallmarks of Human Intestine Development and Maturation In Vitro and In Vivo," Stem Cell Reports, 2015, 4:1140-1155, 16 pgs.

Fitzpatrick, D.R., et al., "Identification of SATB2 as the cleft palate gene on 2q32-q33," Human Molecular Genetics, 2003, 12(19):2491-2501, 11 pgs.

Genthe, J.R., et al., "Ventromorphins: A new class of small molecule activators of the canonical BMP signaling pathway," ACS Chem Biol, 2017, 12(9):2436-2447, 21 pgs.

Georgas, K.M., et al., "An illustrated anatomical ontology of the developing mouse lower urogenital tract," Development, 2015, 142:1893-1908, 16 pgs.

Ginestet, C., Book Review in the Journal of the Royal Statistical Society. Series A (Statistics in Society) (2011), of ggplot2: Elegant Graphics for Data Analysis, by H. Wickham, 2009; 174(1):245, 2 pgs.

Goldenring, J.R., et al., "Differentiation of the Gastric Mucosa: III. Animal models of oxyntic atrophy and metaplasia," Am J Physiol Gastrointestinal and Liver Physiol, 2006, 291:G999-G1004, 6 pgs.

Goldenring, J.R., et al., "Overexpression of Transforming Growth Factor-α Alters Differentiation of Gastric Cell Lineages," Dig. Dis. Sci., 1996, 41(4):773-784, 12 pgs.

Guo, Z., et al., "Injury-induced BMP signaling negatively regulates *Drosophila* midgut homeostasis," J Cell Biol., 2013, 201(6):945-961, 17 pgs.

Gyorgy, A.B., et al., "SATB2 interacts with chromatin-remodeling molecules in differentiating cortical neurons" European Journal of Neuroscience, 2008, 27:865-873, 9 pgs.

Haramis, A-P.G., et al., "De Novo Crypt Formation and Juvenile Polyposis on BMP Inhibition in Mouse Intestine," Science, 2004, 303:1684-1686, 4 pgs.

Hardwick, J.C.H., et al., "Bone Morphogenetic Protein 2 Is Expressed by, and Acts Upon, Mature Epithelial Cells in the Colon," Gastroenterology, 2004, 126:111-121, 11 pgs.

He, X.C., et al., "BMP signaling inhibits intestinal stem cell self-renewal through suppression of Wnt-β-catenin signaling," Nature Genetics, 2004, 36(10):1117-1121, 5 pgs.

Higuchi, Y., et al., "Gastrointestinal Fibroblasts Have Specialized, Diverse Transcriptional Phenotypes: A Comprehensive Gene Expression Analysis of Human Fibroblasts," PloS One, Jun. 2015, 10(6):e0129241, 19 pgs.

Hoffmann, W., "Current Status on Stem Cells and Cancers of the Gastric Epithelium," Int. J. Mol. Sci., 2015, 16:19153-19169, 17 pgs.

Holland, P.W.H., et al., "Classification and nomenclature of all human homeobox genes," BMC Biology, 2007, 5:47, 29 pgs.

Huh, W.J., et al., "Ménétrier's Disease: Its Mimickers and Pathogenesis," Journal of Pathology and Translational Medicine, 2016; 50:10-16, 7 pgs.

Jeejeebhoy, K.N., "Shortbowel syndrome: a nutritional and medical approach," CMAJ, 2002, 166(10):1297-1302, 6 pgs.

Johnston, T.B., et al., "Extroversion of the Bladder, Complicated by the Presence of Intestinal Openings on the Surface of the Extroverted Area," J Anat Physiol, 1913, 48(Pt 1):89-106, 18 pgs.

Keeley, T.M., et al., "Cytodifferentiation of the postnatal mouse stomach in normal and Huntingtin-interacting protein 1-related-deficient mice," Am. J. Physiol. Gastrointest. Liver Physiol., 2010, 299:G1241-G1251, 11 pgs.

Kim, B-M., et al., "Regulation of mouse stomach development and Barx1 expression by specific microRNAs," Development, 2011, 138:1081-1086, 6 pgs.

Kim, B-M., et al., "The Stomach Mesenchymal Transcription Factor Barx1 Specifies Gastric Epithelial Identity through Inhibition of Transient Wnt Signaling," Developmental Cell, 2005, 8:611-622, 12 pgs.

Kohlnhofer, B.M., et al., "GATA4 Regulates Epithelial Cell Proliferation to Control Intestinal Growth and Development in Mice," Cellular and Molecular Gastroenterology and Hepatology, 2016, 2(2):189-209, 21 pgs.

Kraus, M.R.C., et al., "Patterning and shaping the endoderm in vivo and in culture," Current Opinion Genetics & Development., 2012, 22:347-353, 7 pgs.

Lambrecht, N.W.G., et al., "Identification of the K efflux channel coupled to the gastric H-K-ATPase during acid secretion," Physiological Genomics, 2005, 21:81-91, 11 pgs.

Lameris, A.L., et al., "Expression profiling of claudins in the human gastrointestinal tract in health and during inflammatory bowel disease," Scandinavian Journal of Gastroenterology, 2013, 48:58-69, 12 pgs.

Langmead, G., et al., "Ultrafast and memory-efficient alignment of short DNA sequences to the human genome," Genome Biology, 2009, 10:R25, 10 pgs.

Lennerz, J.K.M., et al., "The Transcription Factor MIST1 Is a Novel Human Gastric Chief Cell Marker Whose Expression Is Lost in Metaplasia, Dysplasia, and Carcinoma," The American Journal of Pathology, 2010, 177(3):1514-1533, 20 pgs.

Li, H., et al., "TreeFam: a curated database of phylogenetic trees of animal gene families," Nucleic Acids Research, 2006, 34:D572-D580, 9 pgs.

Li, L., "BMP Signaling Inhibits Intestinal Stem Cell Self-Renewal Through Antagonizing Wnt Signaling," Gastroenterology, AASLD Abstracts, Abstract S1223, 2005, 128:A702, 1 pg.

McGovern, D.P.B., et al., "Genome-wide association identifies multiple ulcerative colitis susceptibility loci," Nature Genetics, 2010, 42(4):332-337, 8 pgs.

Molodecky, N.A., et al., "Increasing Incidence and Prevalence of the Inflammatory Bowel Diseases With Time, Based on Systematic Review," Gastroenterology, 2012, 142:46-54, 51 pgs.

Moser, A.R., et al., "A dominant mutation that predisposes to multiple intestinal neoplasia in the mouse," Science, 1990, 247(4940):322-324, 3 pgs.

Nielsen, C., et al., "Gizzard Formation and the Role of Bapx1," Developmental Biology, 2001, 231:164-174, 11 pgs.

Nomura, S., et al., "Evidence for Repatterning of the Gastric Fundic Epithelium Associated With Ménétrier's Disease and TGFα Overexpression," Gastroenterology, 2005, 128:1292-1305, 14 pgs.

Park, Y.H., et al., "Review of Atrophic Gastritis and Intestinal Metaplasia as a Premalignant Lesion of Gastric Cancer," Journal of Cancer Prevention, 2015, 20(1):25-40, 16 pgs.

Patankar, J.V., et al., "Intestinal Deficiency of Gata4 Protects from Diet-Induced Hepatic Steatosis by Suppressing De Novo Lipogenesis and Gluconeogenesis in Mice," Journal of Hepatology, Posters, Abstract 1253, 2012, 56:S496, 1 pg.

(56) References Cited

OTHER PUBLICATIONS

Patankar, J.V., et al., "Intestinal GATA4 deficiency protects from diet-induced hepatic steatosis," Journal of Hepatology, 2012, 57:1061-1068, 8 pgs.
Ramalingam, S., et al., "Distinct levels of Sox9 expression mark colon epithelial stem cells that form colonoids in culture," Am J Physiol Gastrointest Liver Physiol,, 2012, 302:G10-G20, 11 pgs.
Ramsey, V.G., et al., "The maturation of mucus-secreting gastric epithelial progenitors into digestive-enzyme secreting zymogenic cells requires Mist1," Development, 2007, 134:211-222, 12 pgs.
Rankin, S.A., et al., "A Molecular Atlas of Xenopus Respiratory System Development," Developmental Dynamics, 2015, 244:69-85, 17 pgs.
Rankin, S.A., et al., "Suppression of Bmp4 signaling by the zinc-finger repressors Osr1 and Osr2 is required for Wnt/β-catenin-mediated lung specification in Xenopus," Development, 2012, 139:3010-3020, 11 pgs.
Ratineau, C., et al., "Endoderm- and mesenchyme-dependent commitment of the differentiated epithelial cell types in the developing intestine of rat," Differentiation, 2003, 71:163-169, 7 pgs.
Roberts, D.J., et al., "Sonic hedgehog is an endodermal signal inducing Bmp-4 and Hox genes during induction and regionalization of the chick hindgut," Development, 1995, 121:3163-3174, 12 pgs.
Rodríguez-Piñeiro, A.M., et al., "Studies of mucus in mouse stomach, small intestine, and colon. II. Gastrointestinal mucus proteome reveals Muc2 and Muc5ac accompanied by a set of core proteins," Am J Physiol Gastrointest Liver Physiol, 2013, 305:G348-G356, 9 pgs.
Rodriquez, P., et al., "BMP signaling in the development of the mouse esophagus and forestomach," Development, 2010, 137:4171-4176, 6 pgs.
Roth, R.B., et al., "Gene expression analyses reveal molecular relationships among 20 regions of the human CNS," Neurogenetics, 2006, 7:67-80, 14 pgs.
Savidge, T.C., et al., "Human intestinal development in a severe-combined immunodeficient xenograft model," Differentiation, 1995, 58:361-371, 11 pgs.
Savin, T., et al., "On the growth and form of the gut," Nature, 2011, 476:57-62, 7 pgs.
Schumacher, M.A., et al., "The use of murine-derived fundic organoids in studies of gastric physiology," J. Physiol., 2015, 593(8):1809-1827, 19 pgs.
Sheehan-Rooney, K., et al., "Bmp and Shh Signaling Mediate the Expression of satb2 in the Pharyngeal Arches," PLoS One, Mar. 2013, 8(3):e59533, 10 pgs.
Sherwood, R.I., et al., "Transcriptional dynamics of endodermal organ formation," Dev Dyn, 2009, 238(1):29-42, 23 pgs.
Sherwood, R.I., et al., "Wnt signaling specifies and patterns intestinal endoderm," Mechanisms of Development, 2011, 128:387-400, 14 pgs.
Shyer, A.E., et al., "Bending Gradients: How the Intestinal Stem Cell Gets Its Home," Cell, 2015, 161:569-580, 13 pgs.
Siegel, R., et al., "Colorectal Cancer Statistics, 2014," CA Cancer J Clin, 2014, 64:104-117, 14 pgs.
Sigalet, D.L., "The Role of the Enteric Neuronal System In Controlling Intestinal Function," Clinical Surgery Society Magazine, 2003, 64:214. (Reference unavailable).
Speer, A.L., et al., "Fibroblast Growth Factor 10-Fibroblast Growth Factor Receptor 2b Mediated Signaling Is Not Required for Adult Glandular Stomach Homeostasis," PLoS ONE, 2012, 7(11):e49127, 12 pgs.
Stange, D.E., et al., "Differentiated Troy+ chief cells act as 'reserve' stem cells to generate all lineages of the stomach epithelium," Cell, 2013, 155(2):357-368, 26 pgs.
Thanasupawat, T., et al., "INSL5 is a novel marker for human enteroendocrine cells of the large intestine and neuroendocrine tumours," Oncology Reports, 2013, 29:149-154, 6 pgs.
Trapnell, C., et al., "Differential gene and transcript expression analysis of RNA-seq experiments with TopHat and Cufflinks," Nat Protoc, 2013, 7(3):562-578, 39 pgs.
Uppal, K., et al., "Meckel's Diverticulum: A Review," Clinical Anatomy, 2011, 24: 416-422, 7 pgs.
Van Dop, W.A., et al., "Depletion of the Colonic Epithelial Precursor Cell Compartment Upon Conditional Activation of the Hedgehog Pathway," Gastroenterology, 2009, 136:2195-2203, 16 pgs.
Van Klinken, B.J-W., et al., "MUC5B is the prominent mucin in human gallbladder and is also expressed in a subset of colonic goblet cells," The American Journal of Physiology, 1998, 274:G871-G878, 8 pgs.
Walker, E.M., et al., "GATA4 and GATA6 regulate intestinal epithelial cytodifferentiation during development," Developmental Biology, 2014, 392:283-294, 12 pgs.
Walton, K.D., et al., "Epithelial Hedgehog signals direct mesenchymal villus patterning through BMP," Abstracts / Developmental Biology, Program/Abstract # 354, 2009, 331:489, 1 pg.
Walton, K.D., et al., "Hedgehog-responsive mesenchymal clusters direct patterning and emergence of intestinal villi," PNAS, 2012, 109(39):15817-15822, 6 pgs.
Walton, K.D., et al., "Villification in the mouse: Bmp signals control intestinal villus patterning," Development, 2016, 143:427-436, 10 pgs.
Wang, X., et al., "Cloning and variation of ground state intestinal stem cells," Nature, 2015, 522:173-178, 18 pgs.
Wehkamp, J., et al., "Paneth cell antimicrobial peptides: Topographical distribution and quantification in human gastrointestinal tissues," FEBS Letters, 2006, 580:5344-5350, 7 pgs.
Weis, V.G., et al., "Current understanding of SPEM and its standing in the preneoplastic process," Gastric Cancer, 2009, 12:189-197, 9 pgs.
Whissell, G., et al., "The transcription factor GATA6 enables self-renewal of colon adenoma stem cells by repressing BMP gene expression," Nature Cell Biology, 2014, 16(7):695-707, 24 pgs.
Wills, A., et al., "Bmp signaling is necessary and sufficient for ventrolateral endoderm specification in Xenopus," Dev Dyn., 2008, 237(8):2177-2186, 18 pgs.
Xue, X., et al., "Endothelial PAS Domain Protein 1 Activates the Inflammatory Response in the Intestinal Epithelium to Promote Colitis in Mice," Gastroenterology, 2013, 145:831-841, 11 pgs.
Yahagi, N., et al., "Position-specific expression of Hox genes along the gastrointestinal tract," Congenital Anomalies, 2004, 44:18-26, 9 pgs.
Zbuk, K.M., et al., "Hamartomatous polyposis syndromes," Gastroenterology & Hepatology, 2007, 4(9):492-502, 12 pgs.
Japanese Office Action, Notification of Reasons for Refusal, and First Search Report by Registered Search Organization, dated May 14, 2019 for Application JP 2017-520900, 65 pgs.
Japanese Office Action, Notice of Reasons for Refusal, and Search Report by Registered Search Organization, dated Apr. 2, 2019 for Application No. JP 2016-569618, 42 pgs.
Singaporean Office Action, Third Written Opinion, dated May 3, 2019 for Application No. SG 11201609953X, 5 pgs.
An, W.F., et al., "Discovery of Potent and Highly Selective Inhibitors of GSK3b," Molecular Libraries, Probe Report, May 2014, 115 pgs.
Chang, H-M., et al., "BMP15 Suppresses Progesterone production by Down-Regulating StAR via ALK3 in Human Granulosa Cells," Molecular Endocrinology, 2013, 27:2093-2104, 12 pgs.
Deng, H., "Mechanisms of retinoic acid on the induction of differentiation of neural stem cells for newborn rat striatum," Chinese Doctoral and Master Dissertations Full-Text Database (Doctoral) Basic Science, Issue 4, Apr. 15, 2006, pp. 1-89. Reference unavailable.
Deng, H. et al., "Effects of all-trans retinoic acid on the differentiation of neural stem cells and the expression of c-myc gene," Chinese Journal of Tissue Engineering Research, Mar. 18, 2007, 11(11):2039-2042. Reference unavailable.
Krausova, M., et al., "Wnt signaling in adult intestinal stem cells and cancer," Cellular Signalling, 2014, 26:570-579, 10 pgs.

(56) References Cited

OTHER PUBLICATIONS

Lim, D.A., et al., "Noggin Antagonizes BMP Signaling to Create a Niche for Adult Neurogenesis," Neuron, Dec. 2000, 28:713-726, 14 pgs.

McMahon, J.A., et al., "Noggin-mediated antagonism of BMP signaling is required for growth and patterning of the neural tube and somite," Genes & Development, May 1998, 12:1438-1452, 15 pgs.

Ornitz, D.M., et al., "FGF signaling pathways in endochondral and intramembranous bone development and human genetic disease," Genes & Development, Jun. 2002, 16:1446-1465, 21 pgs.

Pan, Q., *Physiology*, University of Science and Technology of China Press, Jan. 31, 2014, pp. 149-150. Reference unavailable.

Que, J., et al., "Morphogenesis of the trachea and esophagus: current players and new roles for noggin and Bmps," Differentiation, 2006, 74:422-437, 16 pgs.

Raju, R., et al., "A Network Map of FGF-1/FGFR Signaling System," Journal of Signal Transduction, Apr. 2014, 2014:1-16, Article ID 962962, 16 pgs.

Su, N., et al., "Role of FGF/FGFR signaling in skeletal development and homeostasis: learning from mouse models," Bone Research, 2014, 2:14003, 24 pgs.

Wan, W., et al., "The Role of Wnt Signaling in the Development of Alzheimer's Disease: A Potential Therapeutic Target?", BioMed Research International, 2014, 2014:1-9, Article ID 301575, 9 pgs.

Yanagita, M., "Modulator of bone morphogenetic protein activity in the progression of kidney diseases," Kidney International, 2006, 70:989-993, 5 pgs.

Yu, Y., *Chinese Studies on Disease Signaling Pathway and Targeted Therapy*, Anhui Science and Technology Press, May 31, 2013, p. 363. Reference unavailable.

Chinese Office Action, and Preliminary Search Report, dated Jan. 30, 2019 for Application No. CN 201580034910.4, 11 pgs.

Israeli Office Action dated Nov. 29, 2018 for Application No. IL 249253, 8 pgs.

Buta, C., et al., "Reconsidering pluripotency tests: Do we still need teratoma assays?" Stem Cell Research, 2013, 11:552-562, 11 pgs.

Fon Tacer, K., et al., "Research Resource: Comprehensive Expression Atlas of the Fibroblast Growth Factor System in Adult Mouse," Mol Endocrinol, Oct. 2010, 24(10):2050-2064, 15 pgs.

Gomez, M.C., et al., "Derivation of cat embryonic stem-like cells from in vitro-produced blastocysts on homologous and heterologous feeder cells," Theriogenology, 2010, 74:498-515, 18 pgs.

Jean, C., et al., "Pluripotent genes in avian stem cells," Develop Growth Differ, 2013, 55:41-51, 11 pgs.

Ornitz, D.M., et al., "The Fibroblast Growth Factor signaling pathway," WIREs Dev Biol, 2015, 4:215-266, 52 pgs.

Prakash, R., "Regulation of WNT Genes in Stem Cells Development and Organogenesis," IJP, Jun. 2014, 1(6):366-372, 7 pgs.

International Search Report and Written Opinion dated Sep. 28, 2018 for Application No. PCT/US2018/029083, 14 pgs.

U.S. Appl. No. 62/730,061, filed Sep. 12, 2018.

Deward, A.D., et al., "Cellular Heterogeneity in the Mouse Esophagus Implicates the Presence of a Nonquiescent Epithelial Stem Cell Population," Cell Reports, 2014, 9:701-711, 12 pgs.

Trisno, S.L., et al., "Esophageal Organoids from Human Pluripotent Stem Cells Delineate Sox2 Functions during Esophageal Specification," Cell Stem Cell, 2018, 23:501-515, 23 pgs.

International Search Report and Written Opinion dated Jan. 8, 2019 for Application No. PCT/US2018/054635, 16 pgs.

Bain G., "Embryonic Stem Cells Express Neuronal Properties in Vitro," Developmental Biology, 1995, vol. 168, pp. 842-357.

Burns A.J., et al., "Enteric Nervous System Development: Analysis of the Selective Developmental Potentialities of Vagal and Sacral Neural Crest Cells using Quail-Chick Chimeras," The Anatomical Record, 2001, vol. 262, pp. 16-28.

Burrin D., et al., "Enteral Obeticholic Acid Prevents Hepatic Cholestasis in Total Parenteral Nutrition-Fed Neonatal Pigs", Hepatology, vol. 62, Oct. 2015, p. 307A.

Chauhan R.K., et al., "Genetic and Functional Studies of Hirschsprung Disease", Doctoral Thesis: Department of Clinical Genetics, Erasmus University Rotterdam, the Netherlands, 2016; 202 pages.

Cunningham T.J., et al., "Mechanisms of Retinoic Acid Signalling and its Roles in Organ and Limb Development", Nature Reviews Molecular Cell Biology, vol. 16, No. 2, Jan. 5, 2015, pp. 110-123.

Dunn, "Cationic Nanoparticles for the Targeting and Delivery of Nucleic Acids to the Pulmonary Endothelium," University of Cincinnati, Sep. 19, 2018, Doctoral Thesis; downloaded from https://etd.ohiolink.edu/apexprod/rws olink/r/1501/10?clear=10&p10 accession num=ucin1544 098242321181; 160 pages.

Goldstein A.M., et al., "BMP Signaling is Necessary for Neural Crest Cell Migration and Ganglion Formation in the Enteric Nervous System", Mechanisms of Development, 2005, vol. 122, pp. 821-833.

Guan Y., et al., "Human Hepatic Organoids for the Analysis of Human Genetic Diseases", JCI Insight, Sep. 7, 2017, vol. 2, Issue 17, e94954; 17 pages.

Huang H., "Differentiation of Human Embryonic Stem Cells into Smooth Muscle Cells in Adherent Monolayer Culture", Biochemical and Biophysical Research Communications, 2006, vol. 351 pp. 321-327.

Jones P., et al., "Stromal Expression of Jagged 1 Promotes Colony Formation by Fetal Hematopoietic Progenitor Cells", Blood, 1 Sep. 1998, vol. 92, No. 5, pp. 1505-1511.

Kruitwagen H.S., et al., "SCH-O-5 Long-Term Adult Feline Liver Organoid Cultures for Disease Modelling of Hepatic Lipidosis," Research Communications of the 26th ECVIM-CA Congress, Sep. 2016, ECVIM Abstracts pp. 203-204.

Kruitwagen H.S., et al., "Long-Term Adult Feline Liver Organoid Cultures for Disease Modeling of Hepatic Steatosis", Stem Cell Reports, Apr. 2017, vol. 8(4), pp. 822-830.

Lachmann N., et al., "Large-Scale Hematopoietic Differentiation of Human Induced Pluripotent Stem Cells Provides Granulocytes or Macrophages for Cell Replacement Therapies," Stem Cell Report, Feb. 10, 2015, vol. 4, pp. 282-296.

Lai F.P-L., et al., "Correction of Hirschsprung-Associated Mutations in Human Induced Pluripotent Stem Cells Via Clustered Regularly Interspaced Short Palindromic Repeats/Cas9, Restores Neural Crest Cell Function," Gastroenterology, 2017, vol. 153, No. 1, pp. 139-153.

Liu J.A-J., et al., "Identification of GLI Mutations in Patients with Hirschsprung Disease that Disrupt Enteric Nervous System Development in Mice," Gastroenterology, 2015, vol. 149, No. 7, pp. 1837-1848.

McCracken K.W., et al., "Generating Human Intestinal Tissue from Pluripotent Stem Cells in Vitro," Nature Protocols, vol. 6, No. 12, Nov. 10, 2011, pp. 1920-1928.

McCracken K.W., et al., "Modelling Human Development and Disease in Pluripotent Stem-Cell-Derived Gastric Organoids," Nature, Oct. 29, 2014, vol. 516, No. 7531, pp. 400-404.

Mori R., et al., "Micropatterned Organoid Culture of Rat Hepatocytes and HepG2 Cells," Journal of Bioscience and Bioengineering, Sep. 2008, vol. 106(3), pp. 237-242.

Nantasanti S., et al., "Concise Review: Organoids are a Powerful Tool for the Study of Liver Disease and Personalized Treatment Design in Humans and Animals: Organoids for Disease Modeling and Therapy", Stem Cells Translational Medicine, Jan. 21, 2016, vol. 5(3), pp. 325-330.

Okada Y., et al., "Retinoic-Acid-Concentration-Dependent Acquisition of Neural Cell Identity during in Vitro Differentiation of Mouse Embryonic Stem Cells," Developmental Biology, 2004, vol. 275, Issue 1, pp. 124-142.

Paddison P.J., et al., "Short Hairpin Activated Gene Silencing in Mammalian Cells", Methods in Molecular Biology, 2004, vol. 265, pp. 85-100.

Ricchi M., et al., "Differential Effect of Oleic and Palmitic Acid on Lipid Accumulation and Apoptosis in Cultured Hepatocytes", Journal of Gastroenterology and Hepatology, May 2009, vol. 24, Issue 5, pp. 830-840.

Sherwood, et al., "Transcriptional Dynamics of Endodermal Organ Formation", Developmental Dynamics, Jan. 2009, vol. 238, Issue 1, pp. 29-42.

(56) References Cited

OTHER PUBLICATIONS

Siller R., et al., "Small-Molecule-Driven Hepatocyte Differentiation of Human Pluripotent Stem Cells", Stem Cell Reports, May 2015, vol. 4, No. 5, pp. 939-952.
Simkin J.E., et al., "Retinoic Acid Upregulates Ret and Induces Chain Migration and Population Expansion in Vagal Neural Crest Cells to Colonise the Embryonic Gut", PLoS ONE, May 2013, vol. 8(5), e64077, pp. 1-12.
Takebe T., et al., "Generation of a Vasularized and Functional Human Liver from an iPSC-derived Organ Bud Transplant," Nature Protocols, Feb. 2014, vol. 9(2), pp. 396-409.
Takebe T., et al., "Vascularized and Functional Human Liver from an iPSC-derived Organ bud Transplant," Nature, Jul. 25, 2013, vol. 499(7459), pp. 481-484.
Vu J., et al., "Regulation of Appetite, Body Composition and Metabolic Hormones by Vasoactive Intestinal Polypeptide (VIP)", Journal of Molecular Neuroscience, Apr. 23, 2015, vol. 56, No. 2, pp. 377-387.
Yamaguchi Y., et al., "Purified Interleukin 5 Supports the Terminal Differentiation and Proliferation of Murine Eosinophilic Precursors," Journal of Experimental Medicine, Jan. 1988, vol. 167, No. 1, pp. 43-56.
Zhang H., et al., "The Existence of Epithelial-to-Mesenchymal Cells with the Ability to Support Hematopoiesis in Human Fetal Liver," Cell Biology International, Mar. 2005, vol. 29, No. 3, pp. 213-219.

1. *Fundus marker* - Investigation in mouse E14.5 mouse stomach regions

Experimental procedure

E14.5 mouse stomach dissection (n=12)

Known regional markers

New regional markers

T test : p<0.05 * , p<0.01  , p<0.001 *

Fundus specification protocol

2. Fundus specification – Wtn pathway influence

Results – Protocol 2

METHODS AND SYSTEMS FOR CONVERTING PRECURSOR CELLS INTO GASTRIC TISSUES THROUGH DIRECTED DIFFERENTIATION

PRIORITY CLAIM

This application claims priority to and benefit of U.S. patent application Ser. No. 15/312,939, filed Nov. 21, 2016, which claims priority to and benefit of PCT/US2015/032626, filed May 27, 2015, which claims priority to and benefit of U.S. Provisional Patent Application No. 62/003,719, to Wells et al, filed on May 28, 2014, entitled "Methods and Systems for Converting Precursor Cells into Gastric Tissues through Directed Differentiation" in their entirety and for all purposes.

STATEMENT REGARDING FEDERALLY-SPONSORED RESEARCH

This invention was made with government support under DK080823, DK092456, and GM063483 awarded by the National Institutes of Health. The government has certain rights to the invention.

FIELD OF THE INVENTION

Disclosed herein are methods and systems relating to converting stem cells into specific tissue(s) or organ(s) through directed differentiation. In particular, disclosed are methods and systems for promoting definitive endoderm formation from human pluripotent stem cells. Also disclosed are methods and systems for promoting gastric organoids or tissue formations from differentiated definitive endoderm.

BACKGROUND

Stomach function and architecture vary widely between mammalian species, to accommodate a wide variety of habitats and diets. Consequently, non-human models of gastric development and disease have significant limitations. For example, the bacterium *Helicobacter Pylori* infects 50% of the world's population, with 10% developing peptic ulcer disease and 1-2%[1-3] developing gastric cancer. Gastric diseases, including peptic ulcer disease and gastric cancer, affect 10% of the world's population and are largely due to chronic *H. pylori* infection. Current models of *H. pylori*-induced disease rely upon animal models that do not exhibit the same pathophysiological features as the human response to infection[4], and gastric cell lines lack the cellular and architectural complexity of the gastric epithelium in vivo. Thus there is no adequate model to study the effects of *H. pylori* infection as it occurs in humans. While recent advances using adult gastric stem cells allow for growth of rodent gastric epithelium in vitro[5], obtaining these cells from human patients would require surgery. Moreover, such a method could not be used to model embryonic development of the human stomach or stromal-epithelial interactions. Species differences in embryonic development and architecture of the adult stomach make murine models suboptimal for the study of organogenesis and pathogenesis of this organ. Thus, there is a need for robust in vitro systems for elucidating the mechanisms underlying human stomach development and disease and for the identification of novel treatments useful for human treatment of such diseases.

What is needed in the art are methods and systems for accurately controlling the destination of a precursor cell such as a human pluripotent stem cell, in order to create the specific type of tissue or organism desired, in particular, gastric tissues that can be used for one or more of the aforementioned purposes.

BRIEF SUMMARY

Disclosed are methods of inducing formation of a gastric cells and/or a gastric tissue, such as in the form of a gastric organoid. The formation of gastric cells and/or tissue may be carried out by the activating and/or inhibiting of one or more signaling pathways within a precursor cell. Also disclosed are methods for using the disclosed gastric cells, gastric tissues, and or gastric organoids derived from precursor cells.

BRIEF DESCRIPTION OF THE DRAWINGS

Those of skill in the art will understand that the drawings, described below, are for illustrative purposes only. The drawings are not intended to limit the scope of the present teachings in any way.

The patent or application file contains at least one drawing executed in color. Copies of this patent or patent application publication with color drawing(s) will be provided by the Office upon request and payment of the necessary fee.

DETAILED DESCRIPTION

Figure 1:
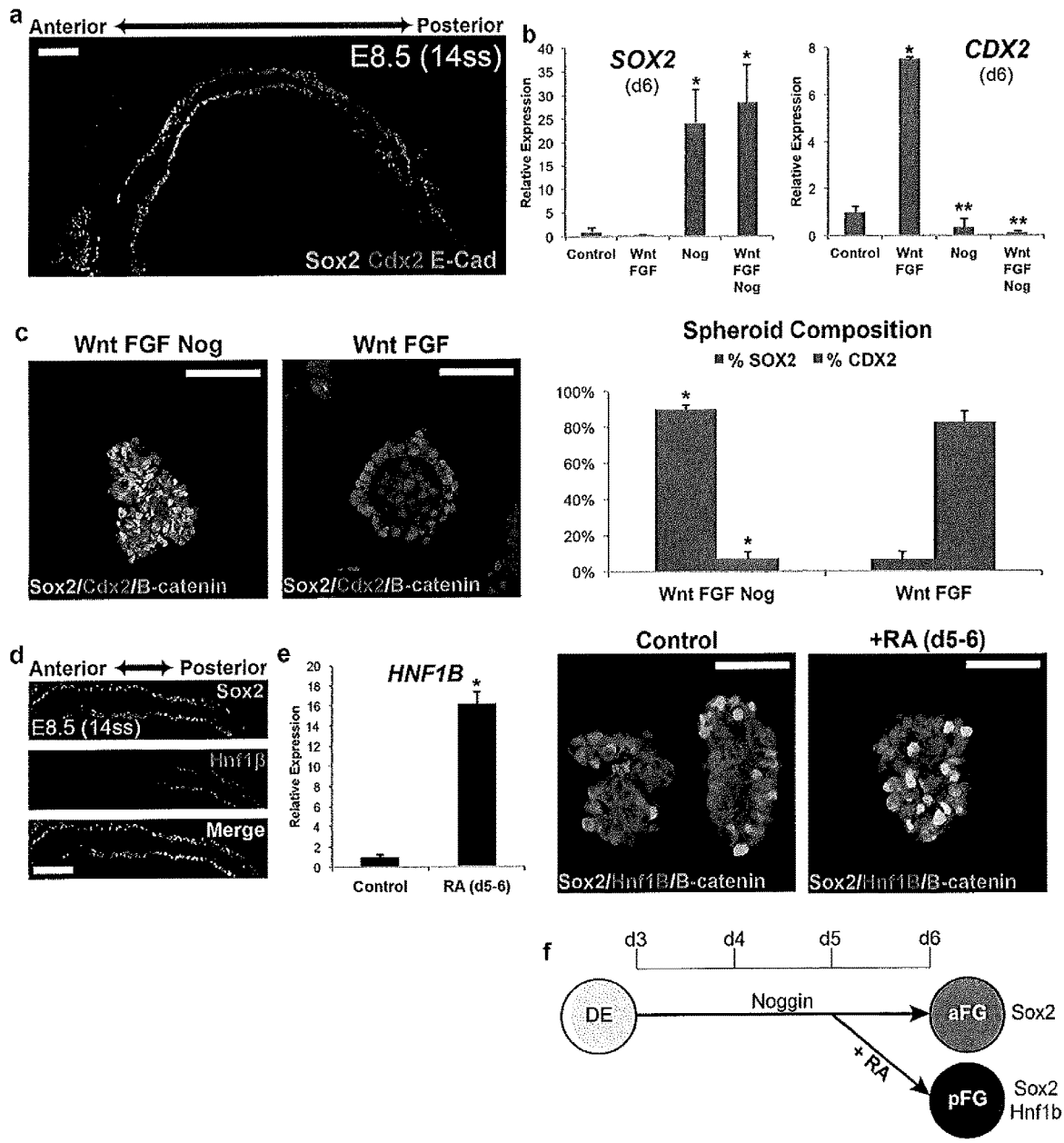
FIG. 1 depicts expression of Sox2/Cdx2/B-catenin in gastric spheroids and the effect of RA.

Unless otherwise noted, terms are to be understood according to conventional usage by those of ordinary skill in the relevant art.

As used herein, the term "totipotent stem cells" (also known as omnipotent stem cells) are stem cells that can differentiate into embryonic and extra-embryonic cell types. Such cells can construct a complete, viable, organism. These cells are produced from the fusion of an egg and sperm cell. Cells produced by the first few divisions of the fertilized egg are also totipotent.

As used herein, the term "pluripotent stem cells (PSCs)" encompasses any cells that can differentiate into nearly all cell types of the body, i.e., cells derived from any of the three germ layers (germinal epithelium), including endoderm (interior stomach lining, gastrointestinal tract, the lungs), mesoderm (muscle, bone, blood, urogenital), and ectoderm (epidermal tissues and nervous system). PSCs can be the descendants of inner cell mass cells of the primplantation blastocyst or obtained through induction of a non-pluripotent cell, such as an adult somatic cell, by forcing the expression of certain genes. Pluripotent stem cells can be derived from any suitable source, as will be readily understood by one of skill in the art. Examples of sources of pluripotent stem cells include mammalian sources, including human, rodent, porcine, bovine, but are not so limited.

As used herein, the term "induced pluripotent stem cells (iPSCs)," also commonly abbreviated as iPS cells, refers to a type of pluripotent stem cells artificially derived from a normally non-pluripotent cell, such as an adult somatic cell, by inducing a "forced" expression of certain genes.

As used herein, the term "embryonic stem cells (ESCs)," also commonly abbreviated as ES cells, refers to cells that are pluripotent and derived from the inner cell mass of the blastocyst, an early-stage embryo. For purpose of the present invention, the term "ESCs" is used broadly sometimes to encompass the embryonic germ cells as well.

As used herein, the term "precursor cell" encompasses any cells that can be used in methods described herein, through which one or more precursor cells acquire the ability to renew itself or differentiate into one or more specialized cell types. In some embodiments, a precursor cell is pluripotent or has the capacity to becoming pluripotent. In some embodiments, the precursor cells are subjected to the treatment of external factors (e.g., growth factors) to acquire pluripotency. In some embodiments, a precursor cell can be a totipotent (or omnipotent) stem cell; a pluripotent stem cell (induced or non-induced); a multipotent stem cell; an oligopotent stem cells and a unipotent stem cell. In some embodiments, a precursor cell can be from an embryo, an infant, a child, or an adult. In some embodiments, a precursor cell can be a somatic cell subject to treatment such that pluripotency is conferred via genetic manipulation or protein/peptide treatment.

In developmental biology, cellular differentiation is the process by which a less specialized cell becomes a more specialized cell type. As used herein, the term "directed differentiation" describes a process through which a less specialized cell becomes a particular specialized target cell type. The particularity of the specialized target cell type can be determined by any applicable methods that can be used to define or alter the destiny of the initial cell. Exemplary methods include but are not limited to genetic manipulation, chemical treatment, protein treatment, and nucleic acid treatment.

As used herein, the term "cellular constituents" are individual genes, proteins, mRNA expressing genes, and/or any other variable cellular component or protein activities such as the degree of protein modification (e.g., phosphorylation), for example, that is typically measured in biological experiments (e.g., by microarray or immunohistochemistry) by those skilled in the art. Significant discoveries relating to the complex networks of biochemical processes underlying living systems, common human diseases, and gene discovery and structure determination can now be attributed to the application of cellular constituent abundance data as part of the research process. Cellular constituent abundance data can help to identify biomarkers, discriminate disease subtypes and identify mechanisms of toxicity.

Stem cells are found in all multi cellular organisms. They are characterized by the ability to renew themselves through mitotic cell division and differentiate into a diverse range of specialized cell types. The two broad types of mammalian stem cells are 1) embryonic stem cells that are isolated from the inner cell mass of blastocysts, and 2) adult stem cells that are found in adult tissues. In a developing embryo, stem cells can differentiate into all of the specialized embryonic tissues. In adult organisms, stem cells and progenitor cells act as a repair system for the body, replenishing specialized cells, but also maintaining the normal turnover of regenerative organs, such as blood, skin, or gastric tissues.

Stem cells can now be grown and transformed into specialized cells with characteristics consistent with cells of various tissues such as muscles or nerves through cell culture. Highly plastic adult stem cells from a variety of sources, including umbilical cord blood and bone marrow, are routinely used in medical therapies. Embryonic cell lines and autologous embryonic stem cells generated through therapeutic cloning have also been proposed as promising candidates for future therapies.

The classical definition of a stem cell is typically indicative of two properties: self-renewal, the ability to go through numerous cycles of cell division while maintaining the undifferentiated state, and potency, the capacity to differentiate into specialized cell types. In some embodiments, stem cells are either totipotent or pluripotent, i.e. they are able to give rise to any mature cell type, although multipotent or unipotent progenitor cells may sometimes referred to as stem cells.

Potency specifies the differentiation potential (the potential to differentiate into different cell types) of the stem cell. Totipotent stem cells (also known as omnipotent stem cells) can differentiate into embryonic and extraembryonic cell types. These cells can construct a complete, viable, organism. The cells are produced from the fusion of an egg and sperm cell. Cells produced by the first few divisions of the fertilized egg are also totipotent. Pluripotent stem cells (PSCs) are the descendants of totipotent cells and can differentiate into nearly all cells, i.e., cells derived from any of the three germ layers, including endoderm (interior stomach lining, gastrointestinal tract, the lungs), mesoderm (muscle, bone, blood, urogenital), and ectoderm (epidermal tissues and nervous system). Multipotent stem cells can differentiate into a number of cells, but only those of a closely related family of cells. Oligopotent stem cells can differentiate into only a few cells, such as lymphoid or myeloid stem cells. Unipotent cells can produce only one cell type, their own, but have the property of self-renewal which distinguishes them from non-stem cells (e.g., muscle stem cells).

Embryonic and induced pluripotent stem cells have had an unprecedented impact on the ability to study human diseases and to generate replacement tissues that are therapeutically effective in animal models.

In developmental biology, cellular differentiation is the process by which a less specialized cell becomes a more specialized cell type. Most successful efforts to direct the differentiation of human PSCs into therapeutic cell types have been based on studies of embryonic organ development. Examples include the generation of liver hepatocytes and pancreatic endocrine cells, which have shown functional potential in animal models of liver disease and diabetes. Similarly, differentiation of PSCs into intestine may provide therapeutic benefit for diseases such as necrotizing enterocolitis, inflammatory bowel diseases and short gut syndromes.

As discussed above, a pluripotent stem cell has the potential to differentiate into any of the three germ layers: endoderm (interior stomach lining, gastrointestinal tract, the lungs), mesoderm (muscle, bone, blood, urogenital), and ectoderm (epidermal tissues and nervous system). As such, pluripotent stem cells can give rise to any fetal or adult cell type. However, the fate of the particular pluripotent stem cells is controlled by numerous cellular signaling pathway and numerous factors. Further, the pluripotent stem cells alone cannot develop into a fetal or adult animal because they lack the potential to contribute to extraembryonic tissue, such as the placenta.

To date, gastric tissues have not been generated from human pluripotent stem cells (hPSCs). Successful efforts to differentiate PSCs into lung, liver, pancreas and intestinal cells have depended on a sound molecular understanding of the embryonic development of these organs.[6-10] Unfortunately, a problem in the art is the many gaps in understanding of stomach development subsequent to endoderm formation. Therefore, to direct differentiation of hPSCs into gastric tissue, the signaling pathways that regulate several critical stages of early stomach development including foregut specification and patterning, gastric specification, and lastly, gastric epithelial growth and differentiation were identified by Applicant. In addition, to generate more functional, complex three-dimensional tissue, Applicant aimed to induce several morphogenetic processes that occur during stomach development including morphogenesis of the foregut tube and the formation of gastric epithelial structures including glands and pits.

As described herein, methods and systems are established using a temporal series of growth factor manipulations to mimic embryonic gastric tissue development in culture. In particular, methods and systems are established to direct in vitro the differentiation of PSCs, both human embryonic stem cells (hESC) and induced pluripotent stem cells (iPSC), into gastric tissue. These factors directed human intestinal development in vitro in stages that approximate fetal gut development: activin-induced definitive endoderm (DE) formation; FGF/Wnt/BMP induced posterior foregut pattering, and finally a pro-gastric culture system obtained by modulation of retinoic acid and EFG signaling that promoted gastric tissue growth, morphogenesis and cytodifferentiation into functional gastric cell types and morphology including gastric glands and pits, proliferative zones, surface and antral mucous cells, and endocrine cells expressing gastrin, ghrelin, and somatostatin.

Applicant has identified novel embryonic signaling pathways that allow for efficient step-wise differentiation of human PSCs into gastric cells, gastric tissues, and/or three-dimensional gastric tissue (hGOs) with complex architecture and cellular composition. Applicant has further found that the developing hGOs undergo molecular and morphological stages of differentiation that are nearly identical to the developing antrum of the mouse, and that the resulting gastric organoids may contain an array of mucous, endocrine, and progenitor cells that constitute the normal antral epithelium and a three-dimensional organization comparable to the fetal/postnatal stomach.

The disclosed human gastric cells, gastric tissue and/or gastric organoids (hGOs) may be used as an in vitro system to identify new mechanisms of human stomach development, physiology, and may be used as a model of the pathophysiological response of the gastric epithelium to *H. pylori*. The disclosed gastric cells, gastric tissue and/or gastric hGOs and methods present new opportunities for drug discovery and modeling of early stages of gastric cancer. Moreover, disclosed herein is the first three-dimensional production of a human embryonic foregut, which is a promising starting point for the generation of other foregut organ tissues including lungs and pancreas.

In one aspect, a method of inducing formation of a gastric cell, gastric tissue, and or gastric hGO from a precursor cell is disclosed. The method may comprise the step of a) activating one or more signaling pathways within a precursor cell, wherein the one or more signaling pathways are selected from the WNT signaling pathway, the WNT/FGF signaling pathway, and the FGF signaling pathway to obtain a gastric cell, gastric tissue and/or gastric hGO descended from the precursor cell. The method may further comprise a step b) of inhibiting one or more signaling pathways within a precursor cell. The one or more signaling pathways that are inhibited may comprise a BMP signaling pathway.

The method may further comprise the step of contacting the precursor cell with retinoic acid. The contacting of a precursor cell with retinoic acid may occur after the activating and inhibiting steps above.

The method may further comprise the step of contacting a gastric organoid to EGF at a concentration and/or length of time sufficient to increase the diameter of the gastric organoid to greater than about 1 mm in diameter, or greater than about 2 mm in diameter, or greater than about 3 mm in diameter, or greater than about 4 mm in diameter.

In one aspect, the one or more signaling pathways may be selected from a Wnt signaling pathway, Wnt/beta-catenin signaling, Wnt/APC signaling, and Wnt/PCP pathway signaling.

In one aspect, the step of activating a Wnt signaling pathway may comprise contacting a precursor cell with one or more molecules selected from the group consisting of Wnt1, Wnt2, Wnt2b, Wnt3, Wnt3a, Wnt4, Wnt5a, Wnt5b, Wnt6, Wnt7a, Wnt7b, Wnt8a, Wnt8b, Wnt9a, Wnt9b, Wnt10a, Wnt10b, Wnt11, and Wnt16.

In one aspect, the step of activating the FGF signaling pathway may comprise contacting a precursor cell with one or more molecules selected from the group consisting of FGF1, FGF2, FGF3, FGF4, FGF5, FGF6, FGF7 FGF8, FGF9, FGF10, FGF11, FGF12, FGF13, FGF14, FGF16, FGF17, FGF18, FGF19, FGF20, FGF21, FGF22, and FGF23.

In one aspect, the step of inhibiting a BMP signaling pathway may comprise contacting the precursor cell with a BMP inhibitor. In one aspect, the BMP inhibitor may be selected from Dorsomorphin, LDN189, DMH-1, Noggin and combinations thereof. In one aspect, the BMP inhibitor may be Noggin.

In one aspect, the activating step may comprise contacting a precursor cell with Wnt3a, FGF4, and a BMP inhibitor over a specified period which is referred to as an incubation period. The contacting steps may occur simultaneously, or, in other aspects, the contacting steps may occur subsequently.

In one aspect, a precursor cell, which may comprise definitive endoderm, may be contacted by a signaling agent that may comprise 1) Wnt3a or a GSK-inhibitor (for example, CHIRON) in combination with 2) FGF4, during a first incubation period. The first incubation period may further comprise a BMP inhibitor. Following the first incubation period, the precursor cells may be subjected to a second incubation period wherein the precursor cells are contacted with retinoic acid (RA). In one aspect, the first incubation period and the second incubation period overlap. In some embodiments, the first incubation period and the second incubation period do not overlap.

In one aspect, the first and/or second incubation period, and/or the totality of the first and second incubation period may be between 24 and 120 hours, or from about 36 to about 108 hours, or from about 48 to about 96 hours, or from about 60 to about 84 hours. In one aspect, the first incubation period may be at least about 24 hours.

In one aspect, the second incubation period (wherein the precursor cells may be contacted with RA) begins about 72 hours after the first incubation period. In a further aspect, the second incubation period begins after cultures have formed foregut spheroids from the precursor cells. The foregut spheroids may then be transferred to a 3-dimensional matrix under growth conditions suitable for formation of a gastric organoid, for example, by application of the foregut spheroids to Matrigel™ (Corning, BD Bioscience). Following transfer to Matrigel, the foregut spheroids are contacted with RA during a third incubation period in which continued 3D growth may occur. The spheroids may then be contacted with EGF during a fourth incubation period, which may overlap with the third incubation period. The third incubation period may be about 24 hours.

In one aspect, the precursor cell may be contacted with Wnt3a at a concentration between 50-1500 ng/ml, or from about 100 to about 1200 ng/ml, or from about 200 to about 1000 ng/ml, or from about 300 to about 900 ng/ml, or from about 400 to about 800 ng/ml, or from about 500 to about 700 ng/ml.

In one aspect, the precursor cell may be selected from an embryonic stem cell, an embryonic germ cell, an induced pluripotent stem cell, a mesoderm cell, a definitive endoderm cell, a posterior endoderm cell, and a hindgut cell.

In one aspect, the precursor cell may be a definitive endoderm cell derived from a pluripotent stem cell.

In one aspect, the precursor cell may be a pluripotent stem cell such as an embryonic stem cell, an embryonic stem cell, or an induced pluripotent stem cell.

In one aspect, the definitive endoderm cell may be derived by contacting the pluripotent stem cell with one or more molecules selected from of Activin, the BMP subgroups of the TGF-beta superfamily of growth factors; Nodal, Activin A, Activin B, BMP4, Wnt3a, and a combination thereof.

In one aspect, a gastric tissue may be produced in vitro from one or more precursor cells.

In one aspect, the one or more precursor cells may be selected from an embryonic stem cell, a mesoderm cell, a definitive endoderm cell, a posterior endoderm cell, an anterior endoderm cell, a foregut cell, and a hindgut cell.

In one aspect, the pluripotent stem cell may be a mammalian pluripotent stem cell, including but not limited to human pluripotent stem cell, or a mouse pluripotent stem cell.

In one aspect, the human pluripotent stem cell may be selected from a human embryonic stem cell, a human embryonic germ cell, and an induced human pluripotent stem cell.

In one aspect, a kit comprising a gastric cell, tissue, or organoid produced in vitro from one or more precursor cells is provided.

In one aspect, a method for identifying the absorption effect of gastric cells or tissues is provided. The method may comprise the steps of contacting a gastric cell, tissue, or organoid derived from a precursor cell with a compound; and detecting a level of absorption of a compound by said gastric cells or tissues.

In one aspect, a method for identifying the toxicity of a compound on a gastric cell or tissue is provided. The method may comprise the steps of contacting a gastric cell, tissue, or organoid derived from a precursor cell with a compound; and detecting a level of absorption of a compound by said gastric cells or tissues.

In one aspect, compositions comprising three-dimensional human gastric organoids (hGOs) generated de novo, and methods of making same through directed differentiation of human pluripotent stem cells (hPSCs) are disclosed. Such hGOs may be used these to model stomach development as well as the early events that occur during *H. pylori* infection.

In one aspect, methods for generating an hGO in vitro through the directed differentiation of human pluripotent stem cells (hPSCs) are disclosed. This human gastric tissue may be used to model human stomach development and disease. Methods for inducing definitive endoderm (DE) to form 3-dimensional gut tube structures are also disclosed. In one aspect, this may be carried out by activating FGF and WNT signaling, while a foregut fate may be promoted by simultaneously inhibiting BMP signaling. Foregut spheroids may then be directed into a posterior foregut and gastric fate by manipulation of retinoic acid and EGF signaling, resulting in hGOs.

Developing hGOs may undergo molecular and morphogenetic changes nearly identical to the developing mouse antrum, forming gastric glands and pits, proliferative zones, surface and antral mucous cells, and endocrine cells expressing Gastrin, Ghrelin and Somatostatin. Using hGOs to model human stomach development it has been determined that EGF signaling represses endocrine cell development upstream of the transcription factor NEUROGENIN 3. Applicant has further found that hGOs faithfully recapitulate early stages of gastric disease initiated by *H. pylori*, including rapid activation of c-Met signaling and epithelial proliferation. Together, these studies describe a novel and robust in vitro system for elucidating the mechanisms underlying human stomach development and disease.

Pluripotent Stem Cells Derived from Embryonic Cells

In one aspect, the methods may include the step of obtaining stem cells that are pluripotent or can be induced to become pluripotent. In some embodiments, pluripotent stem cells are derived from embryonic stem cells, which are in turn derived from totipotent cells of the early mammalian embryo and are capable of unlimited, undifferentiated proliferation in vitro. Embryonic stem cells are pluripotent stem cells derived from the inner cell mass of the blastocyst, an early-stage embryo. Methods for deriving embryonic stem cells from blastocytes are well known in the art. For example, while certain cell types are exemplified herein, it would be understood by one of skill in the art that the methods and systems described herein are applicable to any stem cells.

Additional stem cells that can be used in embodiments in accordance with the present invention include but are not limited to those provided by or described in the database hosted by the National Stem Cell Bank (NSCB), Human Embryonic Stem Cell Research Center at the University of California, San Francisco (UCSF); WISC cell Bank at the Wi Cell Research Institute; the University of Wisconsin Stem Cell and Regenerative Medicine Center (UW-SCRMC); Novocell, Inc. (San Diego, Calif.); Cellartis AB (Goteborg, Sweden); ES Cell International Pte Ltd (Singapore); Technion at the Israel Institute of Technology (Haifa, Israel); and the Stem Cell Database hosted by Princeton University and the University of Pennsylvania. Exemplary embryonic stem cells that can be used in embodiments in accordance with the present invention include but are not limited to SA01 (SA001); SA02 (SA002); ES01 (HES-1); ES02 (HES-2); ES03 (HES-3); ES04 (HES-4); ES05 (HES-5); ES06 (HES-6); BG01 (BGN-01); BG02 (BGN-02); BG03 (BGN-03); TE03 (13); TE04 (14); TE06 (16); UC01 (HSF1); UC06 (HSF6); WA01 (H1); WA07 (H7); WA09 (H9); WA13 (H13); WA14 (H14).

In some embodiments, the stem cells may be further modified to incorporate additional properties. Exemplary modified cell lines include, but are not limited to, H1 OCT4-EGFP; H9 Cre-LoxP; H9 hNanog-pGZ; H9 hOct4-pGZ; H9 in GFPhES; and H9 Syn-GFP.

More details on embryonic stem cells can be found in, for example, Thomson et al., 1998, "Embryonic Stem Cell Lines Derived from Human Blastocysts," Science 282 (5391): 1145-1147; Andrews et al., 2005, "Embryonic stem (ES) cells and embryonal carcinoma (EC) cells: opposite sides of the same coin," Biochem Soc Trans 33:1526-1530; Martin 1980, "Teratocarcinomas and mammalian embryogenesis,". Science 209 (4458): 768-776; Evans and Kaufman, 1981, "Establishment in culture of pluripotent cells from mouse embryos," Nature 292(5819): 154-156; Klimanskaya et al., 2005, "Human embryonic stem cells derived without feeder cells," Lancet 365 (9471): 1636-1641; each of which is hereby incorporated herein in its entirety.

Alternative, pluripotent stem cells can be derived from embryonic germ cells (EGCs), which are the cells that give rise to the gametes of organisms that reproduce sexually. EGCs are derived from primordial germ cells found in the gonadal ridge of a late embryo, have many of the properties of embryonic stem cells. The primordial germ cells in an embryo develop into stem cells that in an adult generate the reproductive gametes (sperm or eggs). In mice and humans it is possible to grow embryonic germ cells in tissue culture under appropriate conditions. Both EGCs and ESCs are pluripotent. For purpose of the present invention, the term "ESCs" is used broadly sometimes to encompass EGCs.

Induced Pluripotent Stem Cells (iPSCs)

In some embodiments, iPSCs are derived by transfection of certain stem cell-associated genes into non-pluripotent cells, such as adult fibroblasts. Transfection is typically achieved through viral vectors, such as retroviruses. Transfected genes include the master transcriptional regulators Oct-3/4 (Pouf51) and Sox2, although it is suggested that other genes enhance the efficiency of induction. After 3-4 weeks, small numbers of transfected cells begin to become morphologically and biochemically similar to pluripotent stem cells, and are typically isolated through morphological selection, doubling time, or through a reporter gene and antibiotic selection. As used herein, iPSCs may include, but are not limited to, first generation iPSCs, second generation iPSCs in mice, and human induced pluripotent stem cells. In some embodiments, a retroviral system may used to transform human fibroblasts into pluripotent stem cells using four pivotal genes: Oct3/4, Sox2, Klf4, and c-Myc. In alternative embodiments, a lentiviral system is used to transform somatic cells with OCT4, SOX2, NANOG, and LIN28. Genes whose expression may be induced in iPSCs include but are not limited to Oct-3/4 (e.g., Pou5fl); certain members of the Sox gene family (e.g., Sox1, Sox2, Sox3, and Sox15); certain members of the Klf family (e.g., Klf1, Klf2, Klf4, and Klf5), certain members of the Myc family (e.g., C-myc, L-myc, and N-myc), Nanog, and LIN28.

In some embodiments, non-viral based technologies may be employed to generate iPSCs. In some embodiments, an adenovirus can be used to transport the requisite four genes into the DNA of skin and liver cells of mice, resulting in cells identical to embryonic stem cells. Since the adenovirus does not combine any of its own genes with the targeted host, the danger of creating tumors is eliminated. In some embodiments, reprogramming can be accomplished via plasmid without any virus transfection system at all, although at very low efficiencies. In other embodiments, direct delivery of proteins is used to generate iPSCs, thus eliminating the need for viruses or genetic modification. In some embodiment, generation of mouse iPSCs is possible using a similar methodology: a repeated treatment of the cells with certain proteins channeled into the cells via poly-arginine anchors was sufficient to induce pluripotency. In some embodiments, the expression of pluripotency induction genes can also be increased by treating somatic cells with FGF2 under low oxygen conditions.

More details on embryonic stem cells can be found in, for example, Kaji et al., 2009, "Virus free induction of pluripotency and subsequent excision of reprogramming factors," Nature 458:771-775; Woltjen et al., 2009, "piggyBac transposition reprograms fibroblasts to induced pluripotent stem cells," Nature 458:766-770; Okita et al., 2008, "Generation of Mouse Induced Pluripotent Stem Cells Without Viral Vectors," Science 322(5903):949-953; Stadtfeld et al., 2008, "Induced Pluripotent Stem Cells Generated without Viral Integration," Science 322(5903):945-949; and Zhou et al., 2009, "Generation of Induced Pluripotent Stem Cells Using Recombinant Proteins," Cell Stem Cell 4(5):381-384; each of which is hereby incorporated herein in its entirety.

In some embodiments, exemplary iPS cell lines include but are not limited to iPS-DF19-9; iPS-DF19-9; iPS-DF4-3; iPS-DF6-9; iPS(Foreskin); iPS(IMR90); and iPS(IMR90).

It has been shown that iPSCs were capable of differentiation in a fashion similar to ESCs into fully differentiated tissues. For example, iPSCs were differentiated into neurons, expressing βIII-tubulin, tyrosine hydroxylase, AADC, DAT, ChAT, LMX1B, and MAP2. The presence of catecholamine-associated enzymes may indicate that iPSCs, like hESCs, may be differentiable into dopaminergic neurons. Stem cell-associated genes were shown to be down-regulated after differentiation. It has also been shown that iPSCs may be differentiated into cardiomyocytes that spontaneously began beating. Cardiomyocytes expressed TnTc, MEF2C, MYL2A, MYHCβ, and NKX2.5. Stem cell-associated genes were down-regulated after differentiation.

Gastric Organ and Development

Prior to Applicant's invention, no systems were available for converting precursor cells such as embryonic stem cells and/or iPSCs into gastric tissues.

In some embodiments, PSCs, such as ESCs and iPSCs, undergo directed differentiation in a step-wise manner first into definitive endoderm (DE) then into three dimensional gut tube structures (foregut spheroids) then into three dimensional gastric organoid (hGO) via formation of a posterior foregut/gastric tissue.

In some embodiments, PSCs, such as ESCs and iPSCs, undergo directed differentiation in a non step-wise manner where molecules (e.g., growth factors, ligands) for promoting DE formation and those for subsequent tissue formation are added at the same time.

Definitive Endoderm

The epithelium of the stomach is derived from a simple sheet of cells called the definitive endoderm (DE). The anterior DE forms the foregut and its associated organs including the lungs, esophagus, stomach, liver and pancreas and the posterior DE forms the midgut and hindgut, which forms the small and large intestines and parts of the genitourinary system. The DE gives rise to the epithelia of the gastrointestinal and respiratory tracts in vivo. Studies using mouse, chick and frog embryos suggest that establishing the anterior-posterior pattern in DE at the gastrula stage is a prerequisite for subsequent foregut and hindgut development. In some embodiments, PSCs, such as ESCs and iPSCs, undergo directed differentiation in a step-wise manner first into definitive endoderm (DE) then into anterior/foregut epithelium (e.g., foregut spheroids), and then into gastric tissue. The BMP, Wnt and FGF signaling pathways are believed to be critical for this process. Activation of WNT and FGF act to promote gut tube morphogenesis and inhibition of BMP signaling promotes a foregut fate. The simple cuboidal epithelium of the foregut first develops into a pseudostratified columnar epithelium, then into glands and pits containing gastric epithelium and a proliferative zone at the base of the villi, which corresponds with the presumptive progenitor domain.

A robust and efficient process is established to direct the differentiation of DE into gastric tissue in vitro. In some embodiments, directed differentiation is achieved by selectively activating certain signaling pathways in the iPSCs and/or DE cells. In some embodiments, the signaling pathways are those active in gastric tissue development, including but not limited to the Wnt signaling pathway, Wnt/APC signaling pathway, FGF signaling pathway, TGF-beta signaling pathway, BMP signaling pathway; EGF signaling pathway, and Retinoic Acid signaling pathway.

More details on the functions of signaling pathways relating to DE development and/or intestinal development in general can be found in, for example, Zorn and Wells, 2009, "Vertebrate endoderm development and organ formation," Annu Rev Cell Dev Biol 25:221-251; Dessimoz et al., 2006, "FGF signaling is necessary for establishing gut tube domains along the anterior-posterior axis in vivo," Mech Dev 123:42-55; McLin et al., 2007, "Repression of Wnt/{beta}-catenin signaling in the anterior endoderm is essential for liver and pancreas development. Development," 134:2207-2217; Wells and Melton, 2000, Development 127: 1563-1572; de Santa Barbara et al., 2003, "Development and differentiation of the intestinal epithelium," Cell Mol Life Sci 60(7): 1322-1332; Sancho et al., 2004, "Signaling Pathways in Intestinal Development and Cancer," Annual Review of Cell and Developmental Biology 20:695-723; Logan and Nusse, 2004, "The Wnt Signaling Pathway in Development and Disease," Annual Review of Cell and Developmental Biology 20:781-810; Taipalel and Beachyl, 2001, "The Hedgehog and Wnt signalling pathways in cancer," Nature 411:349-354; Gregorieff and Clevers, 2005, "Wnt signaling in the intestinal epithelium: from endoderm to cancer," Genes & Dev. 19: 877-890; each of which is hereby incorporated herein in its entirety.

Any methods for producing definitive endoderm from pluripotent cells (e.g., iPSCs or ESCs) are applicable to the methods described herein. In some embodiments, pluripotent cells are derived from a morula. In some embodiments, pluripotent stem cells are stem cells. Stem cells used in these methods can include, but are not limited to, embryonic stem cells. Embryonic stem cells can be derived from the embryonic inner cell mass or from the embryonic gonadal ridges. Embryonic stem cells or germ cells can originate from a variety of animal species including, but not limited to, various mammalian species including humans. In some embodiments, human embryonic stem cells are used to produce definitive endoderm. In some embodiments, human embryonic germ cells are used to produce definitive endoderm. In some embodiments, iPSCs are used to produce definitive endoderm.

In some embodiments, one or more growth factors are used in the differentiation process from pluripotent stem cells to DE cells. The one or more growth factors used in the differentiation process can include growth factors from the TGF-beta superfamily. In such embodiments, the one or more growth factors comprise the Nodal/Activin and/or the BMP subgroups of the TGF-beta superfamily of growth factors. In some embodiments, the one or more growth factors are selected from the group consisting of Nodal, Activin A, Activin B, BMP4, Wnt3a or combinations of any of these growth factors.

In some embodiments, the embryonic stem cells or induced pluripotent cells and iPSCs are treated with the one or more growth factors for 6 or more hours; 12 or more hours; 18 or more hours; 24 or more hours; 36 or more hours; 48 or more hours; 60 or more hours; 72 or more hours; 84 or more hours; 96 or more hours; 120 or more hours; 150 or more hours; 180 or more hours; or 240 or more hours.

In some embodiments, the embryonic stem cells or germ cells and iPSCs are treated with the one or more growth factors at a concentration of 10 ng/ml or higher; 20 ng/ml or higher; 50 ng/ml or higher; 75 ng/ml or higher; 100 ng/ml or higher; 120 ng/ml or higher; 150 ng/ml or higher; 200 ng/ml or higher; 500 ng/ml or higher; 1,000 ng/ml or higher; 1,200 ng/ml or higher; 1,500 ng/ml or higher; 2,000 ng/ml or higher; 5,000 ng/ml or higher; 7,000 ng/ml or higher; 10,000 ng/ml or higher; or 15,000 ng/ml or higher. In some embodiments, concentration of the growth factor is maintained at a constant level throughout the treatment. In other embodiments, concentration of the growth factor is varied during the course of the treatment. In some embodiments, the growth factor is suspended in media that include fetal bovine serine (FBS) with varying HyClone concentrations. One of skill in the art would understand that the regimen described herein is applicable to any known growth factors, alone or in combination. When two or more growth factors are used, the concentration of each growth factor may be varied independently.

In some embodiments, populations of cells enriched in definitive endoderm cells are used. In some embodiments, the definitive endoderm cells are isolated or substantially purified. In some embodiments, the isolated or substantially purified definitive endoderm cells express the SOX17, FOXA2, and/or the CXRC4 marker to a greater extent than the OCT4, AFP, TM, SPARC and/or SOX7 markers.

Methods for enriching a cell population with definitive endoderm are also contemplated. In some embodiments, definitive endoderm cells can be isolated or substantially purified from a mixed cell population by contacting the cells with a reagent that binds to a molecule that is present on the surface of definitive endoderm cells but which is not present on the surface of other cells in the mixed cell population, and then isolating the cells bound to the reagent. In certain embodiments, the cellular constituent that is present on the surface of definitive endoderm cells is CXCR4.

Still other embodiments of the present invention relate to CXCR4 antibodies, SDF-1 ligands or other ligands for CXCR4 can be used to obtain definitive endoderm cells in an enriched, isolated or substantially purified form. For example, a CXCR4 antibody, an SDF-1 ligand or another ligand for CXCR4 can be used as a reagent in a method, such as affinity-based separation or magnetic-based separation, to enrich, isolate or substantially purify preparations of definitive endoderm cells that bind to the reagent.

In some embodiments, definitive endoderm cells and hESCs are treated with one or more growth factors. Such growth factors can include growth factors from the TGF-beta superfamily. In such embodiments, the one or more growth factors comprise the Nodal/Activin and/or the BMP subgroups of the TGF-beta superfamily of growth factors. In some embodiments, the one or more growth factors are selected from the group consisting of Nodal, Activin A, Activin B, BMP4, Wnt3a or combinations of any of these growth factors.

Additional methods for obtaining or creating DE cells that can be used in the present invention include but are not limited to those described in U.S. Pat. No. 7,510,876 to D'Amour et al.; U.S. Pat. No. 7,326,572 to Fisk et al.; Kubol et al., 2004, "Development of definitive endoderm from embryonic stem cells in culture," Development 131:1651-1662; D'Amour et al., 2005, "Efficient differentiation of human embryonic stem cells to definitive endoderm," Nature Biotechnology 23:1534-1541; and Ang et al., 1993, "The formation and maintenance of the definitive endoderm lineage in the mouse: involvement of HNF3/forkhead proteins," Development 119:1301-1315; each of which is hereby incorporated by reference herein in its entirety.

Directed Differentiation of Posteriorized DE

In some embodiments, activin-induced definitive endoderm (DE) can further undergo FGF/Wnt/Noggin induced anterior endoderm patterning, foregut specification and morphogenesis, and finally a pro-gastric culture system to promote gastric tissue growth, morphogenesis and cytodifferentiation into functional gastric cell types including surface mucous cells, mucous gland cells, endocrine, and progenitor cells. In some embodiments, human PSCs are efficiently directed to differentiate in vitro into gastric epithelium that includes mucous, endocrine, and progenitor cell types. It will be understood that molecules such as growth factors can be added to any stage of the development to promote a particular type of gastric tissue formation.

In some embodiments, anteriorized endoderm cells of the DE are further developed into one or more specialized cell types.

In some embodiments, soluble FGF and Wnt ligands and BMP antagonists are used to mimic early foregut specification in culture to convert, through directed differentiation, DE developed from iPSCs or ESCs into foregut epithelium that efficiently gives rise to all the major antrum gastric cell types. In human, directed differentiation of DE is achieved through selective activating certain signaling pathways that are important to gastric development.

Human stomach/gastric development in vitro occurs in stages that approximate fetal gut development; endoderm formation, anterior endoderm patterning, foregut morphogenesis, fetal gastric, antral and fundic development, epithelial morphogenesis, formation of a presumptive progenitor domain, and differentiation into functional cell types of the stomach.

It will be understood by one of skill in the art that altering the expression of any Wnt signaling protein in combination with any FGF ligand can give rise to directed differentiation in accordance of the present invention. In some embodiments, the alteration is over-expression of Wnt3, in particular Wnt3a. In some embodiments, the alternation is over-expression of Wnt1 or other Wnt ligands.

It will be understood by one of skill in the art that altering the signaling activity of the Wnt signaling pathway in combination with altering the signaling activity of the FGF signaling pathway can give rise to directed differentiation in accordance of the present invention. In some embodiments, the alteration is through the use of small molecule modulators that activate the aforementioned pathways. For example, Small molecule modulators of the Wnt pathway included, but is not limited to Lithium Chloride; 2-amino-4,6-disubstituted pyrimidine (hetero) arylpyrimidines; IQ1; QS11; NSC668036; DCA beta-catenin; 2-amino-4-[3,4-(methylenedioxy)-benzyl-amino]-6-(3-methoxyphenyl) pyrimidine.

In alternative embodiments, cellular constituents associated with the Wnt and/or FGF signaling pathways, for example, natural inhibitors or antagonist of the pathways can be inhibited to result in activation of the Wnt and/or FGF signaling pathways.

In some embodiment, the cellular constituents are inhibited by other cellular constituents or extrinsic molecules. Exemplary natural inhibitors of Wnt signaling include but are not limited to Dkk1, SFRP proteins and FrzB. In some embodiments, the extrinsic molecules may include, but are not limited to, small molecules such as WAY-316606; SB-216763; or BIO (6-bromoindirubin-3'-oxime).

More details are found, for example, in Liu et al., "A small-molecule agonist of the Wnt signaling pathway," Angew Chem Int Ed Engl. 44(13):1987-1990 (2005); Miyabayashi et al., "Wnt/beta-catenin/CBP signaling maintains long-term murine embryonic stem cell pluripotency," Proc Natl Acad Sci USA. 104(13):5668-5673 (2007); Zhang et al., "Small-molecule synergist of the Wnt/beta-catenin signaling pathway," Proc Natl Acad Sci USA. 104(18):7444-7448 (2007); Neiiendam et al., "An NCAM-derived FGF-receptor agonist, the FGL-peptide, induces neurite outgrowth and neuronal survival in primary rat neurons," J. Neurochem. 91(4):920-935 (2004); Shan et al., "Identification of a specific inhibitor of the dishevelled PDZ domain," Biochemistry 44(47): 15495-15503 (2005); Coghlan et al., "Selective small molecule inhibitors of glycogen synthase kinase-3 modulate glycogen metabolism and gene transcription," Chem. Biol. 7(10):793-803 (2000); Coghlan et al., "Selective small molecule inhibitors of glycogen synthase kinase-3 modulate glycogen metabolism and gene transcription," Chemistry & Biology 7(10):793-803; and Pai et al., "Deoxycholic acid activates beta-catenin signaling pathway and increases colon cell cancer growth and invasiveness," Mol Biol Cell. 15(5):2156-2163 (2004); each of which is hereby incorporated by reference in its entirety.

In some embodiments, siRNA and/or shRNA targeting cellular constituents associated with the Wnt and/or FGF signaling pathways are used to activate these pathways. It would be understood by one of skill in the art that the target cellular constituents may include, but are not limited to, SFRP proteins; GSK3, Dkk1, and FrzB.

More details about RNAi based technologies can be found, for example, in Couzin, 2002, Science 298:2296-2297; McManus et al., 2002, Nat. Rev. Genet. 3, 737-747; Hannon, G. J., 2002, Nature 418, 244-251; Paddison et al., 2002, Cancer Cell 2, 17-23; Elbashir et al., 2001. EMBO J. 20:6877-6888; Tuschl et al., 1999, Genes Dev. 13:3191-3197; Hutvagner et al., Sciencexpress 297:2056-2060; each of which is hereby incorporated by reference in its entirety.

Fibroblast growth factors (FGFs) are a family of growth factors involved in angiogenesis, wound healing, and embryonic development. The FGFs are heparin-binding proteins and interactions with cell-surface associated heparan sulfate proteoglycans have been shown to be essential for FGF signal transduction. FGFs are key players in the processes of proliferation and differentiation of wide variety of cells and tissues. In humans, 22 members of the FGF family have been identified, all of which are structurally related signaling molecules. Members FGF1 through FGF10 all bind fibroblast growth factor receptors (FGFRs). FGF1 is also known as acidic, and FGF2 is also known as basic fibroblast growth factor. Members FGF11, FGF12, FGF13, and FGF14, also known as FGF homologous factors 1-4 (FHF1-FHF4), have been shown to have distinct functional differences compared to the FGFs. Although these factors possess remarkably similar sequence homology, they do not bind FGFRs and are involved in intracellular processes unrelated to the FGFs. This group is also known as "iFGF." Members FGF16 through FGF23 are newer and not as well characterized. FGF15 is the mouse ortholog of human FGF19 (hence there is no human FGF15). Human FGF20 was identified based on its homology to *Xenopus* FGF-20 (XFGF-20). In contrast to the local activity of the other FGFs, FGF15/FGF19, FGF21 and FGF23 have more systemic effects.

In some embodiments, it will be understood by one of skill in the art that any of the FGFs can be used in conjunction with a protein from the Wnt signaling pathway. In some embodiments, soluble FGFs may include, but are not limited to, FGF4, FGF2, and FGF3.

In some embodiment, the cellular constituents of the FGF signaling pathway are inhibited by other cellular constituents or extrinsic molecules. Exemplary natural inhibitors of FGF signaling may include, but are not limited to, the Sprouty family of proteins and the Spred family of proteins. As discussed above, proteins, small molecules, nucleic acids can be used to activating the FGF signaling pathway.

It will be understood by one of skill in the art that the methods and compositions described herein in connection with the Wnt and FGF signaling pathways are provided by way of examples. Similar methods and compositions are applicable to other signaling pathways disclosed herein.

In some embodiments, DE culture may be treated with the one or more molecules of a signaling pathway described herein for 6 or more hours; 12 or more hours; 18 or more hours; 24 or more hours; 36 or more hours; 48 or more hours; 60 or more hours; 72 or more hours; 84 or more hours; 96 or more hours; 120 or more hours; 150 or more hours; 180 or more hours; 200 or more hours, 240 or more hours; 270 or more hours; 300 or more hours; 350 or more hours; 400 or more hours; 500 or more hours; 600 or more hours; 700 or more hours; 800 or more hours; 900 or more hours; 1,000 or more hours; 1,200 or more hours; or 1,500 or more hours.

In some embodiments, DE culture is treated with the one or more molecules of a signaling pathway described herein at a concentration of 10 ng/ml or higher; 20 ng/ml or higher; 50 ng/ml or higher; 75 ng/ml or higher; 100 ng/ml or higher; 120 ng/ml or higher; 150 ng/ml or higher; 200 ng/ml or higher; 500 ng/ml or higher; 1,000 ng/ml or higher; 1,200 ng/ml or higher; 1,500 ng/ml or higher; 2,000 ng/ml or higher; 5,000 ng/ml or higher; 7,000 ng/ml or higher; 10,000 ng/ml or higher; or 15,000 ng/ml or higher. In some embodiments, concentration of signaling molecule is maintained at a constant throughout the treatment. In other embodiments, concentration of the molecules of a signaling pathway is varied during the course of the treatment. In some embodiments, a signaling molecule in accordance with the present invention is suspended in media comprising DMEM and fetal bovine serine (FBS). The FBS can be at a concentration of 2% and more; 5% and more; 10% or more; 15% or more; 20% or more; 30% or more; or 50% or more. One of skill in the art would understand that the regiment described herein is applicable to any known molecules of the signaling pathways described herein, alone or in combination, including but not limited to any molecules in the Wnt and FGF signaling pathways.

In embodiments where two or more signaling molecules are used to treat the DE culture, the signaling molecules can be added simultaneously or separately. When two or more molecules are used, the concentration of each may be varied independently.

Differentiation of PSCs into DE culture and subsequently into various intermediate mature gastric cell types can be determined by the presence of stage-specific cell markers. In some embodiments, expression of representative cellular constituents is used to determine DE formation. The representative cellular constituents may include, but are not limited to, CMKOR1, CXCR4, GPR37, RTN4RL1, SLC5A9, SLC40A1, TRPA1, AGPAT3, APOA2, C20orf56, C21orf129, CALCR, CCL2, CER1, CMKOR1, CRIP1, CXCR4, CXorf1, DIO3, DIO30S, EB-1, EHHADH, ELOVL2, EPSTI1, FGF17, FLJ10970, FLJ21195, FLJ22471, FLJ23514, FOXA2, FOXQ1, GATA4, GPR37, GSC, LOC283537, MYL7, NPPB, NTN4, PRSS2, RTN4RL1, SEMA3E, SIAT8D, SLC5A9, SLC40A1, SOX17, SPOCK3, TMOD1, TRPA1, TTN, AW166727, AI821586, BF941609, AI916532, BC034407, N63706 and AW772192.

Additional cellular constituents suitable for detecting DE formation can be found in, for example, in U.S. patent application Ser. No. 11/165,305, filed Jun. 23, 2005; U.S. patent application Ser. No. 11/317,387, filed Dec. 22, 2005; U.S. patent Ser. No. 11/021,618, filed Dec. 23, 2004; U.S. patent application Ser. Nos. 11/021,618, 11/115,868 filed on Apr. 26, 2005; U.S. patent application Ser. No. 11/317,387, filed on Dec. 22, 2005; U.S. patent application Ser. No. 11/474,211, filed on Jun. 23, 2006; U.S. patent application Ser. No. 11/165,305, filed on Jun. 23, 2005; U.S. patent application Ser. No. 11/587,735 filed on Aug. 29, 2008; U.S. patent application Ser. No. 12/039,701, filed on Feb. 28, 2008; U.S. patent application Ser. No. 12/414,482, filed on Mar. 30, 2009; U.S. patent application Ser. No. 12/476,570, filed on Jun. 2, 2009; U.S. patent application Ser. No. 12/093,590 filed on Jul. 21, 2008; U.S. patent application Ser. No. 12/582,600 filed on Oct. 20, 2009; each of which is hereby incorporated by reference herein in its entirety.

In some embodiments, expression of SOX2 is used to reveal tendency of foregut formation after DE have been incubated with FGF4 and Wnt3a plus Noggin for a period of time, for example, for 12 hours or longer; 18 hours or longer; 24 hours or longer; 36 hours or longer; 48 hours or longer; 60 hours or longer; or 90 hours or longer. In some embodiments, longer periods of incubation are needed to achieve a stable anterior endoderm phenotype as measured by prolonged expressed of CDX2. In such embodiments, the periods of incubation can be for 60 hours or longer; 72 hours or longer; 84 hours or longer; 96 hours or longer; 108 hours or longer; 120 hours or longer; 140 hours or longer; 160 hours or longer; 180 hours or longer; 200 hours or longer; 240 hours or longer; or 300 hours or longer.

Alternatively, in some embodiments, the absence of cellular constituents, such as hindgut markers such as CDX2 can be used to reveal directed foregut formation. In some embodiments, gastric transcription factors PDX1, KLF5, and SOX9 can be used to represent gastric development. In some embodiments, GATA4 and/or GATA6 protein expression can be used to represent gastric development. In these embodiments, the periods of incubation can be for 12 hours or longer; 18 hours or longer; 24 hours or longer; 36 hours or longer; 48 hours or longer; 60 hours or longer; or 90 hours or longer. Alternatively, the periods of incubation can be for 60 hours or longer; 72 hours or longer; 84 hours or longer; 96 hours or longer; 108 hours or longer; 120 hours or longer; 140 hours or longer; 160 hours or longer; 180 hours or longer; 200 hours or longer; 240 hours or longer; or 300 hours or longer.

In some embodiments, abundance data of cellular constituents, for example, protein and/or gene expression levels, are determined by immunohistochemistry using primary and/or secondary antibodies targeting molecules in the relevant signaling pathways. In other embodiments, abundance data of cellular constituents, for example, protein and/or gene expression levels, are determined by microarray analyses.

Still alternatively, morphological changes can be used to represent the progress of directed differentiation. In some embodiments, foregut spheroids may be further subject to 3-dimensional culture conditions for further maturation. Additionally, gastric organoids can be observed in 6 days or longer; 7 days or longer; 9 days or longer; 10 days or longer; 12 days or longer; 15 days or longer; 20 days or longer; 25 days or longer; 28 days or longer; 32 days or longer; 36 days or longer; 40 days or longer; 45 days or longer; 50 days or longer; or 60 days or longer.

Directed Differentiation of Pluripotent Stem Cells

In some embodiments, pluripotent stem cells are converted into gastric cell types via a "one step" process. For example, one or more molecules that can differentiate pluripotent stem cells into DE culture (e.g., ActivinA) are combined with additional molecules that can promote directed differentiation of DE culture (e.g., Wnt3a/FGF4 activators and BMP inhibitors) to directly treat pluripotent stem cells.

Utilities and Kits Embodiments

In some embodiments, gastric tissue or related cell types described herein can be used to screen drugs for gastric uptake and/or mechanisms of transport and/or treatment of *H. Pylori*. For example, this can be done in a high throughput manner to screen for the most readily absorbed or effective drugs, and can augment Phase 1 clinical trials that are done to study drug gastric uptake and gastric toxicity. This may include pericellular and intracellular transport mechanisms of small molecules, peptides, metabolites, salts. The gastric tissues disclosed herein may further be used to assess compatibility with any agent and/or device that is intended to come into contact with the gastric tissues to assess biocompatibility.

In some embodiments, a gastric cell, gastric tissue and/or gastric hGO described herein can be used to identify the molecular basis of normal human gastric development.

In some embodiments, a gastric cell, gastric tissue and/or gastric hGO described herein can be used to identify the molecular basis of congenital defects affecting human gastric development.

In some embodiments, a gastric cell, gastric tissue and/or gastric hGO described herein can be used to correct gastric congenital defects caused by genetic mutations. In particular, mutation affecting human gastric development can be corrected using iPSC technology and genetically normal gastric tissue or related cell types described herein. In some embodiments, gastric tissue or related cell types described herein can be used to generate replacement tissue. Examples of genetic diseases include but are not limited to Neurog3 mutations and Enteric anendocrinosis, PTF1A mutations and neonatal diabetes, PDX1 mutations that effect enteroendocrine cells of the stomach.

In some embodiments, a gastric cell, gastric tissue and/or gastric hGO described herein can be used to generate replacement gastric tissue for diseases or conditions such as peptic ulcer disease, Ménétrier's disease, or for gastric cancer patients.

In some embodiments, a gastric cell, gastric tissue and/or gastric hGO described herein can be used to study microbiotic interactions with the human host epithelium and host immunity.

In some embodiments, gastric tissue or related cell types described herein, in particular the enteroendocrine cells can be used to study hormonal regulation of feeding behavior, metabolism, mediated by gastric endocrine.

In some embodiments, a gastric cell, gastric tissue and/or gastric hGO described herein, in particular the enteroendocrine cells that produce the hormone gastrin or ghrelin can be used to study and improve, for example, metabolic control in patients with obesity, metabolic syndrome, or Type 2 diabetes.

In some embodiments, a gastric cell, gastric tissue and/or gastric hGO described herein can be used to replace any damaged or removed gastric tissue in a subject in need thereof.

In some embodiments, a gastric cell, gastric tissue and/or gastric hGO described herein can be used to screen for toxicity and efficacy of any drug that acts on the gastric tissues.

In some embodiments where a gastric cell, gastric tissue and/or gastric hGO described herein are used to determine the absorption level of a compound, the compound will be contacted with the gastric cell, gastric tissue and/or gastric hGO with a compound; and a level of absorption of the compound by the gastric cell, gastric tissue and/or gastric hGO can be quantified. In some embodiments, the compound may be labeled with a radio-isotope, a fluorescent label and or a primary or secondary visible marker.

In some embodiments, a diagnostic kit or package is developed to include the gastric cell, gastric tissue and/or gastric hGO described herein and based on one or more of the aforementioned utilities.

Having described the invention in detail, it will be apparent that modifications, variations, and equivalent embodiments are possible without departing the scope of the invention defined in the appended claims. Furthermore, it should be appreciated that all examples in the present disclosure are provided as non-limiting examples.

EXAMPLES

The following non-limiting examples are provided to further illustrate embodiments of the invention disclosed herein. It should be appreciated by those of skill in the art that the techniques disclosed in the examples that follow represent approaches that have been found to function well in the practice of the invention, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention.

Pluripotent Stem Cell Culture

Human embryonic stem cell lines WA01 (H1) and WA09 (H9) were obtained from WiCell. ESC and iPSC lines were maintained as colonies in feeder-free conditions on HESC-qualified Matrigel (BD Biosciences) in mTesR1 media (Stem Cell Technologies). Cells were routinely passaged every four days with dispase (Invitrogen).

DE Induction.

Figure 14:
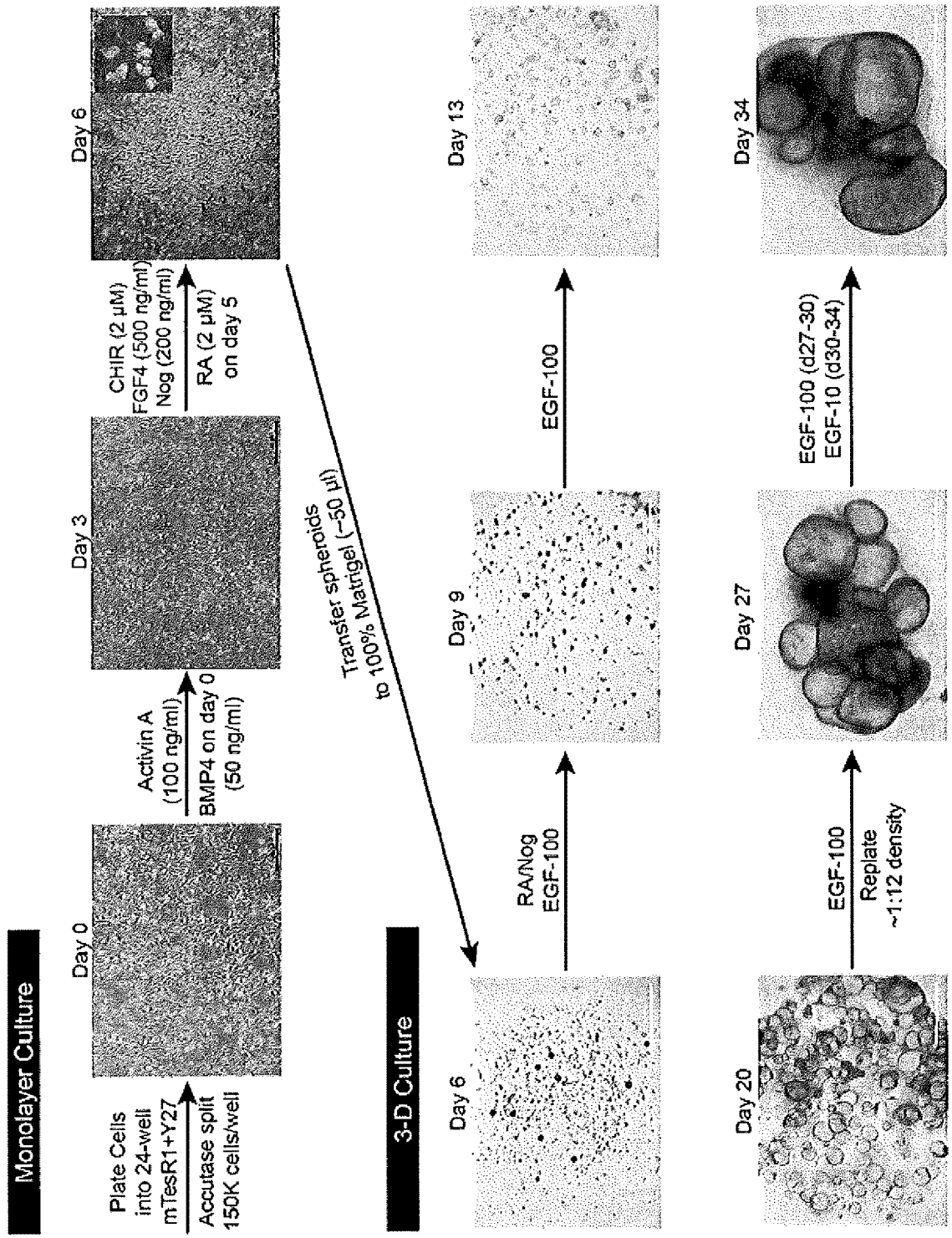
FIG. 14 shows a summary of methods for the directed differentiation of gastric organoids. Each step in the differentiation process is indicated, along with representative stereomicrographs.

(Summarized in FIG. 14.) Human ES and iPS cells were plated as single cells in mTesR1 media plus ROCK inhibitor Y27632 (10 M; Stemgent) in a Matrigel (BD Biosciences)-coated 24-well plate at 150,000 cells per well. The ROCK inhibitor enhances the survival of stem cells after plating for differentiation. Beginning the next day, cells were treated with Activin A (100 ng ml−1; Cell Guidance Systems) for three days in RPMI 1640 (Invitrogen) containing increasing concentrations of 0%, 0.2%, and 2.0% define fetal bovine serum (dFBS; Invitrogen).

Differentiation of Definitive Endoderm (DE)

For differentiation, PSCs were plated as single cells in a Matrigel-coated 24-well dish using accutase (Stem Cell Technologies), at a density of 150,000 cells per well in mTesR1 with ROCK inhibitor Y-27632 (10 µM; Stemgent). On the following day, PSCs were differentiated to DE as previously described[11, 35]. Cells were exposed to Activin A (100 ng ml−1; Cell Guidance Systems) for three days in RPMI 1640 media (Invitrogen) containing increasing concentrations of 0%, 0.2%, and 2.0% define fetal bovine serum (dFBS; Invitrogen). In addition, BMP4 (50 ng ml−1; R&D Systems) was added on the first day of DE induction.

Endoderm Patterning and Gut Tube Morphogenesis.

Following DE induction, cells were treated for three days with growth factors/antagonists in RPMI 1640 with 2.0% dFBS. To generate posterior foregut spheroids, DE was treated for three days with noggin (200 ng ml−1; R&D Systems), FGF4 (500 ng ml−1; R&D Systems), and either WNT3A (500 ng ml−1; R&D Systems) or CHIR99021 (2 µM; Stemgent). CHIR99021 is a small molecule that stimulates the Wnt signaling pathway. RA (2 µM; Sigma Aldrich) is added on the final day. Three-dimensional growth and antral specification. Posterior foregut spheroids were embedded in Matrigel (BD Biosciences) as previously described[10, 12] and subsequently grown in Advanced DMEM/F12 (Invitrogen) supplemented with N2 (Invitrogen), B27 (Invitrogen), L-glutamine, M HEPES, penicillin/streptomycin, and EGF (100 ng ml−1; R&D Systems). For antral specification, RA and noggin were added for the first three days of three-dimensional growth. For endocrine cell specification, the EGF concentration is lowered to 10 ng ml$^{-1}$ at day 30.

Endoderm Patterning and Foregut Spheroid Generation

Following DE induction, cells were cultured in RPMI 1640 media with 2.0% dFBS and growth factors: WNT3A (500 ng ml−1; R&D Systems), CHIR99021 (2 µM; Stemgent); FGF4 (500 ng ml−1; R&D Systems), and Noggin (200 ng ml−1; R&D Systems). The media was changed every day. After three days, the combination of WNT3A (or CHIR99021), FGF4, and Noggin resulted in floating foregut spheroids in the culture wells. To posteriorize the foregut endoderm, RA (2 µM; Sigma Aldrich) was added on the third day of WNT/FGF/Noggin treatment.

Three-Dimensional Culture of Gastric Organoids

The spheroids were transferred to a three-dimensional in vitro culture system as previously described 5,10,12. Briefly, spheroids were collected, resuspended in 50 µl Matrigel (BD Biosciences), and plated in a three-dimensional droplet. After Matrigel was allowed to solidify for 10-15 minutes in a tissue culture incubator, spheroids were overlaid with gut media: Advanced DMEM/F12 with N2 (Invitrogen), B27 (Invitrogen), L-glutamine, 10 µM HEPES, penicillin/streptomycin, and EGF (100 ng ml−1; R&D Systems). For the first three days, RA and Noggin were added to the gut media.

Media was replaced every 3-4 days, as necessary. At day 20, organoids were collected and re-plated in fresh Matrigel at dilution of ~1:12.

Generation of Dox-Inducible hNEUROG3 hESC Line

To generate over-expression construct, hNEUROG3 cDNA (Dana-Farber/Harvard Cancer Center DNA Resource Core; clone HsCD00345898) was cloned into pInducer20 lentiviral vector (gift from T. Westbrook36) using Gateway Cloning (Invitrogen) methods. High-titer lentiviral particles were produced by the CCHMC Viral Vector Core. H1 hESCs were dissociated with Accutase, plated as a single cell suspension in mTesR1 with 10 μM Y-27632, and exposed to lentivirus for four hours. mTesR1 was replaced daily and after two days, G418 (200 μg ml−1) was added to the media to select for integrating clones. G418-resistant cells were maintained in antibiotic indefinitely, but were otherwise cultured and passaged normally.

Generation and Characterization of iPSC Lines

Primary human foreskin fibroblasts (HFFs) were cultured from neonatal human foreskin tissue and obtained from 2 donors through the Department of Dermatology, University of Cincinnati, and were a kind gift from Susanne Wells PhD. HFFs were cultured in Fibroblast Media consisting of DMEM (Invitrogen) supplemented with 10% FCS (Hyclone) and used for reprogramming between passages 5 and 8. EBNA1/OriP-based episomal plasmids pCLXE-hOct3/4-shp53, pCLXE-hSox2-Klf4, pCLXE-hLmyc-Lin28, and pCLXE-GFP used for this study were previously described37 and obtained from Addgene (ID #s: 27077, 27078, 27080, and 27082 respectively). The optimized Human Dermal Fibroblast Nucleofector Kit (VPD-1001; Lonza) was used for transfection of HFFs with episomal plasmids. Briefly, for each transfection 1×106 HFFs were pelleted by centrifugation at 200×g for 10 minutes at room temperature, resuspended in 100 μl room temperature Nucleofector Solution and nucleofected with 1.25 μg each episomal plasmid (program U20). Cells from 2 transfections (2×106 total cells) were replated in a 10 cm tissue culture plate in Fibroblast Media, and cultured at 37° C./5% C02. Six days post-transfection, 4.5×105 HFFs were replated in Fibroblast Media in a gelatin-coated 10 cm dish containing 1.07×106 irradiated mouse embryonic fibroblasts (MEFs). Starting on day 7 post-transfection, cells were fed daily with DMEM/F12 media supplemented with 20% knockout serum replacement, 1 mM L-glutamine, 0.1 mM β-mercaptoethanol, 0.1 mM non-essential amino acids, and 4 ng ml−1 basic FGF (all from Invitrogen). Approximately 2 weeks later, discrete colonies with hESC-like morphology were manually excised and replated in mTeSR1 media (Stem Cell Technologies) in tissue culture dishes coated with hESC-qualified matrigel (Becton Dickinson). Following adaptation to mTeSR1/matrigel culture, iPSCs that maintained robust proliferation and hESC-like morphology with minimal spontaneous differentiation were expanded for cryopreservation and characterization.

Standard metaphase spreads and G-banded karyotypes were determined by the CCHMC Cytogenetics Laboratory. For teratoma formation, iPSCs from 3 wells of a 6-well dish were combined and gently resuspended in ice-cold DMEM/F12. Immediately before injection, matrigel was added to a final concentration of ~33% and cells were injected subcutaneously into immune-compromised NOD/SCID GAMMA C−/− mice. Tumors formed within 6-12 weeks. Excised teratomas were fixed, embedded in paraffin, and sections were stained with hematoxylin and eosin for histological examination.

Exemplary Protocol for Gastric Organoid

The following Table illustrates an exemplary treatment protocol for the development of a gastric organoid from a precursor cell.

| Day | Media | Treatment | Stage of Development/Outcome |
|---|---|---|---|
| −1 | mTesR1 | Y27632 (10 uM) | |
| 0 | RPMI | Activin A (100 ng/mL) + BMP4 (50 ng/mL) | Monolayer hPSCs (ready to differentiate) |
| 1 | RPMI + 0.2% dFCS | Activin A (100 ng/mL) | |
| 2 | RPMI + 2.0% dFCS | Activin A (100 ng/mL) | |
| 3 | RPMI + 2.0% dFCS | FGF4 (500 ng/mL) + Wnt3a (500 ng/mL) OR CHIR99021 (2 uM) | Definitive Endoderm |
| 4 | RPMI + 2.0% dFCS | FGF4 (500 ng/mL) + Wnt3a (500 ng/mL) OR CHIR99021 (2 uM) | |
| 5 | RPMI + 2.0% dFCS | RA (2 uM) + FGF4 (500 ng/mL) + Wnt3a (500 ng/mL) OR CHIR99021 (2 uM) | |
| 6 | Basal Gut Media | EGF (100 ng/mL) + RA (2 uM) + Noggin (200 ng/mL) | 3-D Posterior Foregut Spheroid |
| 7 | Basal Gut Media** | EGF (100 ng/mL) + RA (2 uM) + Noggin (200 ng/mL) | |
| 8 | Basal Gut Media** | EGF (100 ng/mL) + RA (2 uM) + Noggin (200 ng/mL) | |
| 9 | Basal Gut Media** | EGF (100 ng/mL) + Noggin (200 ng/mL) | Presumptive Antral Epithelium (Pdx1/Sox2) |
| 10 | Basal Gut Media** | EGF (100 ng/mL) + Noggin (200 ng/mL) | |
| 11 | Basal Gut Media** | EGF (100 ng/mL) + Noggin (200 ng/mL) | |
| 12 | Basal Gut Media** | EGF (100 ng/mL) + Noggin (200 ng/mL) | |
| 13 | Basal Gut Media** | EGF (100 ng/mL) | |
| 14 | Basal Gut Media** | EGF (100 ng/mL) | |
| 15 | Basal Gut Media** | EGF (100 ng/mL) | |
| 16 | Basal Gut Media** | EGF (100 ng/mL) | |
| 17 | Basal Gut Media** | EGF (100 ng/mL) | |

-continued

| Day | Media | Treatment | Stage of Development/Outcome |
|---|---|---|---|
| 18 | Basal Gut Media** | EGF (100 ng/mL) | |
| 19 | Basal Gut Media** | EGF (100 ng/mL) | |
| 20 | Basal Gut Media** | EGF (100 ng/mL) | |
| 21 | Basal Gut Media** | EGF (100 ng/mL) | |
| 22 | Basal Gut Media** | EGF (100 ng/mL) | |
| 23 | Basal Gut Media** | EGF (100 ng/mL) | |
| 24 | Basal Gut Media** | EGF (100 ng/mL) | |
| 25 | Basal Gut Media** | EGF (100 ng/mL) | |
| 26 | Basal Gut Media** | EGF (100 ng/mL) | |
| 27 | Basal Gut Media** | EGF (100 ng/mL) | |
| 28 | Basal Gut Media** | EGF (100 ng/mL) | |
| 29 | Basal Gut Media** | EGF (100 ng/mL) | |
| 30 | Basal Gut Media** | EGF (100 ng/mL) | |
| 31 | Basal Gut Media** | EGF (10 ng/mL) | |
| 32 | Basal Gut Media** | EGF (10 ng/mL) | |
| 33 | Basal Gut Media** | EGF (10 ng/mL) | |
| 34 | Basal Gut Media** | EGF (10 ng/mL) | Gastric Organoids with Differentiated Cell Types |

**Basal Gut Media = Advanced DMEM/F12 + B27 + N2 + 1-glutamine + HEPES;
mTesR1 is available from StemCell Technologies.

Fundus Specification Protocol

Figure 15:
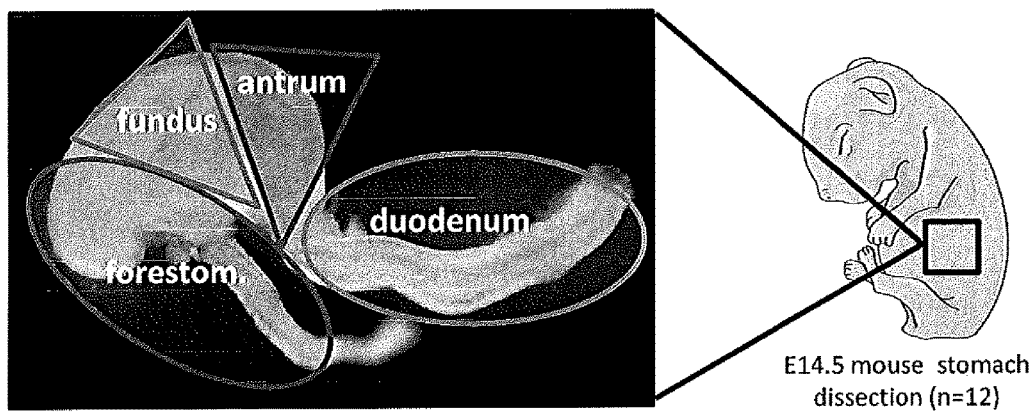
FIG. 15 depicts a schematic of the mouse stomach and measurement of known regional markers in the forestomach, fundus, antrum, and duodenum.
Figure 15:
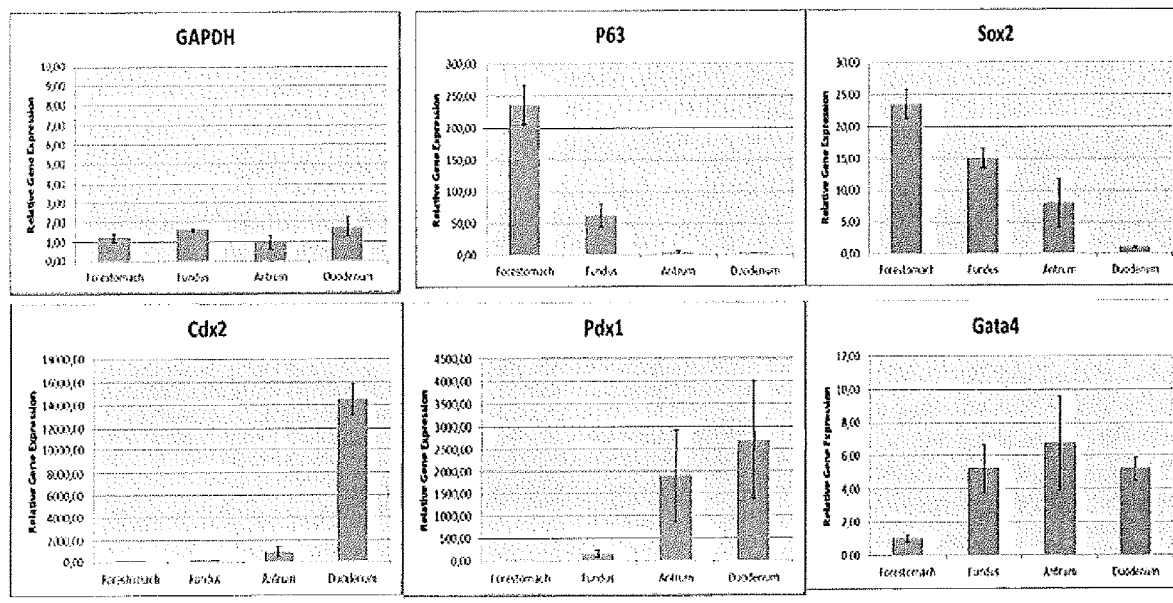

Applicant first sought to identify genes specifically expressed in the fundus, but not in the antrum, at embryonic stages. The digestive tracts of E14.5 mouse embryos were micro-dissected and separated into four regions: forestomach (including esophagus), fundus, antrum, and duodenum. See FIG. 15. These regions were then analyzed by qPCR for markers of regionalization. FIG. 15 shows expression of control genes known to be expressed in different regions. The fundus and antrum can be distinguished from the forestomach and duodenum by their high expression of Sox2 and Gata4, and absence of P63 and Cdx2. Importantly, Pdx1 (marker of antrum) is expressed at much higher levels in the antrum tissue than in the fundus, indicating accurate dissection.

Figure 16:
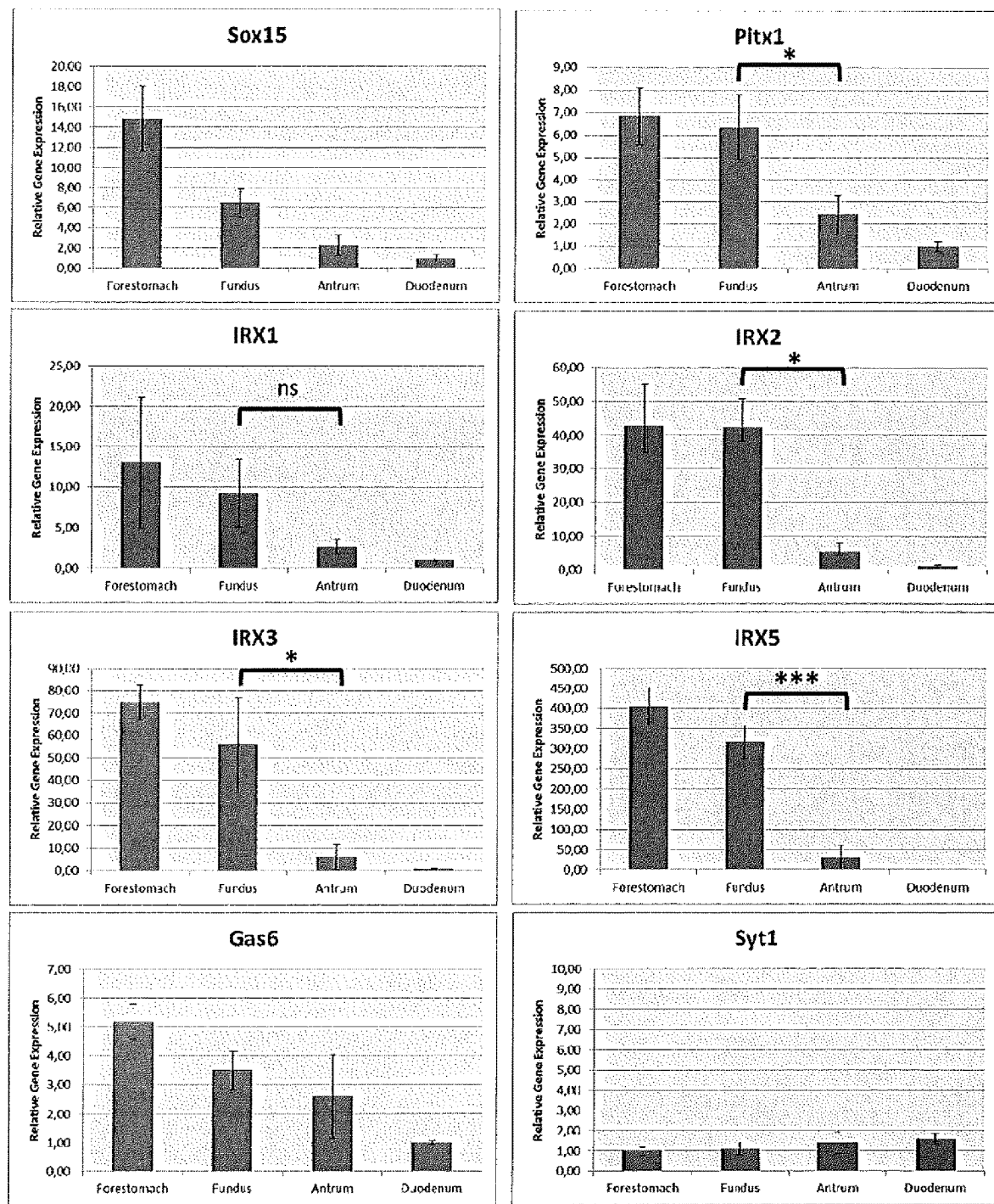
FIG. 16 depicts measurement of new regional markers in the forestomach, fundus, antrum, and duodenum.

Bioinformatics analysis of published microarray datasets from embryonic mouse endoderm and adult human stomach tissue were used to generate a list of candidate genes that may be preferentially expressed in the fundus but not antrum. Expression of these putative markers in the E14.5 mouse segments was examined by qPCR. Irx1, Irx2, Irx3, Irx5, and Pitx1 are indeed expressed at higher levels in the fundus than in the antrum. Thus these markers may be used as indicators of fundus specification in the hPSC-derived foregut cultures. See FIG. 16.

Figure 17:
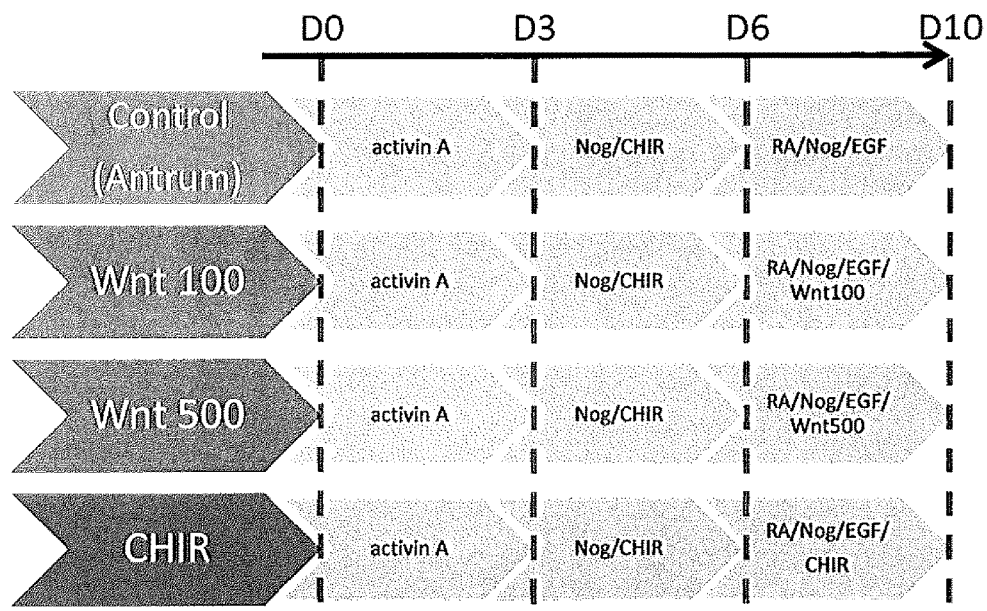
FIG. 17 depicts the fundus specification protocol and measurement of GAPDH, Gata4, Axin2, Sox2, Pdx1, and Cdx2 in control, Wnt100, Wnt500 and CHIR treated cells. The y axis represents relative gene expression.
Figure 17:
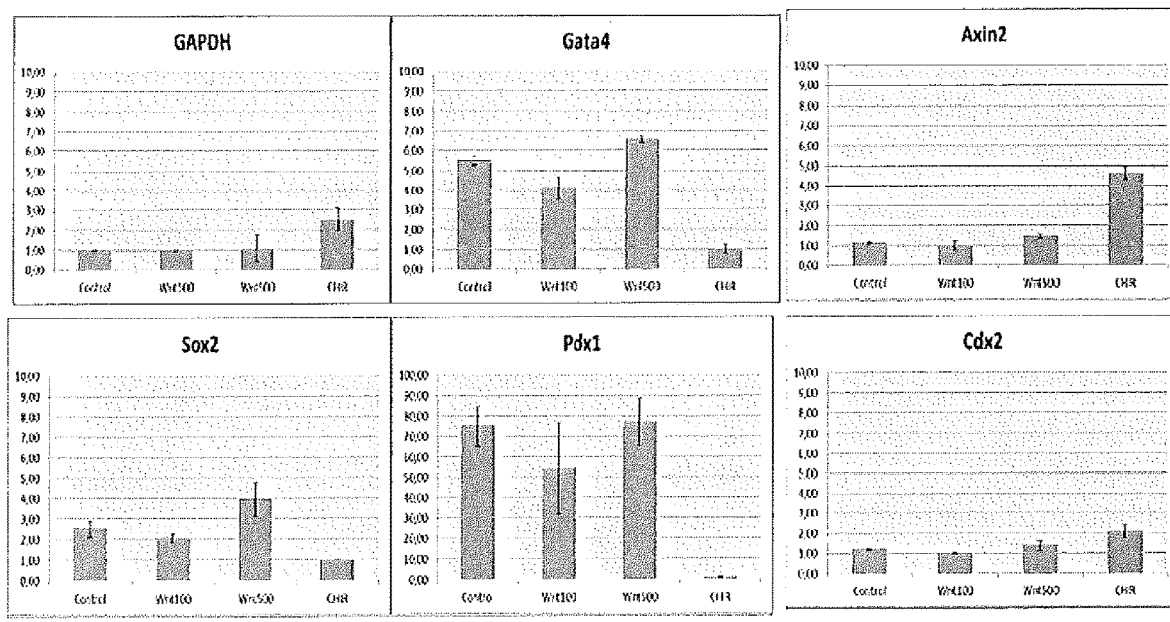
Figure 18:
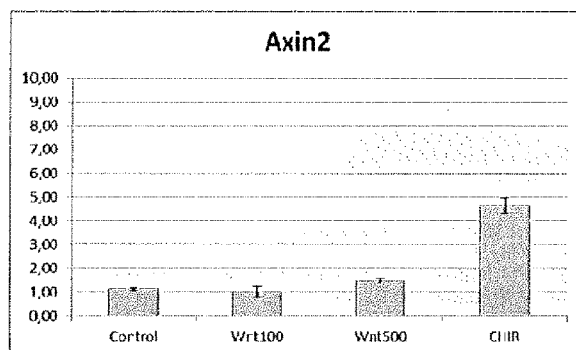
FIG. 18 depicts measurements of Axin2, IRX2, IRX3, Pitx1, and IRX4 in the fundus protocol. The y axis represents relative gene expression.
Figure 18:
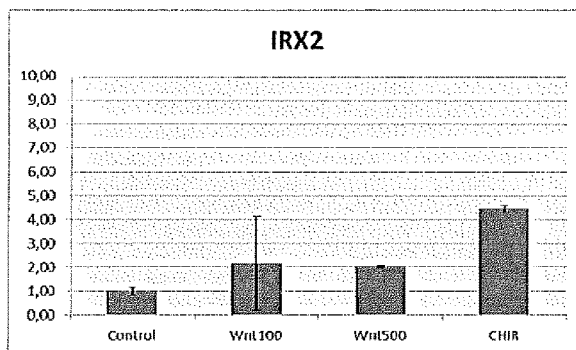
Figure 18:
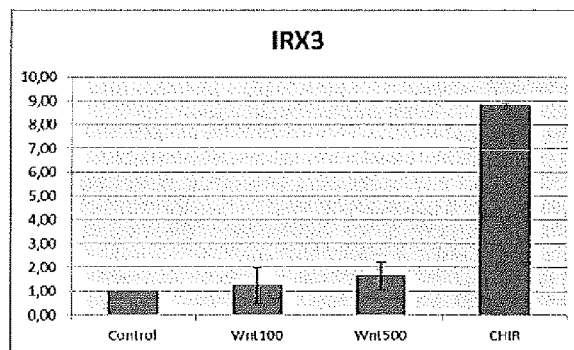
Figure 18:
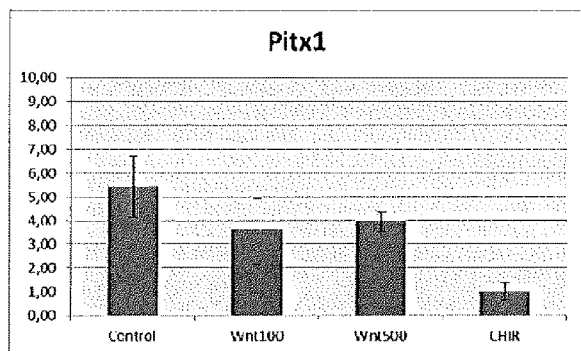
Figure 18:
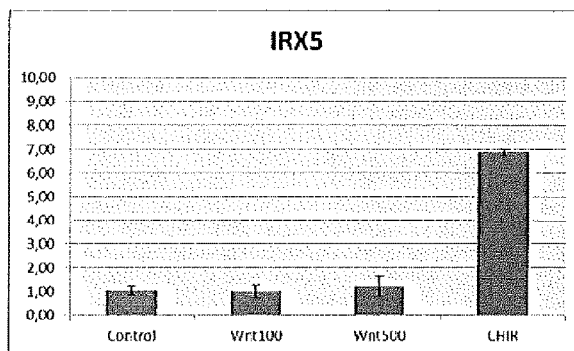
Figure 19:
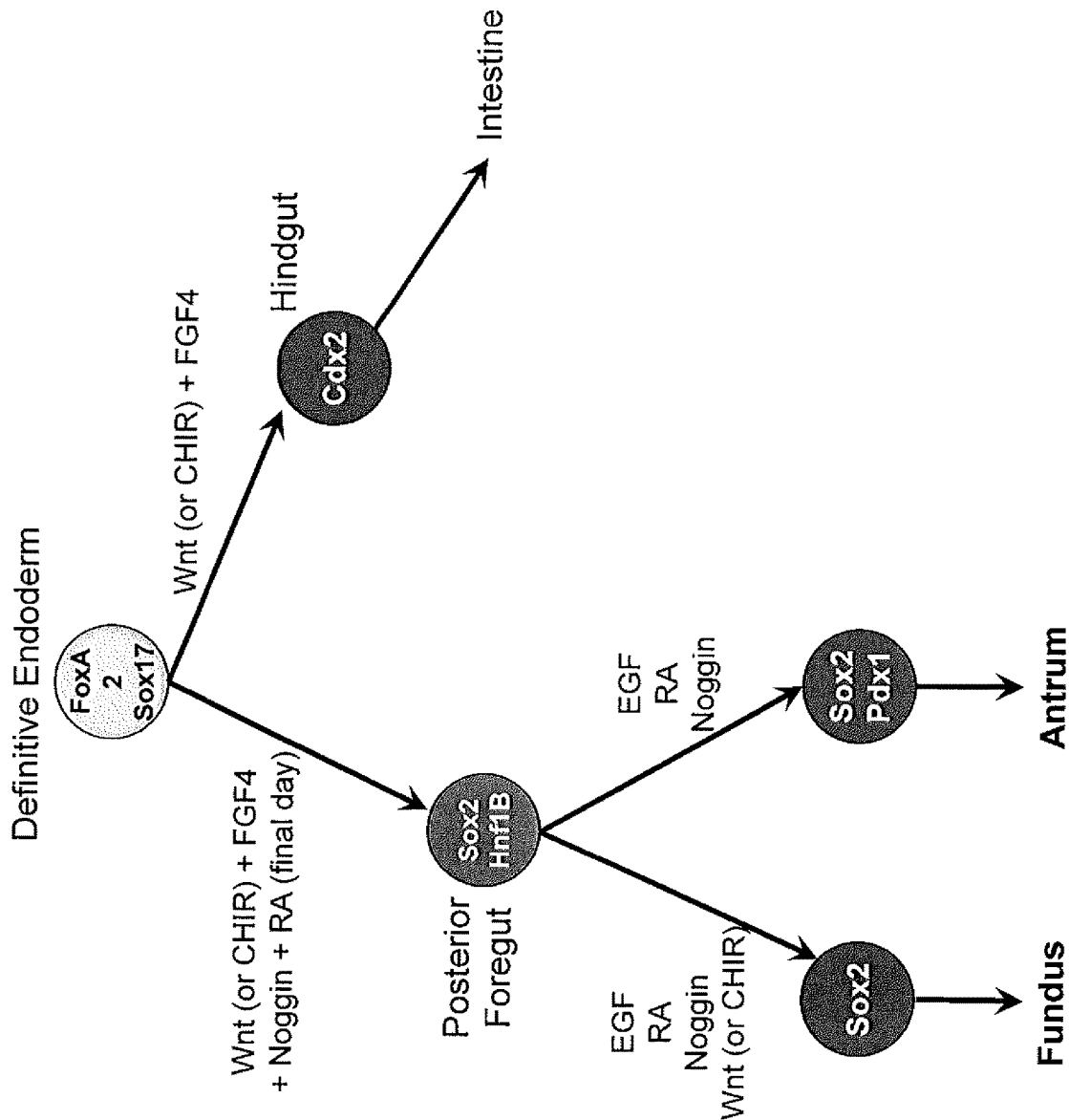
FIG. 19 is a schematic depicting the formation of intestine tissue, fundus tissue, and antrum tissue from definitive endoderm.

Next, the function of Wnt signaling in the regulation of fundus-antrum patterning at days 6-9 of the gastric organoid differentiation protocol was tested. Addition of Wnt3a (at 100 ng/mL and 500 ng/mL) had no effect on spheroid gene expression, but it also did induce expression of the Wnt target gene Axin2. Thus, the effects of the small molecule CHIR99021 (CHIR; 2 uM) were tested. CHIR99021 stimulates Wnt signaling in a receptor-independent fashion. Exposure to CHIR resulted in a robust repression of Pdx1 expression levels, consistent with fundus specification. CHIR did not induce expression of the intestinal marker Cdx2. See FIG. 17. FIG. 18 shows that, consistent with repression of Pdx1, exposure to CHIR induced high levels of expression of fundus-specific markers IRX3 and IRX5.

H. pylori Infection

H. pylori strain G2738 and a mutant G27 strain lacking CagA (ΔCagA)39 were grown on blood agar plates consisting of Columbia Agar Base (Fisher Scientific), 5% horse blood (Colorado Serum Company), 5 µg ml−1, vancomycin and 10 µg ml−1 trimethoprim as described previously 40. For organoid injections, H. pylori were resuspended in brucella broth at a concentration of 1×109 bacteria ml−1 and loaded onto the Nanoject II (Drummond) microinjector apparatus. Approximately 200 nl (containing 2×105 bacteria) were injected directly in the lumen of each organoid, and injected organoids were cultured for 24 hours. Brucella broth was injected as a negative control.

Materials and Methods

Immunofluorescent Staining

All tissues were fixed in 4% paraformaldehyde for either one hour at room temperature for frozen processing or overnight at 4° C. for paraffin processing. For frozen sections, tissue was protected in 30% sucrose overnight at 4° C., then embedded in OCT (Tissue-Tek), and cut at 10 µm. For paraffin sections, tissue was processed through a graded ethanol series, followed by xylene, and then embedded in paraffin and cut at 7 µm. Tissue culture cells were fixed for 15 minutes at room temperature and stained directly. For staining, frozen slides were thawed to room temperature and rehydrated in PBS, while paraffin slides were deparaffinized and subjected to antigen retrieval. Slides were blocked in 5% normal donkey serum (Jackson Immuno Research) in PBS plus 0.5% Triton-X for 30 minutes at room temperature. Primary antibodies (listed in Methods Table 1) were diluted in blocking buffer and incubated overnight at 4° C. Slides were washed in PBS and incubated with secondary antibody for one hour at room temperature, and coverslips were mounted using Fluoromount-G (Southern Biotech). Confocal images were captured on a Nikon A1Rsi inverted confocal microscope.

RNA Isolation and qPCR

Total RNA was isolated from tissues using the Nucleospin RNA II kit (Machery-Nagel). Reverse transcription was performed from 100 ng RNA using Superscript VILO cDNA Synthesis Kit (Invitrogen) according to manufacturer's protocol. qPCR was done using Quantitect SybrGreen Master Mix (Qiagen) on a CFX-96 Real-time PCR Detection System (BioRad). Analysis was performed using the AACT method. PCR primers were designed using sequences from qPrimerDepot (http://primerdepot.nci.nih.gov) and are listed in Table 2.

Immunoprecipitation and Western Blot Analysis

*H. pylori*-infected organoids were harvested from Matrigel in ice-cold PBS and centrifuged at 150 g for 5 minutes. Tissue was lysed in M-PER Mammalian Protein Extract Reagent (Thermo Scientific) supplemented with protease inhibitors (Roche). 10 µg total protein from the cell lysates were immunoprecipitated with anti-c-Met antibody (2 µg; Cell Signaling 4560) at 4° C. for 16 hours. Protein A/G agarose beads (20 µl; Santa Cruz Biotechnology) were then added and the samples were incubated at 4° C. for 16 hours. Immunoprecipitates were washed 3 times in PBS and then resuspended in Laemmli Loading Buffer containing β-mercaptoethanol (40 µl; BioRad). Samples were run on a 4-20% Tris-Glycine Gradient Gel (Invitrogen) and run at 80 V for 3.5 hours. Gels were transferred to nitrocellulose membranes (Whatman Protran, 0.45 µm) at 105 V for 1.5 hours. Membranes were blocked in KPL Detector Block Solution (Kirkeaard & Perry Laboratories) for one hour at room temperature and then incubated with primary antibody overnight at 4° C. Primary antibodies used: anti-phosphotyrosine (Santa Cruz, sc-7020; 1:100), anti-c-Met (Abcam, ab59884; 1:100), and anti-*H. pylori* CagA (Abcam, ab90490; 1:100). Membranes were washed and incubated in Alexa Fluor anti-mouse 680 (Invitrogen; 1:1000) secondary antibody. Blots were imaged using the Odyssey Infrared Imaging Software System (Licor).

Discussion hPSCs were differentiated into definitive endoderm (DE)[11], which gives rise to the epithelia of the gastrointestinal and respiratory tracts in vivo. The next two essential events in development of all endoderm organs are patterning of DE along the anterior-to-posterior (A-P) axis and gut tube morphogenesis, resulting in formation of the Sox2+ foregut in the anterior and the Cdx2+ mid-hindgut in the posterior (as highlighted in the E8.5, 14 somite stage mouse embryo, FIG. 1A). This morphogenesis and the tissue interactions between endoderm and mesoderm appear to be critical for proper organogenesis both in vivo and in vitro. WNT3A and FGF4 have been previously demonstrated to synergize to do three things: posteriorize hPSC-derived DE, promote the expansion of mesenchyme, and induce the assembly of gut tube-like structures expressing the mid-hindgut marker CDX2[10,12]. FIG. 1A shows that Sox2 protein marks foregut endoderm and Cdx2 protein marks mid/hindgut endoderm in e8.5 (14 somite stage) mouse embryos. FIG. 1B shows that inhibiting BMP repressed mid/hindgut fate and promoted expression of the foregut marker SOX2. PCR analysis of patterning markers in hPSC-DE cultures exposed to three days in media alone (control) or with the indicated growth factors/antagonists. The combined activity of WNT and FGF induced CDX2 expression as previously reported[10] whereas the BMP antagonist noggin repressed CDX2 expression and was sufficient to induce high levels of the foregut marker SOX2. *, $p<0.05$ compared to control. **, $p<0.005$ compared to WNT/FGF. FIG. 1C depicts that foregut spheroids generated with Wnt/FGF/Noggin have high levels of SOX2 protein by wholemount immunofluorescence staining and mRNA as compared to spheroids generated with Wnt and FGF alone, which have high levels of CDX2. *, $p<1.0\times10^{-6}$. FIG. 1D depicts that the posterior foregut in an e8.5, 14-somite stage mouse embryo gives rise to the stomach and pancreas and has high levels of Hnf1β protein. FIG. 1E depicts that exposing cultures to RA on the final day of the spheroid generation step induces expression of HNF1β in SOX2-expressing epithelium, resulting in the formation of posterior foregut spheroids. *, $p<0.005$. FIG. 1F depicts a lineage diagram that summarizes the patterning effects of noggin and RA in the formation of both anterior and posterior foregut endoderm. Scale bars, 100 µm. Error bars represent standard deviation.

TABLE 1

Primary Antibodies.

| Antibody | Species | Company | Product No. | Dilution |
|---|---|---|---|---|
| alpha-SM-actin | rabbit | GeneTex | GTX100034 | 1:200 |
| aPKC | rabbit | Santa Cruz | sc216 | 1:200 |
| B-catenin | rabbit | Santa Cruz | sc7199 | 1:100 |
| Cdx2 | mouse | Biogenex | MU392A-UC | 1:500 |
| ChrA | rabbit | Immunostar | 20086 | 1:500 |
| Desmin | goat | Santa Cruz | sc7559 | 1:200 |
| E-Cadherin | mouse | BD Biosciences | 610182 | 1:500 |
| E-Cadherin | goat | R&D Systems | AF648 | 1:500 |
| FoxF1 | goat | R&D Systems | AF4798 | 1:500 |
| Gastrin | rabbit | Dako | A0568 | 1:1000 |
| Gata4 | mouse | Santa Cruz | sc25310 | 1:200 |
| Ghrelin | goat | Santa Cruz | sc10368 | 1:200 |
| H. pylori | rabbit | Abcam | ab80519 | 1:1000 |
| Hnf1B | mouse | BD Biosciences | 612504 | 1:500 |
| Hnf1B | goat | Santa Cruz | sc4711 | 1:500 |
| Ki67 | rabbit | Abcam | ab833 | 1:200 |
| Ki67 | rat | Dako | m7249 | 1:100 |
| Klf5 | rat | Dr. Ryozo Nagai | Shindo et al., 2002 | 1:2000 |
| Muc5AC | mouse | Abcam | ab3649 | 1:500 |
| Nanog | rabbit | Abcam | ab21624 | 1:500 |
| Oct3/4 | mouse | Santa Cruz | sc5279 | 1:500 |
| Pdx1 | goat | Abcam | ab47383 | 1:5000 |
| pHH3 | rabbit | Cell Signaling | 9701 | 1:500 |
| Serotonin (5-HT) | rabbit | Immunostar | 20080 | 1:1000 |
| Somatostatin | goat | Santa Cruz | sc7819 | 1:100 |
| Sox2 | goat | Santa Cruz | sc17320 | 1:500 |
| Sox2 | rabbit | Seven Hills Bioreagents | WRAB-1236 | 1:1000 |
| Tff2 | goat | Santa Cruz | sc23558 | 1:500 |
| Vimentin | goat | Santa Cruz | sc7557 | 1:200 |

TABLE 2 qPCR Primer Sequences.

| Target (Human) | Forward Primer | Reverse Primer |
|---|---|---|
| ATP4A | TGGTAGTAGCCAAAGCAGCC | TGCCATCCAGGCTAGTGAG |
| ATP4B | ACCACGTAGAAGGCCACGTA | TGGAGGAGTTCCAGCGTTAC |
| AXIN2 | CTGGTGCAAAGACATAGCCA | AGTGTGAGGTCCACGGAAAC |
| BAPX1 | CAACACCGTCGTCCTCG | CCGCTTCCAAAGACCTAGAG |
| CDX2 | CTGGAGCTGGAGAAGGAGTTTC | ATTTTAACCTGCCTCTCAGAGAGC |
| CHGA | TGACCTCAACGATGCATTTC | CTGTCCTGGCTCTTCTGCTC |
| GAPDH | CCCATCACCATCTTCCAGGAG | CTTCTCCATGGTGGTGAAGACG |
| GAST | CAGAGCCAGTGCAAAGATCA | AGAGACCTGAGAGGCACCAG |
| GATA4 | TCCAAACCAGAAAACGGAAGC | GCCCGTAGTGAGATGACAGG |
| GHRL | GCTGGTACTGAACCCCTGAC | GATGGAGGTCAAGCAGAAGG |
| GKN1 | AGCTAGGGCAGGAGCTAGAAA | GCTTGCCTACTCCTCTGTCC |
| HNF1B | TCACAGATACCAGCAGCATCAGT | GGGCATCACCAGGCTTGTA |
| HNF6 | TGTTGCCTCTATCCTTCCCA | GGAGGATGTGGAAGTGGCT |
| IRX1 | CCGTAGGGGTAATAAGCCG | ATCTCAGCCTCTTCTCGCAG |
| IRX2 | GTGGTGTGCGCGTCGTA | GGCGTTCAGCCCCTACC |
| IRX3 | GGAGAGAGCCGATAAGACCA | AGTGCCTTGGAAGTGGAGAA |
| IRX5 | GGTGTGTGGTCGTAGGGAGA | GCTACAACTCGCACCTCCA |
| MIST1 | TGCTGGACATGGTCAGGAT | CGGACAAGAAGCTCTCCAAG |
| MSX1 | GGTTCGTCTTGTGTTTGCG | CCCGAGAAGCCCGAGAG |
| MSX2 | GGTCTTGTGTTTCCTCAGGG | AAATTCAGAAGATGGAGCGG |
| MUC2 | TGTAGGCATCGCTCTTCTCA | GACACCATCTACCTCACCCG |
| MUC5AC | CCAAGGAGAACCTCCCATAT | CCAAGCGTCATTCCTGAG |
| MUC6 | CAGCAGGAGGAGATCACGTTCAAG | GTGGGTGTTTTCCTGTCTGTCATC |
| NEUROG3 | CTTCGTCTTCCGAGGCTCT | CTATTCTTTTGCGCCGGTAG |
| PDX1 | CGTCCGCTTGTTCTCCTC | CCTTTCCCATGGATGAAGTC |
| PITX1 | TTCTTGGCTGGGTCGTCT | TCGTCTGACACGGAGCTG |
| PTF1a | AGAGAGTGTCCTGCTAGGGG | CCAGAAGGTCATCATCTGCC |
| SST | GCGCTGTCCATCGTCCTGGCCC | AGCCGGGTTTGAGTTAGCAGAT |
| SOX2 | GCTTAGCCTCGTCGATGAAC | AACCCCAAGATGCACAACTC |
| TFF1 | AATTCTGTCTTTCACGGGGG | GGAGAACAAGGTGATCTGCG |
| TFF2 | TCTGAGACCTCCATGACGC | ATGGATGCTGTTTCGACTCC |
| TFF3 | CACTCCTTGGGGGTGACA | CTCCAGCTCTGCTGAGGAGT |

Figure 5:
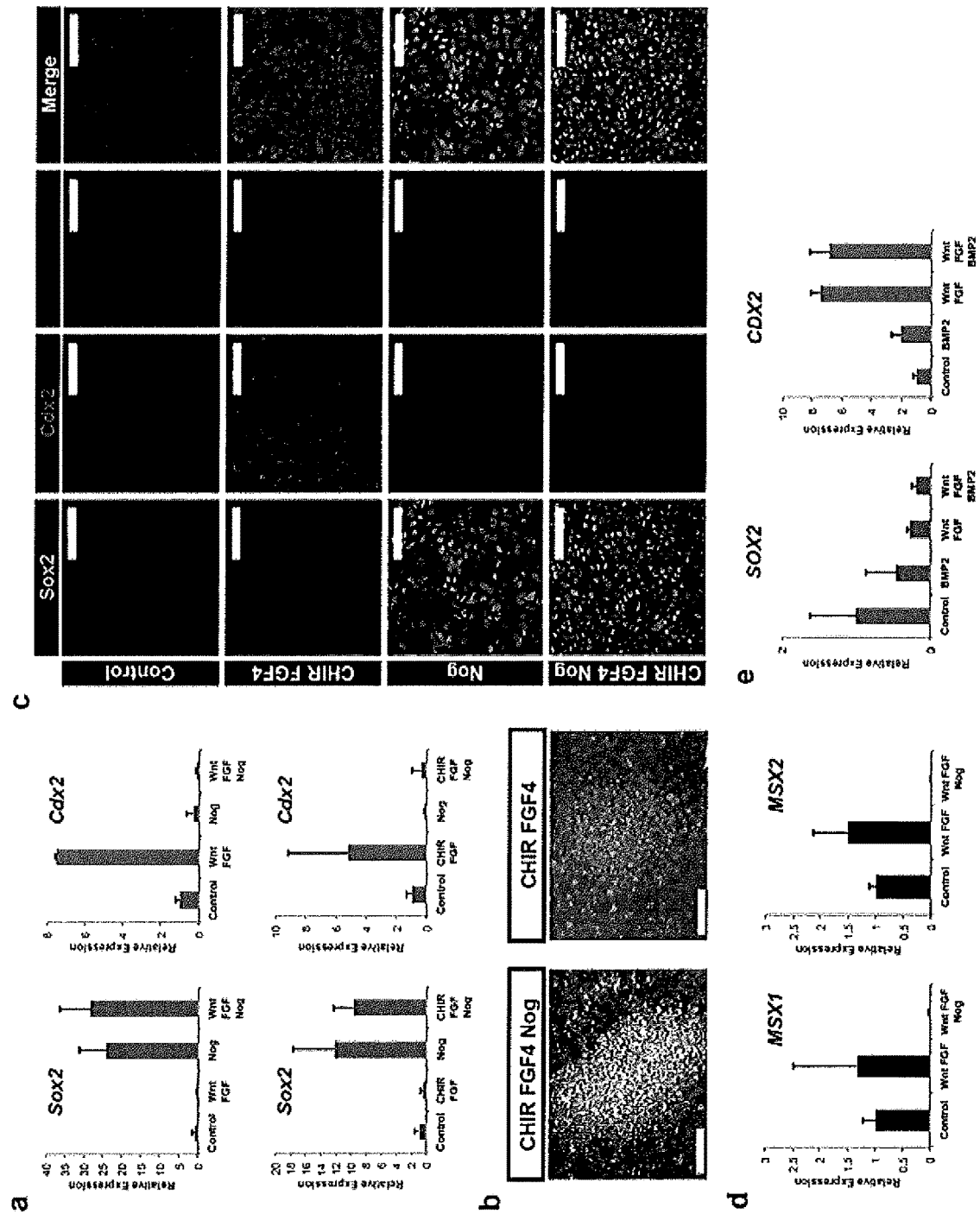
FIG. 5 depicts Sox2 and Cdx2 expression in the presence of GSK3β inhibitor CHIR99021 and recombinant WNT3A in the presence and absence of noggin (FIG. 5, Panel A), CHIR induced gut tube morphogenesis and spheroid production visualized using bright field microscopy (FIG. 5, Panel B), immunofluorescent staining of monolayer cultures to assess CDX2 induction in CHIR/FGF-treated endoderm and SOX2 induction in noggin- and CHIR/FGF/noggin-treated endoderm (FIG. 5, Panel C), qPCR analysis of BMP target genes MSX1/2 (FIG. 5, Panel D), and SOX2 and CDX2 (FIG. 5, Panel E) expression in the presence and absence of BMP2.

To promote the formation of foregut structures in the hPSC-derived DE, Applicant sought to separate the ability of WNT/FGF to stimulate gut tube morphogenesis from their role in promoting a posterior endoderm fate. Based on in vivo studies from developmental model organisms[13, 14], the function of BMP signaling in regulating A-P patterning was tested and Applicant determined that WNT/FGF require BMP activity to initiate the hindgut program. Specifically, inhibition of BMP signaling with the antagonist Noggin repressed CDX2 and induced the foregut marker SOX2 in DE cultures after three days, even in the presence of WNT/FGF (FIG. 1B-C and FIG. 5). Importantly, inhibition of BMP signaling had no effect on the ability of WNT/FGF to promote mesenchyme expansion and assembly of gut tube structures, thus resulting in the formation of SOX2$^+$ foregut spheroids.

FIG. 5 shows that BMP signaling is required in parallel with activation of WNT and FGF to promote a posterior fate. FIG. 5A shows that the GSK3β inhibitor CHIR99021 (CHIR; 2 μM) induced the same posteriorizing effects as recombinant WNT3A and these can be blocked by BMP inhibition. FIG. 5B shows that CHIR induced gut tube morphogenesis and spheroid production occurs in a similar manner to WNT3A. FIG. 5C depicts immunofluorescent staining of monolayer cultures which confirms the high efficiency of CDX2 induction in CHIR/FGF-treated endoderm and SOX2 induction in noggin- and CHIR/FGF/noggin-treated endoderm. FIG. 5D shows qPCR analysis of BMP target genes MSX1/2, which indicates that BMP activity is not increased in response to Wnt/FGF, but target genes are suppressed in response to noggin, demonstrating the presence of endogenous BMP signaling. FIG. 5E shows that addition of BMP2 (100 ng mL−1) did not substitute for or augment the ability of Wnt/FGF to posteriorize endoderm. These data indicate that the posteriorizing effect of Wnt/FGF is not mediated by up-regulation of BMP signaling but does require endogenous BMP activity. Scale bars, 1 mm in FIG. 5B; 100 μm in FIG. 5C. Error bars represent standard deviation.

Figure 6:
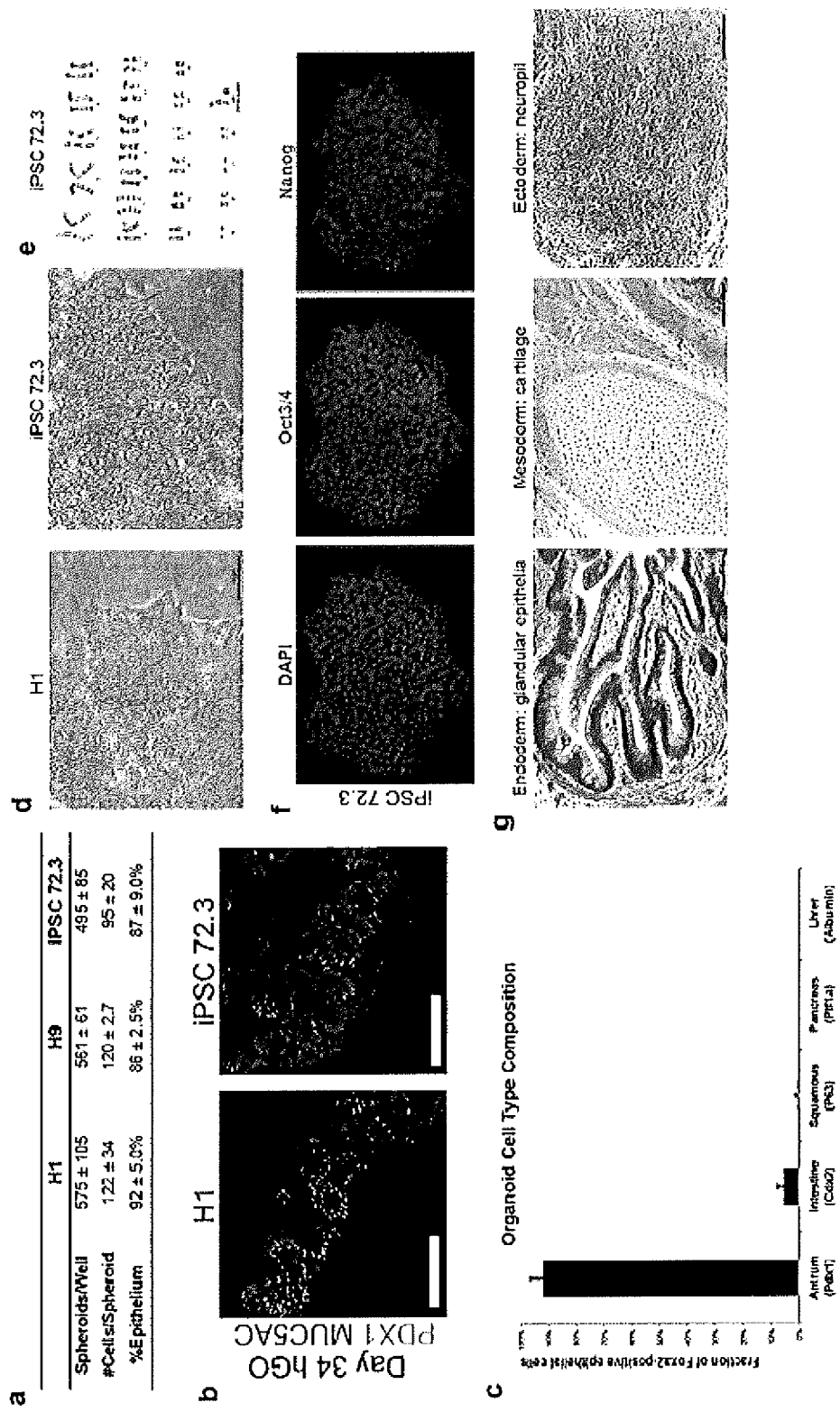
FIG. 6 depicts a table comparing spheroid formation and characteristics between two hESC lines (H1 and H9) and one iPSC line (72.3) (FIG. 6, Panel A), immunofluorescent staining of day 34 hGOs derived from H1 and iPSC 72.3 cell lines (FIG. 6, Panel B), organ epithelial cell type quantification in day 34 hGOs (FIG. 6, Panel C), characterization of the induced pluripotent stem cell line iPSC 72.3 (FIG. 6, Panels D-G).

Spheroid morphogenesis is a robust process in both hESC and hiPSC lines (FIG. 6A) and >90% of spheroid cells express SOX2 (FIG. 1C), indicating efficient specification into the foregut lineage. Thus, a new epistatic relationship between WNT, FGF and BMP has been identified by Applicant in which all three pathways cooperate to promote a mid-hindgut fate, whereas WNT and FGF act separately from BMP to drive assembly of endoderm and mesoderm into gut tube structures.

FIGS. 2A-2G depicts gastric organoid differentiation is an efficient and cell line-independent process. FIG. 2A, Table comparing spheroid formation and characteristics between two hESC lines (H1 and H9) and one iPSC line (72.3). FIG. 2B, Immunofluorescent staining of day 34 hGOs derived from H1 and iPSC 72.3 cell lines. iPSC-derived organoids exhibit the same morphological and molecular features of those derived from hESCs. FIG. 2C. Organ epithelial cell type quantification in day 34 hGOs. Greater than 90% of the epithelium is antral, indicated by PDX1 expression and lack of PTF1A expression, whereas less than 5% express markers associated with other organs derived from endoderm including CDX2 (intestine), albumin (liver) and p63 (squamous epithelium). d-g, Characterization of induced pluripotent stem cell line iPSC 72.3. FIG. 2D, iPSC 72.3 exhibits normal morphological characteristics of pluripotent stem cell colonies, as compared to the H1 hESC line and FIG. 2E, has a normal 46;XY karyotype. FIG. 2F, iPSC 72.3 expresses pluripotent markers OCT3/4 and NANOG, and FIG. 2G, demonstrates pluripotency by differentiation into endoderm, mesoderm, and ectoderm lineages in an in vivo teratoma assay. Scale bars, 100 μm. Error bars represent standard deviation.

Figure 7:
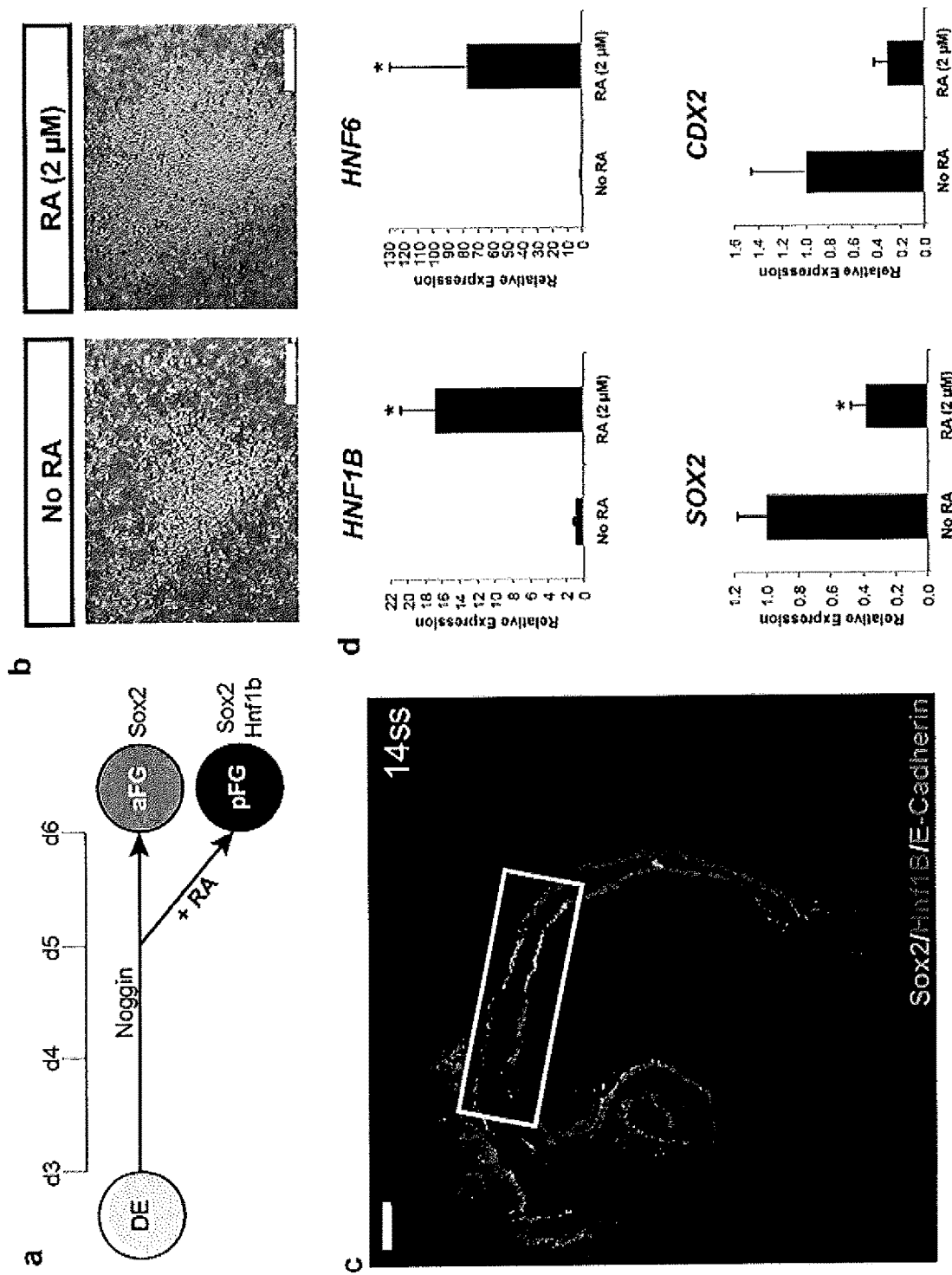
FIG. 7 depicts a schematic illustrating of foregut patterning experiments (FIG. 7, Panel A), Brightfield images that show that RA increases the number of spheroids that are produced from foregut monolayer cultures (FIG. 7, Panel B), a lower power image of (FIG. 1, Panel D) showing immunofluorescent image of a 14 somite stage embryo with Hnf1β protein localized to the posterior portion of the foregut (FIG. 7, Panel C), qPCR analysis of gene expression in foregut spheroids treated with RA (FIG. 7, Panel D).

In vivo, both the fundic and antral domains of the stomach arise from the posterior segment of Sox2$^+$ foregut endoderm, along with the pancreas, liver and duodenum. To direct SOX2$^+$ foregut spheroids into the gastric lineage, Applicant sought to identify signaling pathways that promote posterior foregut fate. Applicant focused on retinoic acid (RA) signaling given its role in development of posterior foregut-derived organs.[15-17] In vivo, the posterior foregut is marked by expression of Hnf1β (FIG. 1D). Applicant identified that a 24-hour exposure to RA on the final day (days 5-6) of the patterning/spheroid generation stage (FGF4/WNT3A/Noggin) results in robust activation of posterior foregut markers and the formation of SOX2/HNF1β$^+$ posterior foregut spheroids (FIG. 1E and FIG. 7). Thus, the precise temporal and combinatorial manipulation of RA, WNT, FGF, and BMP signaling pathways allowed for the generation of three-dimensional posterior foregut spheroids.

FIGS. 7A-7D shows that retinoic acid posteriorizes foregut endoderm. FIG. 7A depicts a schematic illustrating of foregut patterning experiments. DE cultures were treated with Wnt(CHIR)/FGF/noggin for three days to generate Sox2-positive foregut spheroids, and RA is added for 24 hours on the third day of patterning. FIG. 7B depicts Brightfield images that show that RA increases the number of spheroids that are produced from foregut monolayer cultures. FIG. 7C depicts a lower power image of FIG. 1D showing immunofluorescent image of a 14 somite stage embryo with Hnf1β 3 protein localized to the posterior portion of the foregut. Boxed region of embryo is shown in FIG. 1D. FIG. 7D shows qPCR analysis of gene expression in foregut spheroids treated with RA. Posterior foregut markers HNF1β and HNF6 are robustly induced by 24-hour exposure to RA. *, p<0.05. Scale bars, 1 mm in FIG. 7B; 100 μm in FIG. 7C. Error bars represent standard deviation.

The molecular mechanisms that direct the posterior foregut into distinct organ lineages are poorly understood. Early in development, presumptive organ domains are marked by distinct gene expression patterns: Sox2$^+$ fundus, Sox2/Pdx1$^+$ antrum, Pdx1/Ptf1α$^+$ pancreas, and Pdx1/Cdx2$^+$ duodenum (FIG. 2B). Applicant used these molecular markers to identify signaling pathways that direct posterior foregut spheroid cultures into the gastric lineage. Following transfer of spheroids to three-dimensional culture conditions, further treatment with RA for 72 hours (days 6-9) caused a >100-fold increase in PDX1 mRNA levels while maintaining high SOX2 expression (FIG. 2C). Importantly, the RA treatment did not promote a pancreatic fate as observed by others[9], since expression of the pancreas-specific marker PTF1α was not induced. These data demonstrate that the combination of RA signaling with three-dimensional growth efficiently direct posterior foregut spheroids into a SOX2/PDX1$^+$ epithelium indicative of an early antrum fate.

Figure 2:
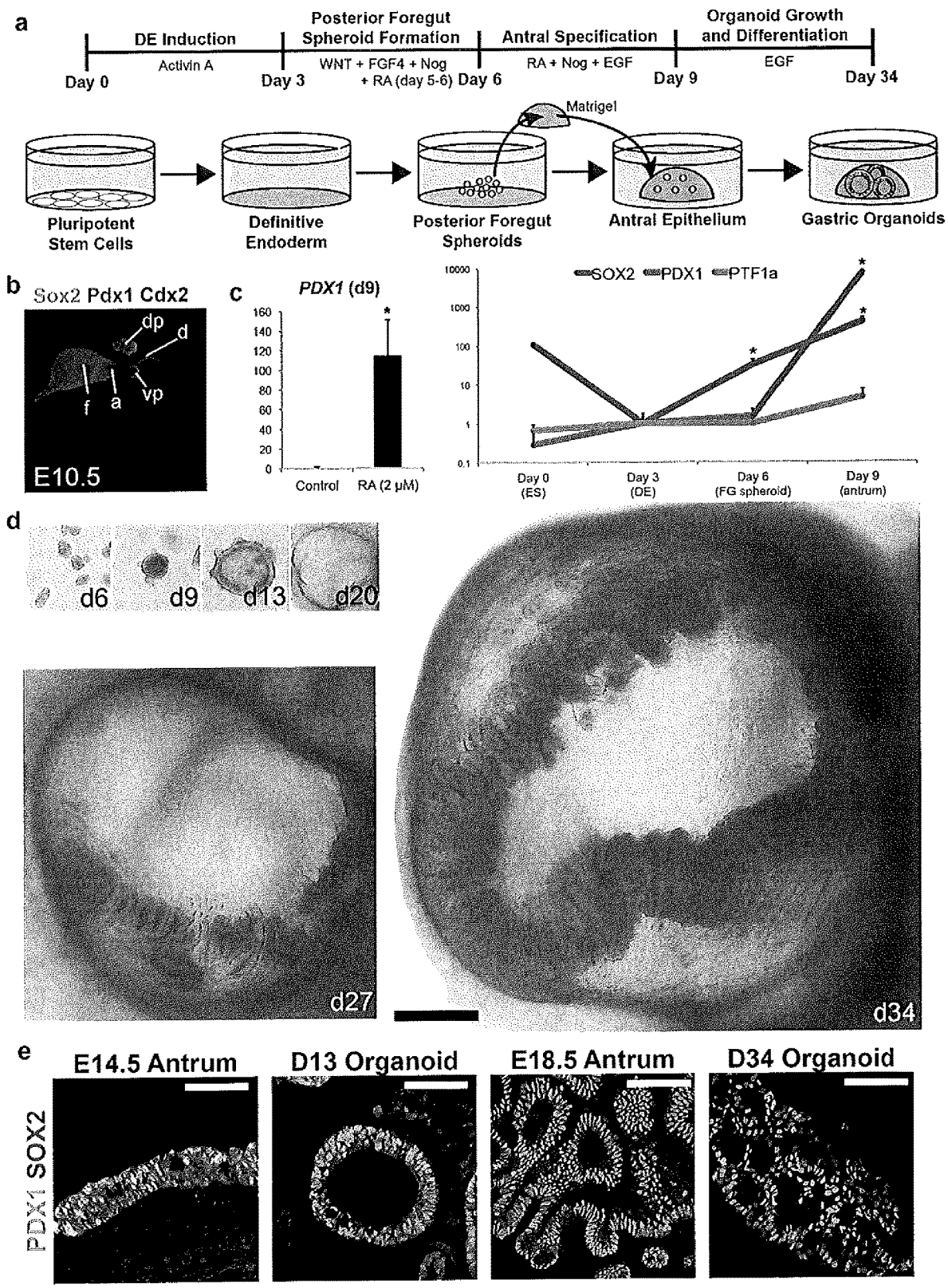
FIG. 2 depicts schematic representation of the in vitro culture system used to direct the differentiation of hPSCs into three-dimensional gastric organoids (FIG. 2, Panel A), the defining markers of developing posterior foregut organs by wholemount immunofluorescent staining of mouse E10.5 embryos with Sox2, Pdx1 and Cdx2 (FIG. 2, Panel B), PDX1 expression in the presence and absence of RA (FIG. 2, Panel C), stereomicrographs showing morphological changes during growth of posterior foregut spheroids into hGOs (FIG. 2, Panel D), and a comparison of developing mouse antrum at E14.5 and E18.5 and comparable stages of hGO development (FIG. 2, Panel E).

FIG. 2 generally depicts the specification and growth of human antral gastric organoids. Error bars represent standard deviation. FIG. 2A depicts schematic representation of the in vitro culture system used to direct the differentiation of hPSCs into three-dimensional gastric organoids, FIG. 2B depicts the defining markers of developing posterior foregut organs by wholemount immunofluorescent staining of mouse E10.5 embryos with Sox2, Pdx1 and Cdx2. Co-expression of Sox2 and Pdx1 is unique to the distal portion of the gastric epithelium, the presumptive antrum (a), Sox2 expression marks the fundus (f), Pdx1 (and Ptf1a) expression marks the dorsal (dp) and ventral (vp) pancreas, and Pdx1/Cdx2 co-expression marks the duodenum (d). FIG. 2C shows that the posterior foregut spheroids cultured in three-dimensional matrix for three days in the presence of RA (2 μM) co-expressed high levels of PDX1 and SOX2 and did not express the pancreatic marker PTF1α, similar to the developing antrum *, p<0.05. FIG. 2D depicts stereomicrographs showing morphological changes during growth of posterior forgut spheroids into gastric organoids. By four weeks, the epithelium of hGOs exhibited a complex glandular architecture, scale bar, 500 μm. FIG. 2E depicts a comparison of developing mouse antrum at E14.5 and E18.5 and comparable stages of hGO development. Sox2 and Pdx1 are co-expressed in the early pseudostratified epithelia in both mouse antrum and hGOs. At later stages, Sox2 is down-regulated as the epithelia transform into more mature glandular structures. Pdx1 is maintained in the antrum throughout adulthood in vivo and at all stages examined in hGOs, scale bars 100 μm in FIG. 2E.

Figure 8:
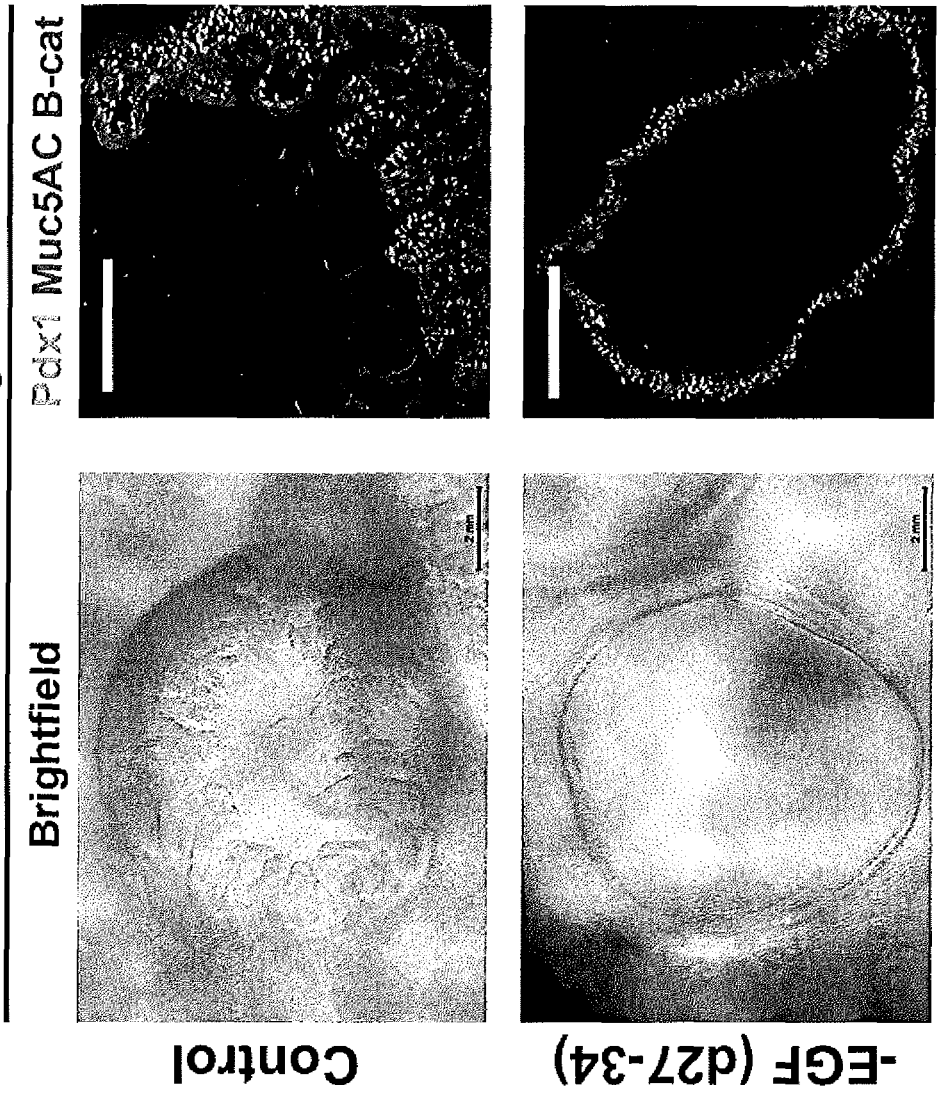
FIG. 8 depicts brightfield images and immunostaining at late stages of hGO differentiation.

Applicant used SOX2/PDX1+ spheroids to identify pathways that promote growth and morphogenesis of the early gastric epithelium and found that high concentrations of EGF (100 ng mL$^{-1}$) were sufficient to promote robust outgrowth of human antral gastric organoids (hGOs). Over the course of 3-4 weeks, spheroids that were <100 μm in diameter grew into organoids that were 2-4 mm in diameter. At the later stages of culture (~day 27), the hGO epithelium underwent a series of morphogenetic changes reminiscent of the late stages of embryonic gastric development, during which a simple, flat pseudostratified epithelium transitions into an elaborate, convoluted glandular epithelium (FIG. 2D). The initial outgrowth of foregut spheroids is dependent on EGF (data not shown); moreover, epithelial expansion and morphogenesis into glands does not occur when EGF is removed from the media at day 27 (FIG. 8). These results support published findings that indicate an important role for EGF in promoting proper growth of the gastric mucosa[19, 20].

FIG. 8 shows that EGF is required for glandular morphogenesis in gastric organoids. Brightfield images and immunostaining demonstrate the requirement for EGF for epithelial morphogenesis and gland formation at late stages of hGO differentiation. When EGF is removed from the growth medium at day 27, prior to glandular morphogenesis, the hGO epithelium retains a simple, cuboidal structure that fails to form glands. Scale bars, 100 μm.

A comparison of hGO growth with development of the embryonic mouse stomach revealed that hGO development is astonishingly similar to in vivo stomach organogenesis. At early stages (E12-14 in mouse and 13-day hGOs), both epithelia are pseudostratified and contain mitotic cells that are concentrated toward the luminal face (FIG. 9 and FIG. 10), indicating an interkinetic nuclear migration process[21]. The early hGOs are appropriately polarized and contain secondary lumina that are outlined by expression of the apical marker aPKC[22] (FIG. 10).

Figure 9:
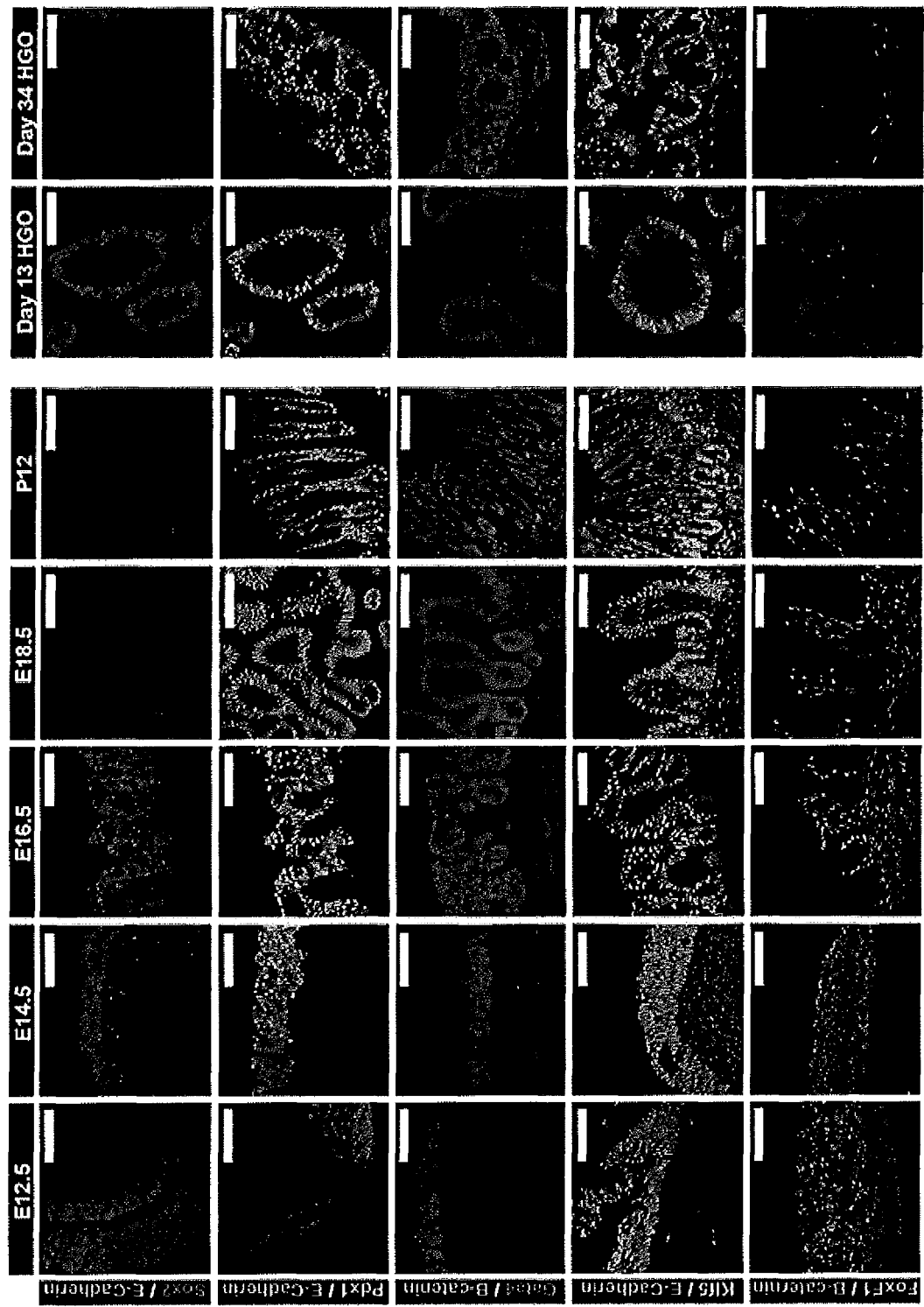
FIG. 9 depicts transcription factor expression during development of the mouse antrum and human gastric organoids during four embryonic stages (E12.5, E14.5, E16.5 and E18.5) and one postnatal stage (P12) of in vivo antrum development.
Figure 10:
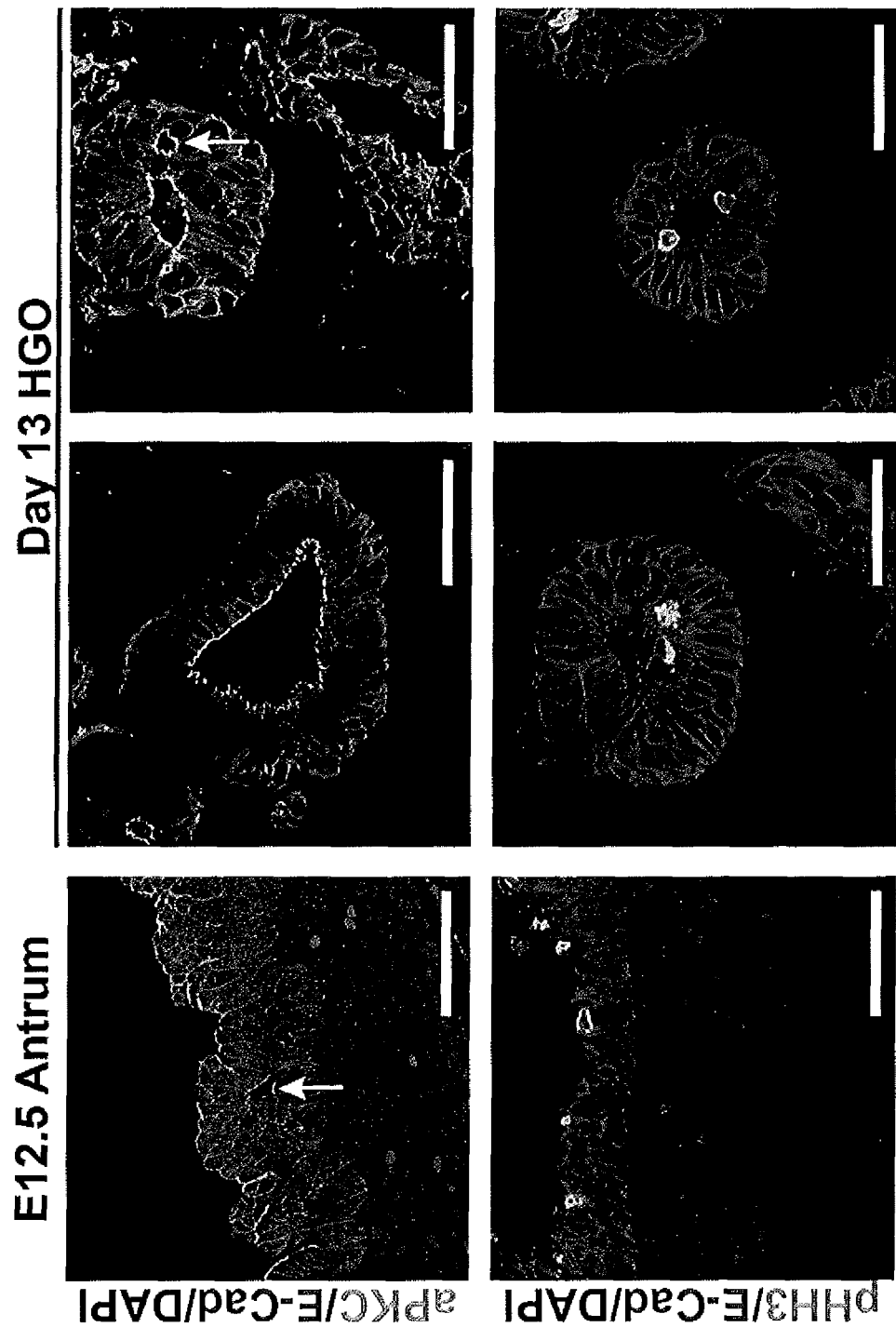
FIG. 10 depicts pHH3/E-Cad/DAPI expression and aPCC/E-CAD/DAPI expression in E12.5 Antrum and Day 13 hGO.

Between E16.5 and early postnatal stages, the antrum transforms into a simple columnar epithelium exhibiting a highly structured organization consisting of glands and pits (FIG. 2E and FIG. 9). Between 13 and 34 days in vitro, the hGO epithelium undergoes similar transitions to form a tall columnar epithelium with a glandular structure similar to the late fetal antrum (FIG. 2E). Analysis of expression of the transcription factors Sox2, Pdx1, Gata4 and Klf5 revealed a stereotypic temporospatial expression pattern that accompany these morphogenetic processes both in vivo and in vitro (FIG. 9). At early stages these factors are all co-expressed in the immature, pseudostratified epithelium. However at later stages, Sox2 expression is down-regulated as the epithelium forms early glands and pits, whereas the expression of the other factors is maintained indefinitely. Based on these data, it is estimated that 13-day hGOs represent a developmental stage similar to the E12-14 mouse antrum, whereas 34-day hGOs are more comparable to the late fetal-early postnatal antrum. Further, it is concluded that hGOs recapitulate normal embryonic development and that the molecular and morphogenetic processes that occur during antrum development are conserved between rodents and humans.

FIG. 9 shows a comparison of transcription factor expression during development of the mouse antrum and human gastric organoids. Four embryonic stages (E12.5, E14.5, E16.5 and E18.5) and one postnatal stage (P12) of in vivo antrum development were analyzed for transcription factor expression: Sox2, Pdx1, Gata4, Klf5, and FoxF1. The same markers were analyzed at two stages (day 13 and day 34) of in vitro hGO development and revealed that organoid development parallels what occurs in vivo. At early stages of antrum development the epithelial marker Sox2 is expressed ubiquitously but at later stages it is down-regulated, while other epithelial transcription factors, Pdx1, Gata4 and Klf5, exhibit persistent expression throughout development. Both early and late stage hGOs contain FoxF1-positive mesenchymal cells surrounding the epithelium. Scale bars, 100 μm. FIG. 10 shows that early stage human gastric organoids exhibit stereotypic architecture and nuclear behavior. At 13 days, hGOs contain pseudostratified epithelia that display apicobasal polarity marked by the apical marker aPKC and the basolateral marker E-Cadherin, similar to the E12.5 mouse antrum. Further, secondary lumina lined by apical membrane (white arrows) are seen within the organoid epithelium. Both the E12.5 mouse antrum and day 7 hGOs appear to undergo interkinetic nuclear migration, indicated by the presence of mitotic nuclei, pHH3, in only the apical portions of cells. Scale bars, 50 μm.

Figure 11:
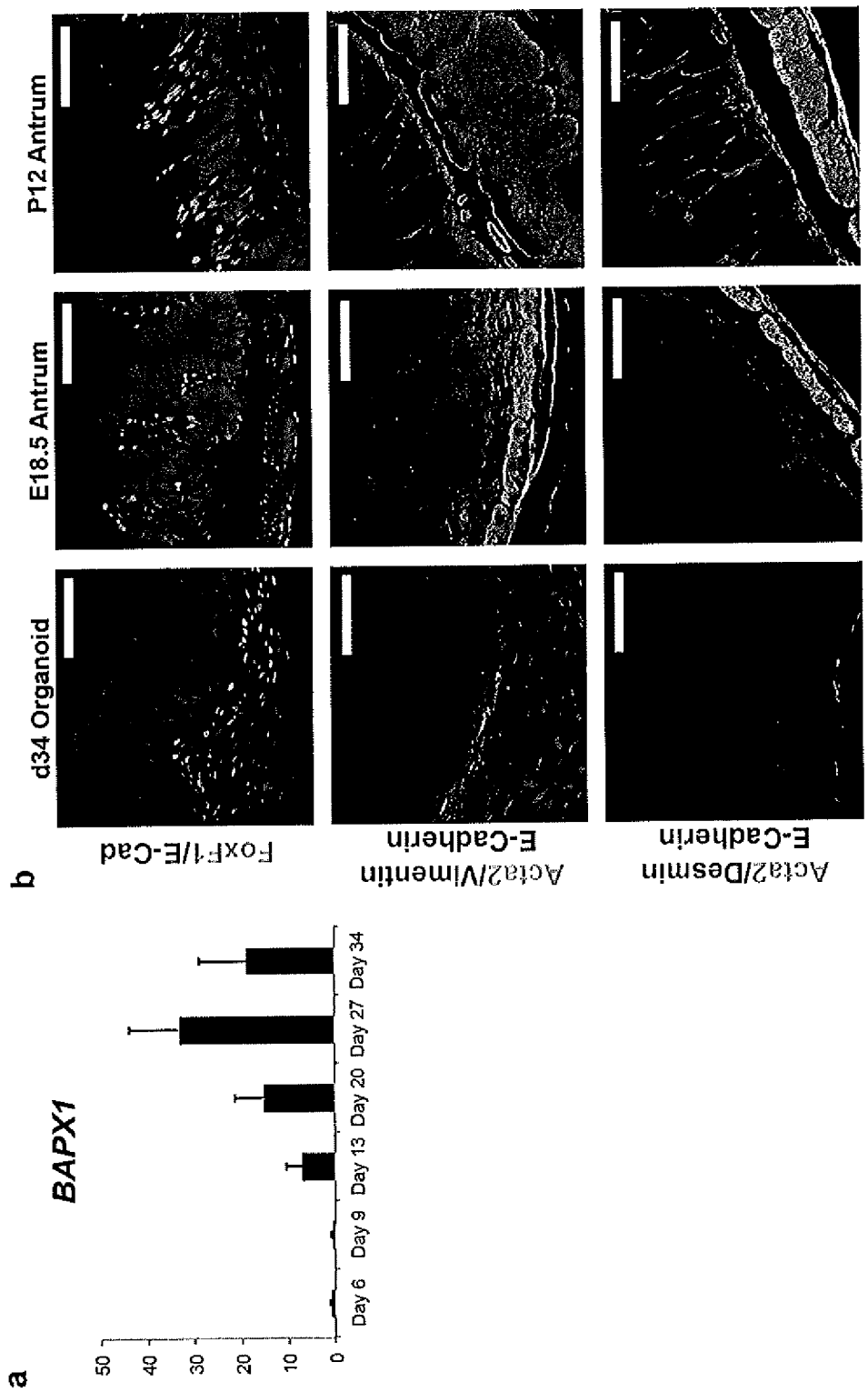
FIG. 11 depicts expression of the antral mesenchyme transcription factor BAPX1 (FIG. 11, Panel A) and staining for mesenchymal cell type markers (FIG. 11, Panel B).

The foregut spheroids contained a mesenchyme component similar to the mid-hindgut spheroids that were previously described. During the differentiation into gastric organoids, the mesenchyme expands and expresses key transcription factors associated with antral mesenchyme development, including FOXF1 and BAPX1 (FIG. 10 and FIG. 11). At later stages, hGO mesenchyme largely consists of VIMENTIN+ submucosal fibroblasts and a smaller number of ACTA2+ subepithelial myofibroblasts (FIG. 11), indicative of immature gastric mesenchyme. hGOs do not form differentiated layers of smooth muscle as occurs in vivo. Given that there is such robust epithelial morphogenesis in the absence of any exogenous factors except EGF, it seems likely that the mesenchyme plays a role in epithelial development. It is therefore surprising that the epithelium does not appear to promote robust differentiation of the mesenchyme. This suggests that other stimuli, possibly mechanical, play a role in gastric mesenchyme differentiation.

FIG. 11 shows mesenchymal differentiation in gastric organoids. FIG. 11A shows temporal expression analysis of the antral mesenchyme transcription factor BAPX1. Similar to its known embryonic expression pattern, BAPX1 is up-regulated during the earlier stages of hGO differentiation and then down-regulated coincident with functional cell type marker expression. FIG. 11B shows that staining for mesenchymal cell type markers reveals that day 34 hGOs contain FOXF1/VIMENTIN-positive submucosal fibroblasts and a small number of VIMENTIN/ALPHA-SM-ACTIN (SMA)-expressing subepithelial fibroblasts. hGOs lack a robust smooth muscle layer, indicated by SMA/Desmin-positive cells in the in vivo antrum. Scale bars, 100 μm. Error bars represent standard deviation.

The principal functional cell types found in the antrum are mucous cells, which secrete the protective mucus layers that line the gastric epithelium, and endocrine cells that secrete hormones to regulate gastrointestinal physiology and metabolic homeostasis[24]. By day 34, hGOs contain surface mucous cells (MUC5AC/UEAI+) that secrete mucus into the lumen and have the same tall columnar morphology as their in vivo counterpart. hGOs also contain TFF2/GSII+ antral gland cells, indicating appropriate differentiation in the antral mucous lineages (FIG. 3A). In addition, hGOs develop a progenitor cell niche, indicated by basally located zones of proliferation and SOX9 expression (FIG. 4A), although the proliferative index of the epithelium is variable and ranges between 1-10%. Thus, the in vitro hGOs contain a physiological gastric epithelium that comprises both progenitor and differentiated cell types.

Figure 4:
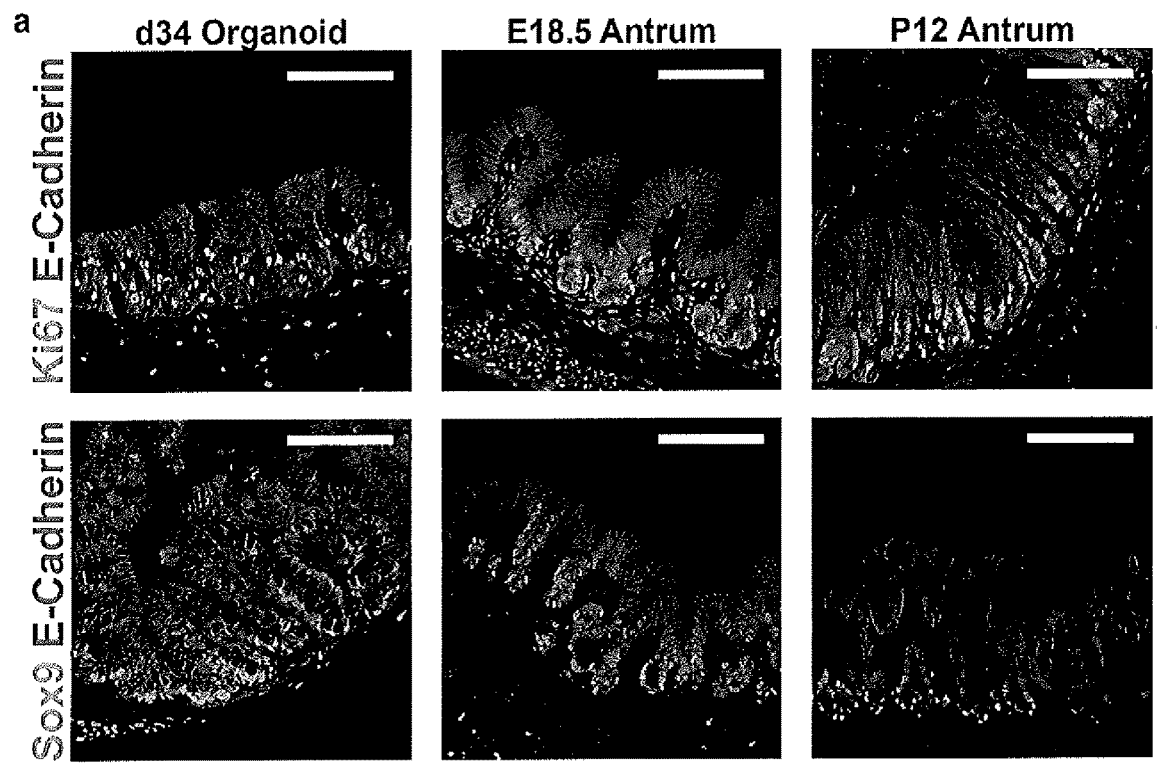
FIG. 4 depicts SOX9 Ki67 expression in d34 Organoid, E18.5 Antrum, and P12 Antrum (FIG. 4, Panel A), *H. Pylori* infection of organoids visualized using brightfield microscopy and immunofluorescent staining (FIG. 4, Panel B), immunoprecipitation for the oncogene c-Met (FIG. 4, Panel C), and cell proliferation in the hGO epithelium, measured by EdU incorporation (FIG. 4, Panel D).
Figure 4:
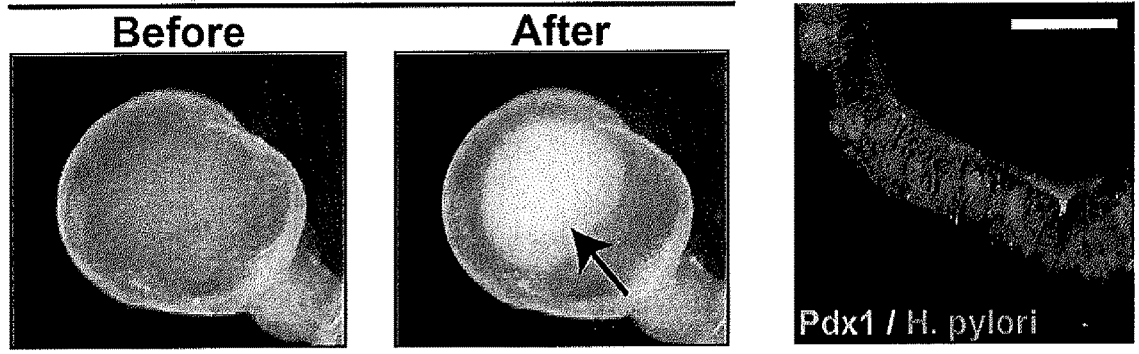
Figure 4:
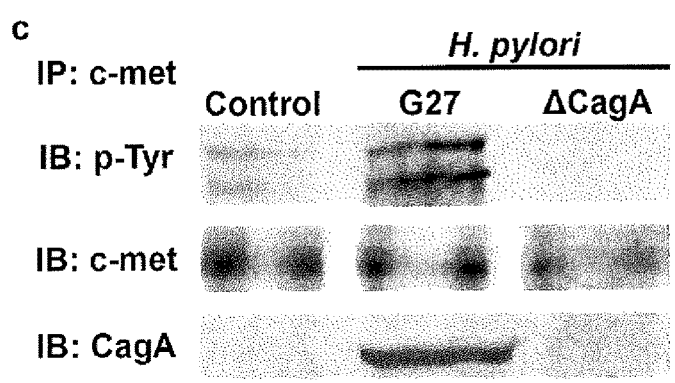
Figure 4:
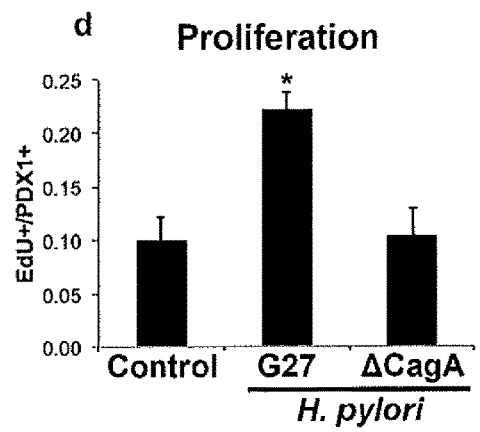

FIG. 4 shows that human gastric organoids exhibit acute responses to H. pylori infection. FIG. 4A shows that Day 28 hGOs contained proliferative cells, marked by Ki67, and SOX9+ progenitor cells that were restricted toward the bottoms of the early glands, similar to the late embryonic and postnatal mouse antrum. FIG. 4B shows that hGOs were used to model human-specific disease processes of H. pylori infection. Bacteria were microinjected into the lumen of hGOs and bacteria were visualized in the lumen 24 hours post-injection by brightfield microscopy (black arrow) and immunofluorescent staining. FIG. 4C depicts immunoprecipitation for the oncogene c-Met and demonstrates that H. pylori induced a robust activation (tyrosine phosphorylation) of c-Met, and that this is a CagA-dependent process. Further, CagA directly interacts with c-Met in human gastric epithelial cells. FIG. 4D shows that within 24 hours, H. pylori infection caused a two-fold increase in the number of proliferating cells in the hGO epithelium, measured by EdU incorporation. *, $p<0.05$. Scale bars, 100 μm in a; 25 μm in b. Error bars represent s.e.m.

Figure 3:
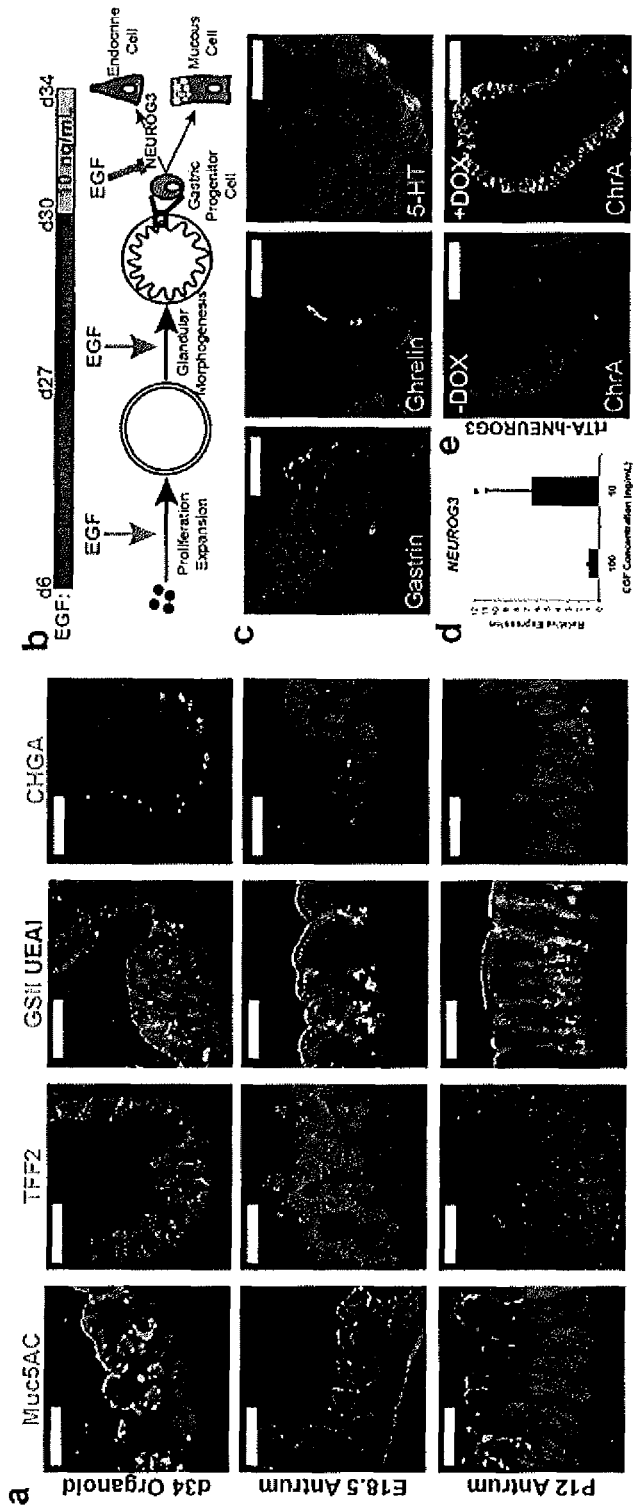
FIG. 3 depicts Muc5AC, TFF2, GSII UEAI, and CHGA expression in P12 Antrum, E18.5 Antrum and d34 Organoid (FIG. 3, Panel A), a schematic representation of the different roles for EGF in the growth, morphogenesis, and cell type specification during development of hGOs (FIG. 3, Panel B), expression of gastrin, ghrelin, 5-HT, and ChrA in gastric organoids with and without DOX (FIG. 3, Panel C), and relative expression of NEUROG3 at multiple concentrations of EGF (FIG. 3, Panel D).

FIG. 3 demonstrates that human gastric organoids contain normal differentiated antral cell types and can be used to model human stomach development. FIG. 3A demonstrates that hGOs contain all the major antral cell lineages. The 34-day hGOs have surface mucous cells (Muc5AC) and mucous gland cells (TFF2), as well as lectin staining that distinguishes surface mucous, UEAI, and mucous gland cells, GSII. hGOs also contain endocrine cells as marked by ChromograninA (CHGA). FIG. 3B is a schematic representation of the different roles for EGF in the growth, morphogenesis, and cell type specification during development of hGOs. High levels of EGF were required at early developmental stages for gland formation, however it repressed endocrine differentiation at late stages of development; thus, the EGF concentration was reduced at day 30 to allow for endocrine cell development. FIG. 3C shows that all major endocrine hormones are expressed in hGOs upon withdrawal of EGF including gastrin, ghrelin, and serotonin (5-HT). FIG. 3D shows that high levels of EGF repress NEUROG3 expression. A reduction in EGF concentration at day 30 resulted in a significant increase in NEUROG3 expression measured at day 34 by qPCR, indicating that EGF acts upstream of NEUROG3 in endocrine specification. *, $p<0.05$. FIG. 3E shows that NEUROG3 acts downstream of EGF to induce endocrine cell fate. Forced expression of NEUROG3 using a dox-inducible system was sufficient to override the endocrine-repressing effects of high EGF (100 ng mL−1). hGOs were exposed to dox (1 μg mL−1) for 24 hours at day 30 and analyzed at day 34. Dox-treated organoids exhibited a robust induction of ChrA-expressing endocrine cells. Scale bars, 100 μm. Error bars represent standard deviation.

Figure 12:
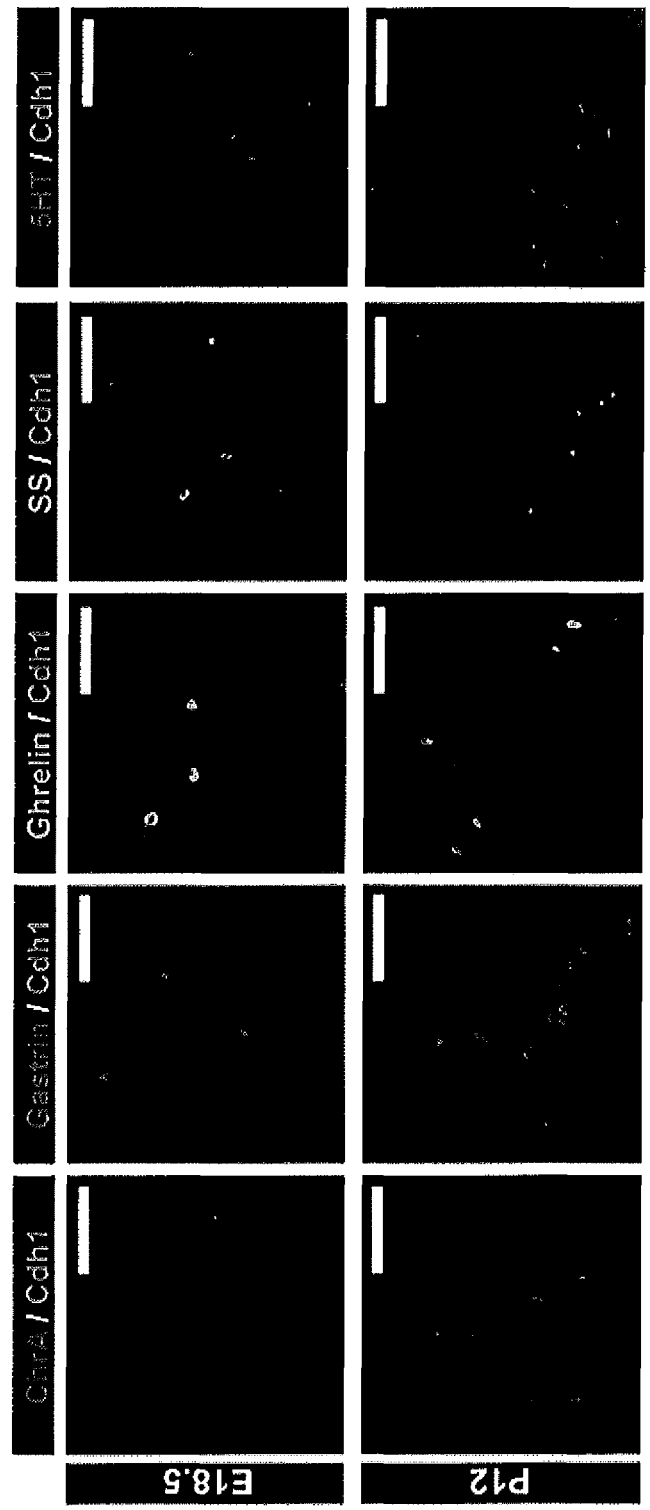
FIG. 12 depicts gastric antrum endocrine cell development in vivo.
Figure 13:
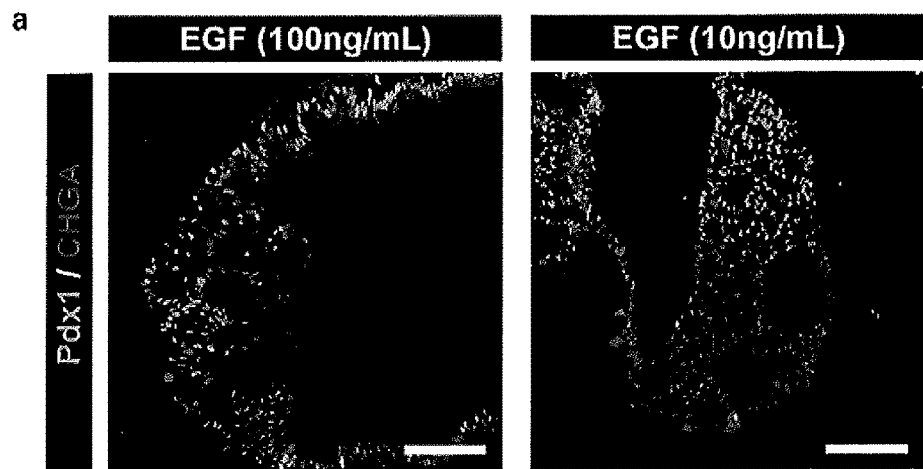
FIG. 13 depicts staining for the pan-endocrine marker CHGA (FIG. 13, Panel A) and expression of endocrine markers CHGA, GASTRIN, GHRELIN, and SOMATOSTATIN (FIG. 13, Panel B).
Figure 13:
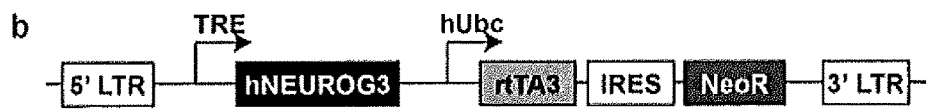
Figure 13:
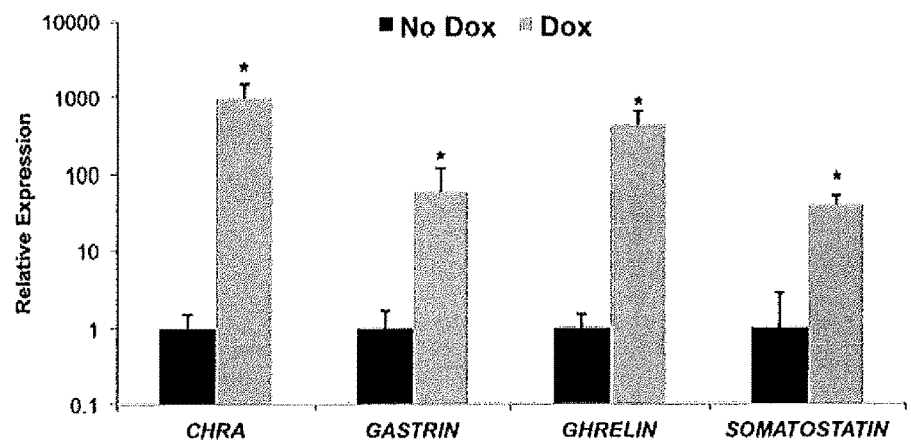
Figure 13:
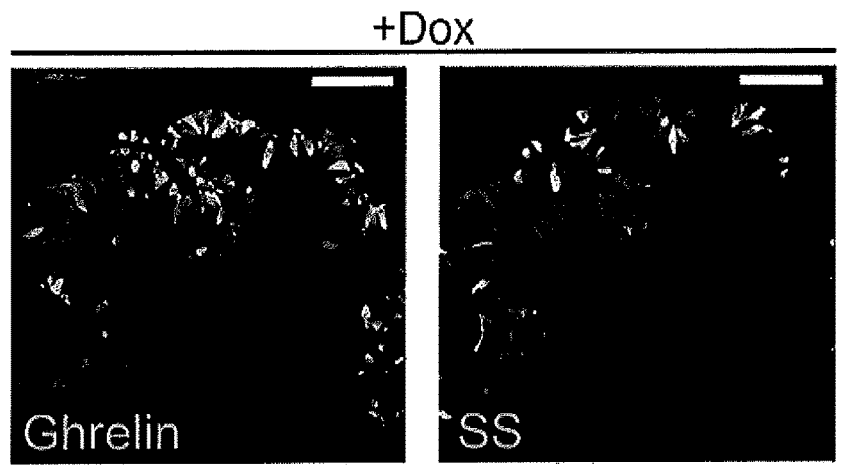

There is also an abundance of CHROMOGRANIN-A (CHGA)+ endocrine cells in 34-day hGOs, including the four main endocrine cell types in the antrum expressing gastrin, ghrelin, somatostatin, and serotonin (FIG. 3C and FIG. 12). Interestingly, we observed that high levels of EGF repress endocrine cell formation such that 100 ng ml−1 resulted in <1 endocrine cell per organoid. In contrast, hGOs cultured in lower levels of EGF (10 ng ml−1) from day 30-34 developed an abundance of endocrine cells (FIG. 13). Moreover, high EGF also inhibited expression of the proendocrine transcription factor NEUROG3 (FIG. 3D), which has been extensively studied in the pancreas and intestine[25-28] and is required in the formation of most gastric endocrine lineages[29,30]. These data suggest a novel inhibitory effect of EGFR signaling in gastric endocrine cell specification upstream of NEUROG3. To test this model, Applicant used a doxycycline-inducible hNEUROG3 overexpressing hESC line, and found that NEUROG3 expression was sufficient to overcome the endocrine inhibitory effect of high EGF (100 ng ml−1), resulting in robust formation of CHGA+ endocrine cells (FIG. 3E and FIG. 13). From these findings we concluded that EGF inhibits the formation of endocrine progenitor cells through repression of NEUROG3, and that NEUROG3 is sufficient for the specification of human gastric endocrine cells.

FIG. 12 shows gastric antrum endocrine cell development in vivo. Endocrine cell differentiation in the antrum is first evident at E18.5, but is more definitive at postnatal stages (P12 shown). At early stages, all expected gastric endocrine subtypes are evident, including gastrin, ghrelin, somatostatin, and serotonin (5-HT). Scale bars, 100 μm. FIG. 13 shows that EGF signaling represses a NEUROG3-dependent gastric endocrine specification program. FIG. 13A shows that hGOs maintained in high concentrations of EGF (100 ng mL−1) had very few endocrine cells at day 34, shown by staining for the pan-endocrine marker CHGA. A reduction of EGF concentration (10 ng mL−1) at day 24 resulted in more physiologic numbers of endocrine cells in the gastric epithelium. FIG. 13B shows generation of hGOs from a hESC line stably transfected with a dox-inducible NEUROG3-overexpressing transgene, to test whether EGF repression of endocrine differentiation occurs upstream of NEUROG3. hGOs were maintained in high EGF (100 ng mL−1) then at day 30 were treated with doxycycline (1 μg mL−1) for 24 hours and then analyzed at day 34. Dox-treated hGOs show robust activation of endocrine markers CHGA, GASTRIN, GHRELIN, and SOMATOSTATIN, and they contain CHGA-(FIG. 3A), GHRELIN-, and SOMATOSTATIN-positive cells with endocrine morphology. *, $p<0.05$. Scale bars, 100 μm. Error bars represent standard deviation.

Clinical evidence indicates that predominant colonization of the antrum has an important role in H. pylori-mediated disease[31,32]. Thus, Applicant tested whether hGOs could be used to model the pathophysiologic response of human stomach to the pathogen H. pylori. To mimic the normal host-pathogen interface, we introduced H. pylori directly to the luminal surface of the epithelium by microinjection into the lumen of the organoids and measured epithelial signaling and proliferation (FIG. 4). Bacteria were observed tightly associated with the hGO epithelium by immunofluorescence (FIG. 4B). Within 24 hours, Applicant observed significant epithelial responses to H. pylori including robust activation of the gastric oncogene c-Met[33] and a 2-fold increase in epithelial cell proliferation. The H. pylori virulence factor CagA plays a pivotal role in the etiology of disease. Consistent with published studies[34], Applicant demonstrated that CagA translocates into the organoid epithelial cells and forms a complex with c-Met (FIG. 4C). Furthermore, the epithelial response was abrogated when hGOs were injected with a non-pathogenic strain of H. pylori lacking CagA, reinforcing the importance of this factor in H. pylori-mediated human pathogenesis. Thus, the pathophysiological response of hGOs to H. pylori makes them an unprecedented model for elucidating the initiating events of human gastric disease mediated by H. pylori.

ADDITIONAL REFERENCES

1. Wen, S. & Moss, S. F. *Helicobacter pylori* virulence factors in gastric carcinogenesis. Cancer Lett. 282, 1-8 (2009).
2. Yuan, Y., Padol, I. T. & Hunt, R. H. Peptic ulcer disease today. Nat Clin Pract Gastroenterol Hepatol 3, 80-89 (2006).
3. Parkin, D. M. The global health burden of infection-associated cancers in the year 2002. Int. J. Cancer 118, 3030-3044 (2006).
4. Peek, R. M. *Helicobacter pylori* infection and disease: from humans to animal models. Dis Model Mech 1, 50-55 (2008).
5. Barker, N. et al. Lgr5(+ve) stem cells drive self-renewal in the stomach and build long-lived gastric units in vitro. Cell Stem Cell 6, 25-36 (2010).
6. Longmire, T. A. et al. Efficient Derivation of Purified Lung and Thyroid Progenitors from Embryonic Stem Cells. Stem Cell 10, 398-411 (2012).
7. Mou, H. et al. Generation of Multipotent Lung and Airway Progenitors from Mouse ESCs and Patient-Specific Cystic Fibrosis iPSCs. Stem Cell 10, 385-397 (2012).
8. Si-Tayeb, K. et al. Highly efficient generation of human hepatocyte-like cells from induced pluripotent stem cells. Hepatology 51, 297-305 (2010).
9. D'Amour, K. A. et al. Production of pancreatic hormone-expressing endocrine cells from human embryonic stem cells. Nat Biotechnol 24, 1392-1401 (2006).
10. Spence, J. R. et al. Directed differentiation of human pluripotent stem cells into intestinal tissue in vitro. Nature 470, 105-109 (2011).
11. D'Amour, K. A. et al. Efficient differentiation of human embryonic stem cells to definitive endoderm. Nat Biotechnol 23, 1534-1541 (2005).
12. McCracken, K. W., Howell, J. C., Spence, J. R. & Wells, J. M. Generating human intestinal tissue from pluripotent stem cells in vitro. Nature Protocols 6, 1920-1928 (2011).
13. Kumar, M., Jordan, N., Melton, D. & Grapin-Botton, A. Signals from lateral plate mesoderm instruct endoderm toward a pancreatic fate. Dev Biol 259, 109-122 (2003).
14. Tiso, N., Filippi, A., Pauls, S., Bortolussi, M. & Argenton, F. BMP signalling regulates anteroposterior endoderm patterning in zebrafish. Mech Dev 118, 29-37 (2002).
15. Wang, Z., Dolle, P., Cardoso, W. V. & Niederreither, K. Retinoic acid regulates morphogenesis and patterning of posterior foregut derivatives. Dev Biol 297, 433-445 (2006).
16. Martin, M. et al. Dorsal pancreas agenesis in retinoic acid-deficient Raldh2 mutant mice. Dev Biol 284, 399-411 (2005).
17. Molotkov, A., Molotkova, N. & Duester, G. Retinoic acid generated by Raldh2 in mesoderm is required for mouse dorsal endodermal pancreas development. Dev Dyn 232, 950-957 (2005).
18. Kawaguchi, Y. et al. The role of the transcriptional regulator Ptf1a in converting intestinal to pancreatic progenitors. Nat Genet 32, 128-134 (2002).
19. Johnson, L. R. & Guthrie, P. D. Stimulation of rat oxyntic gland mucosal growth by epidermal growth factor. Am. J. Physiol. 238, G45-9 (1980).
20. Majumdar, A. P. Postnatal undernutrition: effect of epidermal growth factor on growth and function of the gastrointestinal tract in rats. J. Pediatr. Gastroenterol. Nutr. 3, 618-625 (1984).
21. Spear, P. C. & Erickson, C. A. Interkinetic nuclear migration: A mysterious process in search of a function. Develop. Growth Differ. 54, 306-316 (2012).
22. Grosse, A. S. et al. Cell dynamics in fetal intestinal epithelium: implications for intestinal growth and morphogenesis. Development 138, 4423-4432 (2011).
23. Verzi, M. P. et al. Role of the homeodomain transcription factor Bapx1 in mouse distal stomach development. Gastroenterology 136, 1701-1710 (2009).
24. Mills, J. C. & Shivdasani, R. A. Gastric Epithelial Stem Cells. Gastroenterology 140, 412-424 (2011).
25. Gradwohl, G., Dierich, A., LeMeur, M. & Guillemot, F. neurogenin3 is required for the development of the four endocrine cell lineages of the pancreas. Proc Natl Acad Sci USA 97, 1607-1611 (2000).
26. Jenny, M. et al. Neurogenin3 is differentially required for endocrine cell fate specification in the intestinal and gastric epithelium. EMBO J 21, 6338-6347 (2002).
27. Johansson, K. A. et al. Temporal control of neurogenin3 activity in pancreas progenitors reveals competence windows for the generation of different endocrine cell types. Dev Cell 12, 457-465 (2007).
28. López-Diaz, L. et al. Intestinal Neurogenin 3 directs differentiation of a bipotential secretory progenitor to endocrine cell rather than goblet cell fate. Dev Biol 309, 298-305 (2007).
29. Schonhoff, S. E., Giel-Moloney, M. & Leiter, A. B. Neurogenin 3-expressing progenitor cells in the gastrointestinal tract differentiate into both endocrine and non-endocrine cell types. Dev Biol 270, 443-454 (2004).
30. Lee, C. S., Perreault, N., Brestelli, J. E. & Kaestner, K. H. Neurogenin 3 is essential for the proper specification of gastric enteroendocrine cells and the maintenance of gastric epithelial cell identity. Genes Dev 16, 1488-1497 (2002).
31. Olbe, L., Hamlet, A., Dalenbäck, J. & Fändriks, L. A mechanism by which *Helicobacter pylori* infection of the antrum contributes to the development of duodenal ulcer. Gastroenterology 110, 1386-1394 (2001).
32. Xia, H. H. et al. Antral-type mucosa in the gastric incisura, body, and fundus (antralization): a link between *Helicobacter pylori* infection and intestinal metaplasia? Am. J. Gastroenterol. 95, 114-121 (2000).
33. Churin, Y. et al. *Helicobacter pylori* CagA protein targets the c-Met receptor and enhances the motogenic response. J. Cell Biol. 161, 249-255 (2003).
34. Peek, R. M. et al. *Helicobacter pylori* cagA+ strains and dissociation of gastric epithelial cell proliferation from apoptosis. J. Natl. Cancer Inst. 89, 863-868 (1997).
35. Teo, A. K. K. et al. Activin and BMP4 Synergistically Promote Formation of Definitive Endoderm in Human Embryonic Stem Cells. Stem Cells 30, 631-642 (2012).
36. Meerbrey, K. L. et al. The pINDUCER lentiviral toolkit for inducible RNA interference in vitro and in vivo. Proc Natl Acad Sci USA 108, 3665-3670 (2011).
37. Okita, K. et al. An efficient nonviral method to generate integration-free human-induced pluripotent stem cells from cord blood and peripheral blood cells. Stem Cells 31, 458-466 (2013).
38. Covacci, A. et al. Molecular characterization of the 128-kDa immunodominant antigen of *Helicobacter pylori* associated with cytotoxicity and duodenal ulcer. Proc Natl Acad Sci USA 90, 5791-5795 (1993).
39. Amieva, M. R., Salama, N. R., Tompkins, L. S. & Falkow, S. *Helicobacter pylori* enter and survive within multivesicular vacuoles of epithelial cells. Cell. Microbiol. 4, 677-690 (2002).
40. Schumacher, M. A. et al. Gastric Sonic Hedgehog acts as a macrophage chemoattractant during the immune response to *Helicobacter pylori*. Gastroenterology 142, 1150-1159.e6 (2012).

What is claimed is:

1. A method of inducing formation of a gastric tissue, comprising the steps of:
   a) contacting a culture containing a mammalian definitive endoderm cell with an FGF signaling pathway activator, a Wnt signaling pathway activator, and a BMP inhibitor for a period of time sufficient to form SOX2+ foregut cells;
   b) contacting said SOX2+ foregut cells of step (a) with retinoic acid for a period of time sufficient to form three-dimensional foregut spheroids, wherein said three-dimensional foregut spheroids express SOX2, PDX1, HNF1beta, and HNF6;
   c) contacting said three-dimensional foregut spheroids of step (b) with retinoic acid, EGF and a BMP inhibitor for a period of time sufficient for formation of a gastric organoid, wherein said gastric organoid is characterized by expression of MUC5AC, gastrin, ghrelin, 5-HT, and ChrA and the presence of a cell type selected from an antral mucous cell, an endocrine cell, and a combination thereof.

2. The method of claim 1, wherein said definitive endoderm is derived from a precursor cell selected from an embryonic stem cell, an embryonic germ cell, an induced pluripotent stem cell, or a combination thereof.

3. The method of claim 1, wherein said definitive endoderm is obtained from a pluripotent stem cell contacted with one or more molecules selected from an Activin molecule, a BMP subgroup of the TGF-beta superfamily of growth factors, or a combination thereof.

4. The method of claim 1, wherein said FGF signaling pathway activator is selected from one or more molecules selected from FGF1, FGF2, FGF3, FGF4, FGF10, FGF11, FGF12, FGF13, FGF14, FGF15, FGF16, FGF17, FGF18, FGF19, FGF20, FGF21, FGF22, FGF23 and combinations thereof.

5. The method of claim 1, wherein said WNT signaling pathway activator is selected from one or more molecules selected from Wnt1, Wnt2, Wnt2b, Wnt3, Wnt3a, Wnt4, Wnt5a, Wnt5b, Wnt6, Wnt7a, Wnt7b, Wnt8a, Wnt8b, Wnt9a, Wnt9b, Wnt10a, Wnt10b, Wnt11, Wnt16, a small molecule activator of Wnt, a GSKβ inhibitor, or combinations thereof.

6. The method of claim 1, wherein said Wnt signaling pathway activator is Wnt3a, and wherein said FGF signaling pathway activator is FGF4.

7. The method of claim 1, wherein said BMP inhibitor is selected from Noggin, Dorsomorphin, LDN189, DMH-1, and combinations thereof.

8. The method of claim 1, wherein the retinoic acid of step c) is administered in an amount of between about 0.2 μM to about 20 μM.

9. The method of claim 1, wherein said EGF is provided at a concentration and length of time sufficient to increase said gastric organoids to greater than 1 mm in diameter.

10. A method of generating a gastric organoid comprising fundus tissue comprising the steps of
a) generating a definitive endoderm (DE) from a pluripotent stem cell;
b) contacting said definitive endoderm with an agent that activates the FGF pathway, an agent that activates the WNT pathway, an agent that inhibits the BMP pathway, and retinoic acid to generate a posterior foregut; and
c) contacting said posterior foregut with EGF, retinoic acid, an agent that activates the WNT pathway, and an agent that inhibits the BMP pathway to generate a fundus tissue.

11. The method of claim 5, wherein said GSKβ inhibitor comprises

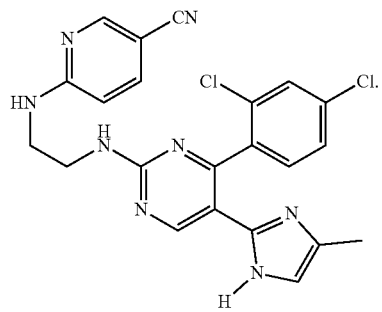

("CHIR99021")

12. The method of claim 1, wherein said Wnt signaling pathway activator is selected from lithium chloride; 2-amino-4,6-disubstituted pyrimidine (hetero) arylpyrimidines;

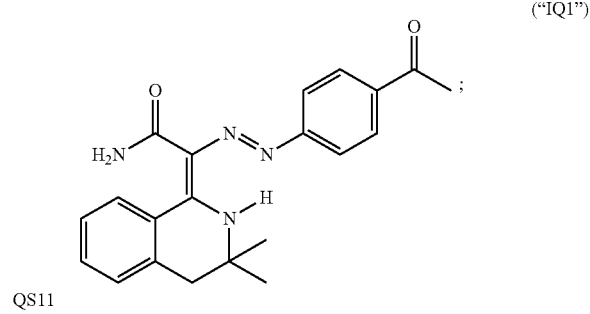

("IQ1")

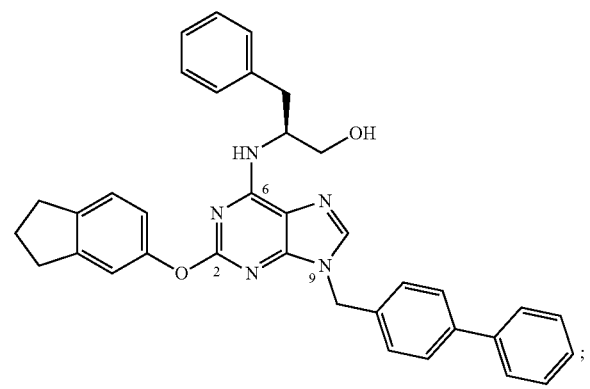

("QS11")

OCA beta-catenin; 2-amino-4-[3,4-(methylenedioxy)-benzyl-amino]-6-(3-methoxyphenyl) pyrimidine, and combinations thereof.

13. The method of claim 3, wherein said molecule is selected from Nodal, Activin A, Activin B, BMP4, Wnt3a, and combinations thereof.

14. The method of claim 1, wherein said step a) comprises contacting said definitive endoderm cell with both Wnt3a and FGF4.

15. The method of claim 1, wherein step a) comprises simultaneously contacting said definitive endoderm cell with said FGF signaling pathway activator, said Wnt signaling pathway activator, and said BMP inhibitor.

16. The method of claim 1, wherein step a) does not comprise contacting said definitive endoderm cell with either or both of said FGF signaling pathway activator and said Wnt signaling pathway activator at the same time as contacting with said BMP inhibitor.

17. The method of claim 1, wherein said period of time of step a) and b) is about 1 to about 4 days.

18. The method of claim 10, wherein said fundus tissue is characterized by expression of IRX3 and IRX5 and repression of Pdx1.

* * * * *

SEQUENCE LISTING

<160> NUMBER OF SEQ ID NOS: 64

<210> SEQ ID NO 1
<211> LENGTH: 20
<212> TYPE: DNA
<213> ORGANISM: Artificial Sequence
<220> FEATURE:
<223> OTHER INFORMATION: ATP4A - Forward Primer

<400> SEQUENCE: 1
tggtagtagc caaagcagcc                                              20

<210> SEQ ID NO 2
<211> LENGTH: 19
<212> TYPE: DNA
<213> ORGANISM: Artificial Sequence
<220> FEATURE:
<223> OTHER INFORMATION: ATP4A - Reverse Primer

<400> SEQUENCE: 2
tgccatccag gctagtgag                                               19

<210> SEQ ID NO 3
<211> LENGTH: 20
<212> TYPE: DNA
<213> ORGANISM: Artificial Sequence
<220> FEATURE:
<223> OTHER INFORMATION: ATP4B - Forward Primer

<400> SEQUENCE: 3
accacgtaga aggccacgta                                              20

<210> SEQ ID NO 4
<211> LENGTH: 20
<212> TYPE: DNA
<213> ORGANISM: Artificial Sequence
<220> FEATURE:
<223> OTHER INFORMATION: ATP4B - Reverse Primer

<400> SEQUENCE: 4
tggaggagtt ccagcgttac                                              20

<210> SEQ ID NO 5
<211> LENGTH: 20
<212> TYPE: DNA
<213> ORGANISM: Artificial Sequence
<220> FEATURE:
<223> OTHER INFORMATION: AXIN2 - Forward Primer

<400> SEQUENCE: 5
ctggtgcaaa gacatagcca                                              20

<210> SEQ ID NO 6
<211> LENGTH: 20
<212> TYPE: DNA
<213> ORGANISM: Artificial Sequence
<220> FEATURE:
<223> OTHER INFORMATION: AXIN2 - Reverse Primer

<400> SEQUENCE: 6
agtgtgaggt ccacggaaac                                              20

<210> SEQ ID NO 7
<211> LENGTH: 17
<212> TYPE: DNA
<213> ORGANISM: Artificial Sequence

```
<220> FEATURE:
<223> OTHER INFORMATION: BAPX1 - Forward Primer

<400> SEQUENCE: 7
caacaccgtc gtcctcg                                                  17

<210> SEQ ID NO 8
<211> LENGTH: 20
<212> TYPE: DNA
<213> ORGANISM: Artificial Sequence
<220> FEATURE:
<223> OTHER INFORMATION: BAPX1 - Reverse Primer

<400> SEQUENCE: 8
ccgcttccaa agacctagag                                               20

<210> SEQ ID NO 9
<211> LENGTH: 22
<212> TYPE: DNA
<213> ORGANISM: Artificial Sequence
<220> FEATURE:
<223> OTHER INFORMATION: CDX2 - Forward Primer

<400> SEQUENCE: 9
ctggagctgg agaaggagtt tc                                            22

<210> SEQ ID NO 10
<211> LENGTH: 24
<212> TYPE: DNA
<213> ORGANISM: Artificial Sequence
<220> FEATURE:
<223> OTHER INFORMATION: CDX2 - Reverse Primer

<400> SEQUENCE: 10
attttaacct gcctctcaga gagc                                          24

<210> SEQ ID NO 11
<211> LENGTH: 20
<212> TYPE: DNA
<213> ORGANISM: Artificial Sequence
<220> FEATURE:
<223> OTHER INFORMATION: CHGA - Forward Primer

<400> SEQUENCE: 11
tgacctcaac gatgcatttc                                               20

<210> SEQ ID NO 12
<211> LENGTH: 20
<212> TYPE: DNA
<213> ORGANISM: Artificial Sequence
<220> FEATURE:
<223> OTHER INFORMATION: CHGA - Reverse Primer

<400> SEQUENCE: 12
ctgtcctggc tcttctgctc                                               20

<210> SEQ ID NO 13
<211> LENGTH: 21
<212> TYPE: DNA
<213> ORGANISM: Artificial Sequence
<220> FEATURE:
<223> OTHER INFORMATION: GAPDH - Forward Primer

<400> SEQUENCE: 13
cccatcacca tcttccagga g                                             21
```

<210> SEQ ID NO 14
<211> LENGTH: 22
<212> TYPE: DNA
<213> ORGANISM: Artificial Sequence
<220> FEATURE:
<223> OTHER INFORMATION: GAPDH - Reverse Primer

<400> SEQUENCE: 14
cttctccatg gtggtgaaga cg                                              22

<210> SEQ ID NO 15
<211> LENGTH: 20
<212> TYPE: DNA
<213> ORGANISM: Artificial Sequence
<220> FEATURE:
<223> OTHER INFORMATION: GAST - Forward Primer

<400> SEQUENCE: 15
cagagccagt gcaaagatca                                                 20

<210> SEQ ID NO 16
<211> LENGTH: 20
<212> TYPE: DNA
<213> ORGANISM: Artificial Sequence
<220> FEATURE:
<223> OTHER INFORMATION: GAST - Reverse Primer

<400> SEQUENCE: 16
agagacctga gaggcaccag                                                 20

<210> SEQ ID NO 17
<211> LENGTH: 21
<212> TYPE: DNA
<213> ORGANISM: Artificial Sequence
<220> FEATURE:
<223> OTHER INFORMATION: GATA4 - Forward Primer

<400> SEQUENCE: 17
tccaaaccag aaaacggaag c                                               21

<210> SEQ ID NO 18
<211> LENGTH: 20
<212> TYPE: DNA
<213> ORGANISM: Artificial Sequence
<220> FEATURE:
<223> OTHER INFORMATION: GATA4 - Reverse Primer

<400> SEQUENCE: 18
gcccgtagtg agatgacagg                                                 20

<210> SEQ ID NO 19
<211> LENGTH: 20
<212> TYPE: DNA
<213> ORGANISM: Artificial Sequence
<220> FEATURE:
<223> OTHER INFORMATION: GHRL - Forward Primer

<400> SEQUENCE: 19
gctggtactg aaccccctgac                                                20

<210> SEQ ID NO 20
<211> LENGTH: 20
<212> TYPE: DNA
<213> ORGANISM: Artificial Sequence
<220> FEATURE:
<223> OTHER INFORMATION: GHRL - Reverse Primer

<400> SEQUENCE: 20
gatggaggtc aagcagaagg                                           20

<210> SEQ ID NO 21
<211> LENGTH: 21
<212> TYPE: DNA
<213> ORGANISM: Artificial Sequence
<220> FEATURE:
<223> OTHER INFORMATION: GKN1 - Foward Primer

<400> SEQUENCE: 21
agctagggca ggagctagaa a                                         21

<210> SEQ ID NO 22
<211> LENGTH: 20
<212> TYPE: DNA
<213> ORGANISM: Artificial Sequence
<220> FEATURE:
<223> OTHER INFORMATION: GKN1 - Reverse Primer

<400> SEQUENCE: 22
gcttgcctac tcctctgtcc                                           20

<210> SEQ ID NO 23
<211> LENGTH: 23
<212> TYPE: DNA
<213> ORGANISM: Artificial Sequence
<220> FEATURE:
<223> OTHER INFORMATION: HNF1B - Forward Primer

<400> SEQUENCE: 23
tcacagatac cagcagcatc agt                                       23

<210> SEQ ID NO 24
<211> LENGTH: 19
<212> TYPE: DNA
<213> ORGANISM: Artificial Sequence
<220> FEATURE:
<223> OTHER INFORMATION: HNF1B - Reverse Primer

<400> SEQUENCE: 24
gggcatcacc aggcttgta                                            19

<210> SEQ ID NO 25
<211> LENGTH: 20
<212> TYPE: DNA
<213> ORGANISM: Artificial Sequence
<220> FEATURE:
<223> OTHER INFORMATION: HNF6 - Forward Primer

<400> SEQUENCE: 25
tgttgcctct atccttccca                                           20

<210> SEQ ID NO 26
<211> LENGTH: 19
<212> TYPE: DNA
<213> ORGANISM: Artificial Sequence
<220> FEATURE:
<223> OTHER INFORMATION: HNF6 - Reverse Primer

<400> SEQUENCE: 26
ggaggatgtg gaagtggct                                            19

<210> SEQ ID NO 27

```
<211> LENGTH: 19
<212> TYPE: DNA
<213> ORGANISM: Artificial Sequence
<220> FEATURE:
<223> OTHER INFORMATION: IRX1 - Forward Primer

<400> SEQUENCE: 27
ccgtaggggt aataagccg                                                   19

<210> SEQ ID NO 28
<211> LENGTH: 20
<212> TYPE: DNA
<213> ORGANISM: Artificial Sequence
<220> FEATURE:
<223> OTHER INFORMATION: IRX1 - Reverse Primer

<400> SEQUENCE: 28
atctcagcct cttctcgcag                                                  20

<210> SEQ ID NO 29
<211> LENGTH: 17
<212> TYPE: DNA
<213> ORGANISM: Artificial Sequence
<220> FEATURE:
<223> OTHER INFORMATION: IRX2 - Forward Primer

<400> SEQUENCE: 29
gtggtgtgcg cgtcgta                                                     17

<210> SEQ ID NO 30
<211> LENGTH: 17
<212> TYPE: DNA
<213> ORGANISM: Artificial Sequence
<220> FEATURE:
<223> OTHER INFORMATION: IRX2 - Reverse Primer

<400> SEQUENCE: 30
ggcgttcagc ccctacc                                                     17

<210> SEQ ID NO 31
<211> LENGTH: 20
<212> TYPE: DNA
<213> ORGANISM: Artificial Sequence
<220> FEATURE:
<223> OTHER INFORMATION: IRX3 - Forward Primer

<400> SEQUENCE: 31
ggagagagcc gataagacca                                                  20

<210> SEQ ID NO 32
<211> LENGTH: 20
<212> TYPE: DNA
<213> ORGANISM: Artificial Sequence
<220> FEATURE:
<223> OTHER INFORMATION: IRX3 - Reverse Primer

<400> SEQUENCE: 32
agtgccttgg aagtggagaa                                                  20

<210> SEQ ID NO 33
<211> LENGTH: 20
<212> TYPE: DNA
<213> ORGANISM: Artificial Sequence
<220> FEATURE:
<223> OTHER INFORMATION: IRX5 - Forward primer

<400> SEQUENCE: 33
```
ggtgtgtggt cgtagggaga                                              20

<210> SEQ ID NO 34
<211> LENGTH: 19
<212> TYPE: DNA
<213> ORGANISM: Artificial Sequence
<220> FEATURE:
<223> OTHER INFORMATION: IRX5 - Reverse Primer

<400> SEQUENCE: 34
gctacaactc gcacctcca                                               19

<210> SEQ ID NO 35
<211> LENGTH: 19
<212> TYPE: DNA
<213> ORGANISM: Artificial Sequence
<220> FEATURE:
<223> OTHER INFORMATION: MIST1 - Forward Primer

<400> SEQUENCE: 35
tgctggacat ggtcaggat                                               19

<210> SEQ ID NO 36
<211> LENGTH: 20
<212> TYPE: DNA
<213> ORGANISM: Artificial Sequence
<220> FEATURE:
<223> OTHER INFORMATION: MIST1 - Reverse Primer

<400> SEQUENCE: 36
cggacaagaa gctctccaag                                              20

<210> SEQ ID NO 37
<211> LENGTH: 19
<212> TYPE: DNA
<213> ORGANISM: Artificial Sequence
<220> FEATURE:
<223> OTHER INFORMATION: MSX1 - Forward Primer

<400> SEQUENCE: 37
ggttcgtctt gtgtttgcg                                               19

<210> SEQ ID NO 38
<211> LENGTH: 17
<212> TYPE: DNA
<213> ORGANISM: Artificial Sequence
<220> FEATURE:
<223> OTHER INFORMATION: MSX1 - Reverse Primer

<400> SEQUENCE: 38
cccgagaagc ccgagag                                                 17

<210> SEQ ID NO 39
<211> LENGTH: 20
<212> TYPE: DNA
<213> ORGANISM: Artificial Sequence
<220> FEATURE:
<223> OTHER INFORMATION: MSX2 - Forward Primer

<400> SEQUENCE: 39
ggtcttgtgt ttcctcaggg                                              20

<210> SEQ ID NO 40
<211> LENGTH: 20
<212> TYPE: DNA

```
<213> ORGANISM: Artificial Sequence
<220> FEATURE:
<223> OTHER INFORMATION: MSX2 - Reverse Primer

<400> SEQUENCE: 40
aaattcagaa gatggagcgg                                               20

<210> SEQ ID NO 41
<211> LENGTH: 20
<212> TYPE: DNA
<213> ORGANISM: Artificial Sequence
<220> FEATURE:
<223> OTHER INFORMATION: MUC2 - Forwrad Primer

<400> SEQUENCE: 41
tgtaggcatc gctcttctca                                               20

<210> SEQ ID NO 42
<211> LENGTH: 20
<212> TYPE: DNA
<213> ORGANISM: Artificial Sequence
<220> FEATURE:
<223> OTHER INFORMATION: MUC2 - Reverse Primer

<400> SEQUENCE: 42
gacaccatct acctcacccg                                               20

<210> SEQ ID NO 43
<211> LENGTH: 20
<212> TYPE: DNA
<213> ORGANISM: Artificial Sequence
<220> FEATURE:
<223> OTHER INFORMATION: MUC5AC - Forward Primer

<400> SEQUENCE: 43
ccaaggagaa cctcccatat                                               20

<210> SEQ ID NO 44
<211> LENGTH: 18
<212> TYPE: DNA
<213> ORGANISM: Artificial Sequence
<220> FEATURE:
<223> OTHER INFORMATION: MUC5AC - Reverse Primer

<400> SEQUENCE: 44
ccaagcgtca ttcctgag                                                 18

<210> SEQ ID NO 45
<211> LENGTH: 24
<212> TYPE: DNA
<213> ORGANISM: Artificial Sequence
<220> FEATURE:
<223> OTHER INFORMATION: MUC6 - Forward Primer

<400> SEQUENCE: 45
cagcaggagg agatcacgtt caag                                          24

<210> SEQ ID NO 46
<211> LENGTH: 24
<212> TYPE: DNA
<213> ORGANISM: Artificial Sequence
<220> FEATURE:
<223> OTHER INFORMATION: MUC6 - Reverse Primer

<400> SEQUENCE: 46
gtgggtgttt tcctgtctgt catc                                          24
```

```
<210> SEQ ID NO 47
<211> LENGTH: 19
<212> TYPE: DNA
<213> ORGANISM: Artificial Sequence
<220> FEATURE:
<223> OTHER INFORMATION: NEUROG3 - Forward Primer

<400> SEQUENCE: 47
cttcgtcttc cgaggctct                                              19

<210> SEQ ID NO 48
<211> LENGTH: 20
<212> TYPE: DNA
<213> ORGANISM: Artificial Sequence
<220> FEATURE:
<223> OTHER INFORMATION: NEUROG3 - Reverse Primer

<400> SEQUENCE: 48 ctattcttt gcgccggtag                                              20

<210> SEQ ID NO 49
<211> LENGTH: 18
<212> TYPE: DNA
<213> ORGANISM: Artificial Sequence
<220> FEATURE:
<223> OTHER INFORMATION: PDX1 - Forward Primer

<400> SEQUENCE: 49
cgtccgcttg ttctcctc                                               18

<210> SEQ ID NO 50
<211> LENGTH: 20
<212> TYPE: DNA
<213> ORGANISM: Artificial Sequence
<220> FEATURE:
<223> OTHER INFORMATION: PDX1 - Reverse Primer

<400> SEQUENCE: 50
cctttcccat ggatgaagtc                                             20

<210> SEQ ID NO 51
<211> LENGTH: 18
<212> TYPE: DNA
<213> ORGANISM: Artificial Sequence
<220> FEATURE:
<223> OTHER INFORMATION: PITX1 - Forward Primer

<400> SEQUENCE: 51
ttcttggctg ggtcgtct                                               18

<210> SEQ ID NO 52
<211> LENGTH: 18
<212> TYPE: DNA
<213> ORGANISM: Artificial Sequence
<220> FEATURE:
<223> OTHER INFORMATION: PITX1 - Reverse Primer

<400> SEQUENCE: 52
tcgtctgaca cggagctg                                               18

<210> SEQ ID NO 53
<211> LENGTH: 20
<212> TYPE: DNA
<213> ORGANISM: Artificial Sequence
<220> FEATURE:
```

<223> OTHER INFORMATION: PTF1a - Foward Primer

<400> SEQUENCE: 53
agagagtgtc ctgctagggg                                         20

<210> SEQ ID NO 54
<211> LENGTH: 20
<212> TYPE: DNA
<213> ORGANISM: Artificial Sequence
<220> FEATURE:
<223> OTHER INFORMATION: PTF1a - Reverse Primer

<400> SEQUENCE: 54
ccagaaggtc atcatctgcc                                         20

<210> SEQ ID NO 55
<211> LENGTH: 22
<212> TYPE: DNA
<213> ORGANISM: Artificial Sequence
<220> FEATURE:
<223> OTHER INFORMATION: SST - Forward Primer

<400> SEQUENCE: 55
gcgctgtcca tcgtcctggc cc                                      22

<210> SEQ ID NO 56
<211> LENGTH: 22
<212> TYPE: DNA
<213> ORGANISM: Artificial Sequence
<220> FEATURE:
<223> OTHER INFORMATION: SST - Reverse Primer

<400> SEQUENCE: 56
agccgggttt gagttagcag at                                      22

<210> SEQ ID NO 57
<211> LENGTH: 20
<212> TYPE: DNA
<213> ORGANISM: Artificial Sequence
<220> FEATURE:
<223> OTHER INFORMATION: SOX2 - Forward Primer

<400> SEQUENCE: 57
gcttagcctc gtcgatgaac                                         20

<210> SEQ ID NO 58
<211> LENGTH: 20
<212> TYPE: DNA
<213> ORGANISM: Artificial Sequence
<220> FEATURE:
<223> OTHER INFORMATION: SOX2 - Reverse Primer

<400> SEQUENCE: 58
aaccccaaga tgcacaactc                                         20

<210> SEQ ID NO 59
<211> LENGTH: 20
<212> TYPE: DNA
<213> ORGANISM: Artificial Sequence
<220> FEATURE:
<223> OTHER INFORMATION: TFF1 - Forward Primer

<400> SEQUENCE: 59
aattctgtct ttcacgggggg                                        20

```
<210> SEQ ID NO 60
<211> LENGTH: 20
<212> TYPE: DNA
<213> ORGANISM: Artificial Sequence
<220> FEATURE:
<223> OTHER INFORMATION: TFF1 - Reverse Primer

<400> SEQUENCE: 60
ggagaacaag gtgatctgcg                                                 20

<210> SEQ ID NO 61
<211> LENGTH: 19
<212> TYPE: DNA
<213> ORGANISM: Artificial Sequence
<220> FEATURE:
<223> OTHER INFORMATION: TFF2 - Forward Primer

<400> SEQUENCE: 61
tctgagacct ccatgacgc                                                  19

<210> SEQ ID NO 62
<211> LENGTH: 20
<212> TYPE: DNA
<213> ORGANISM: Artificial Sequence
<220> FEATURE:
<223> OTHER INFORMATION: TFF2 - Reverse Primer

<400> SEQUENCE: 62
atggatgctg tttcgactcc                                                 20

<210> SEQ ID NO 63
<211> LENGTH: 18
<212> TYPE: DNA
<213> ORGANISM: Artificial Sequence
<220> FEATURE:
<223> OTHER INFORMATION: TFF3 - Forward Primer

<400> SEQUENCE: 63
cactccttgg gggtgaca                                                   18

<210> SEQ ID NO 64
<211> LENGTH: 20
<212> TYPE: DNA
<213> ORGANISM: Artificial Sequence
<220> FEATURE:
<223> OTHER INFORMATION: TFF3 - Reverse Primer

<400> SEQUENCE: 64
ctccagctct gctgaggagt                                                 20
```